(12) United States Patent
Metzmaker et al.

(10) Patent No.: US 10,258,736 B2
(45) Date of Patent: Apr. 16, 2019

(54) SYSTEMS INCLUDING VIAL ADAPTER FOR FLUID TRANSFER

(71) Applicant: Tandem Diabetes Care, Inc., San Diego, CA (US)

(72) Inventors: Thomas Metzmaker, San Diego, CA (US); Sean Saint, San Diego, CA (US); Michael Michaud, San Diego, CA (US); Michael J. Rosinko, Anaheim, CA (US); Vance Swanson, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 15/398,354

(22) Filed: Jan. 4, 2017

(65) Prior Publication Data

US 2017/0112997 A1 Apr. 27, 2017

Related U.S. Application Data

(63) Continuation of application No. 14/936,979, filed on Nov. 10, 2015, now Pat. No. 9,750,871, which is a continuation of application No. 13/474,032, filed on May 17, 2012, now Pat. No. 9,180,242.

(51) Int. Cl.
| | |
|---|---|
| *A61M 5/14* | (2006.01) |
| *A61M 5/168* | (2006.01) |
| *A61M 39/02* | (2006.01) |
| *A61J 1/20* | (2006.01) |
| *B65B 3/00* | (2006.01) |
| *A61M 39/10* | (2006.01) |

(52) U.S. Cl.
CPC .......... *A61M 5/1413* (2013.01); *A61J 1/2096* (2013.01); *A61M 5/16827* (2013.01); *A61M 39/02* (2013.01); *B65B 3/003* (2013.01); *A61M 2039/1077* (2013.01); *A61M 2039/1094* (2013.01); *A61M 2209/045* (2013.01)

(58) Field of Classification Search
CPC ........ B65B 3/006; B65B 3/003; A61M 39/10; A61M 2039/1077; A61M 2039/1094
USPC ............ 141/383, 386, 346–354, 2, 100, 104
See application file for complete search history.

(56) References Cited

U.S. PATENT DOCUMENTS

| | | |
|---|---|---|
| 318,856 A | 5/1885 | Bilz |
| 329,881 A | 11/1885 | Benton |
| 332,402 A | 12/1885 | Leadley |
| (Continued) | | |

FOREIGN PATENT DOCUMENTS

| | | |
|---|---|---|
| CN | 1229347 A | 9/1999 |
| CN | 2668155 Y | 1/2005 |
| (Continued) | | |

OTHER PUBLICATIONS

US 8,333,733 B2, 12/2012, Lanigan et al. (withdrawn)
(Continued)

*Primary Examiner* — Timothy L Maust
*Assistant Examiner* — Timothy P Kelly
(74) *Attorney, Agent, or Firm* — Patterson Thuente Pedersen, P.A.

(57) ABSTRACT

Devices and methods are disclosed for transferring fluids from supply reservoirs. The devices and methods may be configured to prevent or reduce the incidence of a user transferring a fluid to an incorrect receptacle reservoir.

10 Claims, 30 Drawing Sheets

(56) References Cited

U.S. PATENT DOCUMENTS

| | | |
|---|---|---|
| 596,062 A | 12/1897 | Firey |
| 722,431 A | 3/1903 | Packard |
| 818,938 A | 4/1906 | Crane |
| 926,092 A | 6/1909 | Bright |
| 1,079,522 A | 11/1913 | Smith |
| 1,274,884 A | 8/1918 | Hudson |
| 1,304,036 A | 5/1919 | Eshelby |
| 1,314,987 A | 9/1919 | Smith |
| 1,643,021 A | 9/1927 | Luyties |
| 1,657,663 A | 6/1928 | Devereux |
| 1,718,596 A | 6/1929 | Smith |
| 1,866,061 A | 7/1932 | Schoel |
| 1,910,032 A | 5/1933 | Mills |
| 2,018,316 A | 10/1935 | Ownings |
| 2,029,630 A | 2/1936 | McMichael |
| 2,147,164 A | 2/1939 | Kent |
| 2,398,234 A | 4/1946 | Long |
| 2,412,397 A | 12/1946 | Harper |
| 2,444,677 A | 7/1948 | Rosenblum |
| 2,454,929 A | 11/1948 | Kempton |
| 2,462,596 A | 2/1949 | Bent |
| 2,495,693 A | 1/1950 | Byrd, Jr. et al. |
| 2,497,020 A | 2/1950 | Singer |
| 2,568,519 A | 9/1951 | Smith |
| 2,599,325 A | 6/1952 | Fritzberg |
| 2,629,376 A | 2/1953 | Pierre et al. |
| 2,629,402 A | 2/1953 | Cook |
| 2,667,900 A | 2/1954 | Cantalupo |
| 2,674,262 A | 4/1954 | Bradshaw |
| 2,679,954 A | 6/1954 | Barnes |
| 2,691,542 A | 10/1954 | Chenoweth |
| 2,701,583 A | 2/1955 | Rux |
| 2,706,612 A | 4/1955 | Ratelband |
| 2,728,355 A | 12/1955 | Dahl |
| 2,735,642 A | 2/1956 | Norman |
| 2,736,463 A | 2/1956 | Michael |
| 2,746,709 A | 5/1956 | Minor |
| 2,764,183 A | 9/1956 | Gollehon |
| 2,781,058 A | 2/1957 | Warhus |
| 2,834,379 A | 5/1958 | Fields |
| 2,841,237 A | 7/1958 | Slayter |
| 2,852,033 A | 9/1958 | Orser |
| 2,878,836 A | 3/1959 | Binks |
| 2,891,578 A | 6/1959 | Dahl et al. |
| 2,898,078 A | 8/1959 | Stephenson et al. |
| 2,898,088 A | 8/1959 | Alder |
| 2,899,979 A | 8/1959 | Dahl et al. |
| 2,936,788 A | 5/1960 | Dahl et al. |
| 2,939,487 A | 6/1960 | Fraser et al. |
| 2,960,109 A | 11/1960 | Wilson |
| 2,968,318 A | 1/1961 | Bauman |
| 2,971,466 A | 2/1961 | Corbett |
| 2,989,086 A | 6/1961 | Dahl |
| 3,017,903 A | 1/1962 | Steffens |
| 3,023,750 A | 2/1962 | Baron |
| 3,035,613 A | 5/1962 | Beatty |
| 3,059,639 A | 10/1962 | Blackman et al. |
| 3,060,966 A | 10/1962 | Ratelband |
| 3,061,039 A | 10/1962 | Peters |
| 3,070,132 A | 12/1962 | Sheridan |
| 3,072,151 A | 1/1963 | Quercia |
| 3,095,120 A | 6/1963 | Steiner et al. |
| 3,095,175 A | 6/1963 | Iketani |
| 3,118,646 A | 1/1964 | Markey |
| 3,121,445 A | 2/1964 | Wisniewski |
| 3,123,900 A | 3/1964 | Millar |
| 3,133,678 A | 5/1964 | Marwell et al. |
| 3,143,861 A | 8/1964 | Dumas |
| 3,153,414 A | 10/1964 | Beall et al. |
| 3,174,694 A | 3/1965 | Kitabayshi |
| 3,187,562 A | 6/1965 | Rolfson |
| 3,189,125 A | 6/1965 | Windsor et al. |
| 3,195,586 A | 7/1965 | Vogt |
| 3,202,178 A | 8/1965 | Wolfe |
| 3,203,662 A | 8/1965 | Lau |
| 3,214,903 A | 11/1965 | Cochran |
| 3,216,451 A | 11/1965 | Smallpeice |
| 3,227,311 A | 1/1966 | Rowell |
| 3,298,394 A | 1/1967 | Chorkey |
| 3,302,578 A | 2/1967 | Anderson |
| 3,318,138 A | 5/1967 | Rolfson |
| 3,338,049 A | 8/1967 | Fernberger |
| 3,347,418 A | 10/1967 | Fefferman |
| 3,376,625 A | 4/1968 | McCulloch |
| 3,409,050 A | 11/1968 | Weese |
| 3,428,223 A | 2/1969 | Lewiecki et al. |
| 3,430,659 A | 3/1969 | Henderson |
| 3,455,147 A | 7/1969 | Peck et al. |
| 3,479,002 A | 11/1969 | Hirs |
| 3,493,496 A | 2/1970 | Bray et al. |
| 3,508,587 A | 4/1970 | Mauch |
| 3,532,125 A | 10/1970 | Everett et al. |
| 3,556,159 A | 1/1971 | Bleasdale |
| 3,568,847 A | 3/1971 | Carr |
| 3,583,603 A | 6/1971 | Freckmann et al. |
| 3,586,040 A | 6/1971 | Urback |
| 3,596,939 A | 6/1971 | Gibson |
| 3,620,500 A | 11/1971 | Santomieri |
| 3,621,882 A | 11/1971 | Kuplec |
| 3,654,959 A | 4/1972 | Kassel |
| 3,665,967 A | 5/1972 | Kachnik |
| 3,673,853 A | 7/1972 | Griswold et al. |
| 3,674,183 A | 7/1972 | Venable et al. |
| 3,675,672 A | 7/1972 | Freeman |
| 3,648,694 A | 8/1972 | Mogos et al. |
| 3,693,484 A | 9/1972 | Sanderson, Jr. |
| 3,696,958 A | 10/1972 | Lee |
| 3,699,812 A | 10/1972 | Masnik |
| 3,717,174 A | 2/1973 | Dewall |
| 3,724,234 A | 4/1973 | Garavelli |
| 3,756,459 A | 9/1973 | Bannister et al. |
| 3,833,019 A | 9/1974 | Diggs |
| 3,836,113 A | 9/1974 | Johnson |
| 3,837,363 A | 9/1974 | Meronek |
| 3,838,794 A | 10/1974 | Cogley et al. |
| 3,847,178 A | 11/1974 | Keppel |
| 3,860,353 A | 1/1975 | Lukasik et al. |
| 3,894,538 A | 7/1975 | Richter |
| 3,899,135 A | 8/1975 | O'Brian |
| 3,918,674 A | 11/1975 | Sutter |
| 3,946,761 A | 3/1976 | Thompson et al. |
| RE28,890 E | 7/1976 | Ingram et al. |
| 3,970,105 A | 7/1976 | Pelton et al. |
| 3,985,133 A | 10/1976 | Jenkins et al. |
| 3,991,972 A | 11/1976 | Eaton |
| 4,000,857 A | 1/1977 | Moen |
| 4,003,398 A | 1/1977 | Duveau |
| 4,023,772 A | 5/1977 | Ratelband |
| 4,028,931 A | 6/1977 | Bisera et al. |
| 4,032,265 A | 6/1977 | Miller |
| 4,042,153 A | 8/1977 | Callahan et al. |
| 4,076,872 A | 2/1978 | Lewiecki et al. |
| 4,087,301 A | 5/1978 | Steadman |
| 4,089,206 A | 5/1978 | Raffel et al. |
| 4,103,689 A | 8/1978 | Leighton |
| 4,105,050 A | 8/1978 | Hendrickson et al. |
| 4,106,510 A | 8/1978 | Hakim et al. |
| 4,111,391 A | 9/1978 | Pilolla |
| 4,137,913 A | 2/1979 | Georgi |
| 4,156,127 A | 5/1979 | Sako et al. |
| 4,178,938 A | 12/1979 | Au |
| 4,191,184 A | 3/1980 | Carlisle |
| 4,191,204 A | 3/1980 | Nehring |
| 4,191,358 A | 3/1980 | Ferri |
| 4,193,552 A | 3/1980 | Ishikawa |
| 4,195,810 A | 4/1980 | Lavin |
| 4,215,726 A | 8/1980 | Tagami |
| 4,228,956 A | 10/1980 | Varner |
| 4,248,270 A | 2/1981 | Ostrowski |
| 4,250,872 A | 2/1981 | Tamari |
| 4,254,791 A | 3/1981 | Bron |
| 4,265,241 A | 5/1981 | Portner et al. |
| 4,275,727 A | 6/1981 | Keeri-Szanto |
| 4,271,989 A | 7/1981 | O'Neill |

(56) References Cited

U.S. PATENT DOCUMENTS

| | | |
|---|---|---|
| 4,306,556 A | 12/1981 | Zelman |
| 4,314,621 A | 2/1982 | Hansen |
| 4,314,979 A | 2/1982 | Deabriges |
| 4,327,845 A | 5/1982 | Keyes et al. |
| 4,330,071 A | 5/1982 | Ohlson |
| 4,344,459 A | 8/1982 | Nelson |
| 4,356,935 A | 11/1982 | Kamin |
| 4,367,786 A | 1/1983 | Hafner et al. |
| 4,382,453 A | 5/1983 | Bujan et al. |
| 4,405,294 A | 9/1983 | Albarda |
| 4,406,656 A | 9/1983 | Hattler et al. |
| 4,411,651 A | 10/1983 | Schulman |
| 4,411,652 A | 10/1983 | Kramer |
| 4,416,596 A | 11/1983 | Lichtenstein |
| 4,432,468 A | 2/1984 | Siff et al. |
| 4,440,154 A | 4/1984 | Bellows |
| 4,440,323 A | 4/1984 | Benson |
| 4,443,218 A | 4/1984 | DeCant, Jr. et al. |
| 4,444,546 A | 4/1984 | Pazemenas |
| 4,448,538 A | 5/1984 | Mantel |
| 4,457,343 A | 7/1984 | Zukausky |
| 4,469,481 A | 9/1984 | Kobayshi |
| 4,481,808 A | 11/1984 | Sakata et al. |
| 4,491,155 A | 1/1985 | Meyer et al. |
| 4,492,339 A | 1/1985 | Kreitzberg |
| 4,498,843 A | 2/1985 | Schneider et al. |
| 4,508,144 A | 4/1985 | Bernett |
| 4,515,536 A | 5/1985 | van Os |
| 4,520,948 A | 6/1985 | Hampel et al. |
| 4,529,401 A | 6/1985 | Leslie et al. |
| 4,527,595 A | 7/1985 | Jorgensen et al. |
| 4,529,106 A | 7/1985 | Broadfoot et al. |
| 4,557,726 A | 12/1985 | Reinicke |
| 4,559,036 A | 12/1985 | Wunsch |
| 4,559,038 A | 12/1985 | Berg et al. |
| 4,562,751 A | 1/1986 | Nason et al. |
| 4,562,960 A | 1/1986 | Marty et al. |
| 4,565,542 A | 1/1986 | Berg |
| 4,570,745 A | 2/1986 | Sparks et al. |
| 4,573,994 A | 3/1986 | Fischell et al. |
| 4,592,390 A | 6/1986 | Boyd |
| 4,609,014 A | 9/1986 | Jurevic et al. |
| 4,620,648 A | 11/1986 | Schwartzman |
| 4,624,661 A | 11/1986 | Arimond |
| 4,627,573 A | 12/1986 | Havens et al. |
| 4,628,928 A | 12/1986 | Lowell |
| 4,636,226 A | 1/1987 | Canfora |
| 4,646,945 A | 3/1987 | Steiner et al. |
| 4,649,959 A | 3/1987 | Wadleigh |
| 4,650,469 A | 3/1987 | Berg et al. |
| 4,650,471 A | 3/1987 | Tamari |
| 4,651,781 A | 3/1987 | Kandelman |
| 4,657,486 A | 4/1987 | Stempfle et al. |
| 4,666,430 A | 5/1987 | Brown et al. |
| 4,667,700 A | 5/1987 | Buzzi |
| 4,673,415 A | 6/1987 | Stanford |
| 4,678,408 A | 7/1987 | Nason et al. |
| 4,678,460 A | 7/1987 | Rosner et al. |
| 4,684,364 A | 8/1987 | Sawyer et al. |
| 4,684,367 A | 8/1987 | Schaffer et al. |
| 4,685,903 A | 8/1987 | Cable et al. |
| 4,687,423 A | 8/1987 | Maget |
| 4,699,615 A | 10/1987 | Fischell et al. |
| 4,713,063 A | 12/1987 | Krumme |
| 4,718,430 A | 1/1988 | Holzer |
| 4,718,893 A | 1/1988 | Dorman et al. |
| 4,723,947 A | 2/1988 | Konopka |
| 4,724,870 A | 2/1988 | Molb k et al. |
| 4,741,736 A | 5/1988 | Brown |
| 4,770,211 A | 9/1988 | Olsson |
| 4,773,448 A | 9/1988 | Francis |
| 4,778,451 A | 10/1988 | Kamen |
| 4,779,762 A | 10/1988 | Klein et al. |
| 4,776,842 A | 11/1988 | Franetzki et al. |
| 4,787,408 A | 11/1988 | Twerdochlib |
| 4,793,486 A | 12/1988 | Konopka et al. |
| 4,795,433 A * | 1/1989 | Sarnoff ............... A61K 9/0019 604/134 |
| 4,808,167 A | 2/1989 | Mann et al. |
| 4,810,243 A | 3/1989 | Howson |
| 4,823,844 A | 4/1989 | Bartholomew |
| 4,826,482 A | 5/1989 | Kamen |
| 4,840,191 A | 6/1989 | Gausman et al. |
| 4,850,972 A | 7/1989 | Schulman et al. |
| 4,850,980 A | 7/1989 | Lentz et al. |
| 4,869,431 A | 9/1989 | Jubert et al. |
| 4,871,093 A | 10/1989 | Burshtain et al. |
| 4,883,093 A | 11/1989 | Miles et al. |
| 4,886,499 A | 12/1989 | Cirelli et al. |
| 4,886,514 A | 12/1989 | Maget |
| 4,893,966 A | 1/1990 | Roehl |
| 4,897,906 A | 2/1990 | Bartholomew |
| 4,902,278 A | 2/1990 | Maget |
| 4,919,596 A | 4/1990 | Slate et al. |
| 4,931,050 A | 6/1990 | Idriss |
| 4,936,832 A | 6/1990 | Vaillancourt |
| 4,938,259 A | 7/1990 | Schmidt |
| 4,955,860 A | 9/1990 | Ruano |
| 4,962,092 A | 10/1990 | Wood, Jr. |
| 4,969,884 A | 11/1990 | Yum |
| 4,973,402 A | 11/1990 | Johnson et al. |
| 4,976,162 A | 12/1990 | Kamen |
| 4,985,015 A | 1/1991 | Oberman et al. |
| 4,986,312 A | 1/1991 | Gute |
| 4,989,456 A | 2/1991 | Stupecky |
| 4,995,258 A | 2/1991 | Frank |
| 5,000,739 A | 3/1991 | Kulisz et al. |
| 5,002,527 A | 3/1991 | Reller et al. |
| 5,005,403 A | 4/1991 | Steudle et al. |
| 5,006,997 A | 4/1991 | Reich |
| 5,011,477 A | 4/1991 | Winchell et al. |
| 5,041,086 A | 4/1991 | Koenig et al. |
| 5,020,562 A | 6/1991 | Richmond et al. |
| 5,027,861 A | 7/1991 | Gute |
| 5,035,865 A | 7/1991 | Inaba et al. |
| 5,038,821 A | 8/1991 | Maget |
| 5,044,900 A | 9/1991 | Cavallaro |
| 5,047,044 A | 9/1991 | Smith et al. |
| 5,049,141 A | 9/1991 | Olive |
| 5,050,612 A | 9/1991 | Matsumura |
| 5,053,001 A | 10/1991 | Reller et al. |
| 5,053,189 A | 10/1991 | Chrise et al. |
| 5,059,171 A | 10/1991 | Bridge et al. |
| 5,059,182 A | 10/1991 | Laing |
| 5,062,834 A | 11/1991 | Gross et al. |
| 5,062,841 A | 11/1991 | Siegel |
| 5,076,911 A | 12/1991 | Brown et al. |
| 5,078,683 A | 1/1992 | Sancoff et al. |
| 5,080,653 A | 1/1992 | Voss et al. |
| 5,082,240 A | 1/1992 | Richmond |
| 5,082,503 A | 1/1992 | Sluga et al. |
| 5,083,908 A | 1/1992 | Gagnebin et al. |
| 5,084,021 A | 1/1992 | Baldwin |
| 5,085,644 A | 2/1992 | Watson et al. |
| 5,087,245 A | 2/1992 | Daon |
| 5,090,963 A | 2/1992 | Gross et al. |
| 5,091,091 A | 2/1992 | Terman |
| 5,091,094 A | 2/1992 | Veech |
| 5,108,363 A | 2/1992 | Tuttle et al. |
| 5,096,385 A | 3/1992 | Georgi et al. |
| 5,097,122 A | 3/1992 | Colman et al. |
| 5,103,211 A | 4/1992 | Daoud et al. |
| 5,104,526 A | 4/1992 | Brown et al. |
| 5,104,813 A | 4/1992 | Besemer et al. |
| 5,125,781 A | 6/1992 | Breunig et al. |
| 5,126,324 A | 6/1992 | Clark et al. |
| 5,127,258 A | 7/1992 | Brown et al. |
| 5,128,145 A | 7/1992 | Edgren et al. |
| 5,131,816 A | 7/1992 | Brown |
| 5,135,491 A | 8/1992 | Baldwin |
| 5,135,498 A | 8/1992 | Kam et al. |
| 5,135,499 A | 8/1992 | Tafani et al. |
| 5,148,154 A | 9/1992 | MacKay et al. |
| 5,149,413 A | 9/1992 | Maget |

(56) References Cited

U.S. PATENT DOCUMENTS

| | | |
|---|---|---|
| 5,154,712 A | 10/1992 | Herwick et al. |
| 5,156,591 A | 10/1992 | Gross et al. |
| 5,156,598 A | 10/1992 | Skakoon et al. |
| 5,157,960 A | 10/1992 | Brehm et al. |
| 5,158,230 A | 10/1992 | Curran |
| 5,167,633 A | 12/1992 | Mann et al. |
| 5,170,912 A | 12/1992 | Du |
| 5,170,986 A | 12/1992 | Zelczer et al. |
| 5,173,302 A | 12/1992 | Holmblad et al. |
| 5,176,502 A | 1/1993 | Sanderson et al. |
| 5,176,644 A | 1/1993 | Srisathapat et al. |
| 5,176,662 A | 1/1993 | Bartholomew et al. |
| 5,178,603 A | 1/1993 | Prince |
| 5,181,910 A | 1/1993 | Scanlon |
| 5,182,258 A | 1/1993 | Chiou |
| 5,184,359 A | 2/1993 | Tsukamura et al. |
| 5,186,431 A | 2/1993 | Tamari |
| 5,186,805 A | 2/1993 | Gross et al. |
| 5,190,522 A | 3/1993 | Wojcicki et al. |
| 5,191,719 A | 3/1993 | Kitt |
| 5,192,264 A | 3/1993 | Fossel |
| 5,192,272 A | 3/1993 | Faure |
| 5,197,322 A | 3/1993 | Indravudh |
| 5,203,506 A | 4/1993 | Gross et al. |
| 5,207,642 A | 5/1993 | Orkin et al. |
| 5,207,645 A | 5/1993 | Ross et al. |
| 5,207,666 A | 5/1993 | Idriss et al. |
| 5,209,265 A | 5/1993 | Taguri et al. |
| 5,215,450 A | 6/1993 | Tamari |
| 5,217,440 A | 6/1993 | Frassica |
| 5,217,442 A | 6/1993 | Davis |
| 5,218,987 A | 6/1993 | Heil |
| 5,220,515 A | 6/1993 | Freerks et al. |
| 5,228,291 A | 6/1993 | Meyering |
| 5,228,842 A | 6/1993 | Guebeli et al. |
| 5,226,446 A | 7/1993 | Cooper |
| 5,231,616 A | 7/1993 | Oliver et al. |
| 5,188,258 A | 8/1993 | Iwashita |
| 5,232,437 A | 8/1993 | Lysaght et al. |
| 5,232,449 A | 8/1993 | Stern et al. |
| 5,240,603 A | 8/1993 | Frank et al. |
| 5,241,935 A | 9/1993 | Beck et al. |
| 5,242,406 A | 9/1993 | Gross et al. |
| 5,242,408 A | 9/1993 | Jhuboo et al. |
| 5,243,983 A | 9/1993 | Tarr et al. |
| 5,246,147 A | 9/1993 | Gross |
| 5,247,434 A | 9/1993 | Peterson et al. |
| 5,254,096 A | 10/1993 | Rondelet et al. |
| 5,256,157 A | 10/1993 | Samiotes et al. |
| 5,257,971 A | 11/1993 | Lord et al. |
| 5,257,980 A | 11/1993 | Van Antwerp et al. |
| 5,259,399 A | 11/1993 | Brown |
| 5,259,557 A * | 11/1993 | Spriggs ............... B67D 7/423 222/129 |
| 5,259,732 A | 11/1993 | Stern |
| 5,261,459 A | 11/1993 | Atkinson et al. |
| 5,261,884 A | 11/1993 | Stern et al. |
| 5,266,265 A | 11/1993 | Raible |
| 5,270,005 A | 12/1993 | Raible |
| 5,271,724 A | 12/1993 | vanLintel |
| 5,272,294 A | 12/1993 | Charboneau et al. |
| 5,272,909 A | 12/1993 | Nguyen et al. |
| 5,273,406 A | 12/1993 | Feygin |
| 5,273,518 A | 12/1993 | Lee et al. |
| 5,278,142 A | 1/1994 | Chiou |
| 5,279,543 A | 1/1994 | Glickfeld et al. |
| 5,279,556 A | 1/1994 | Goi et al. |
| 5,279,585 A | 1/1994 | Balkwill |
| 5,279,586 A | 1/1994 | Balkwell |
| 5,290,684 A | 3/1994 | Kelly |
| 5,291,086 A | 3/1994 | Shekalim |
| 5,294,133 A | 3/1994 | Dutta |
| 5,295,796 A | 3/1994 | Goto et al. |
| 5,295,966 A | 3/1994 | Stern et al. |
| 5,295,967 A | 3/1994 | Rondelet et al. |
| 5,295,976 A | 3/1994 | Harris |
| 5,304,126 A | 4/1994 | Epstein et al. |
| 5,304,163 A | 4/1994 | Bonnici et al. |
| 5,308,340 A | 5/1994 | Harris |
| 5,312,233 A | 5/1994 | Tanny et al. |
| 5,320,250 A | 6/1994 | La et al. |
| 5,321,392 A | 6/1994 | Skakoon et al. |
| 5,322,418 A | 6/1994 | Comer |
| 5,322,620 A | 6/1994 | Brown et al. |
| 5,322,626 A | 6/1994 | Frank et al. |
| 5,327,777 A | 7/1994 | Kaye et al. |
| 5,328,460 A | 7/1994 | Lord et al. |
| 5,328,464 A | 7/1994 | Kriesel et al. |
| 5,303,843 A | 8/1994 | Zink et al. |
| 5,334,144 A | 8/1994 | Alchas et al. |
| 5,334,162 A | 8/1994 | Harris |
| 5,335,705 A | 8/1994 | Morishita et al. |
| 5,335,852 A | 8/1994 | Muntean et al. |
| 5,336,051 A | 8/1994 | Tamari |
| 5,336,174 A | 8/1994 | Daoud et al. |
| 5,336,180 A | 8/1994 | Kriesel et al. |
| 5,336,188 A | 8/1994 | Kriesel |
| 5,338,157 A | 8/1994 | Blomquist |
| 5,339,393 A | 8/1994 | Duffy et al. |
| 5,339,865 A | 8/1994 | Asghar et al. |
| 5,341,783 A | 8/1994 | Beck et al. |
| 5,342,180 A | 8/1994 | Daoud |
| 5,345,488 A | 9/1994 | Skipper et al. |
| 5,348,197 A | 9/1994 | Mizzi et al. |
| 5,348,548 A | 9/1994 | Meyer et al. |
| 5,349,933 A | 9/1994 | Hasegawa et al. |
| 5,350,224 A | 9/1994 | Nell et al. |
| 5,345,273 A | 10/1994 | Hagen |
| 5,352,201 A | 10/1994 | Jemmott |
| 5,354,273 A | 10/1994 | Hagen |
| 5,356,375 A | 10/1994 | Higley et al. |
| 5,356,378 A | 10/1994 | Doan |
| 5,356,379 A | 10/1994 | Vaillancourt |
| 5,356,632 A | 10/1994 | Gross et al. |
| 5,358,489 A | 10/1994 | Wyrick |
| 5,358,635 A | 10/1994 | Frank et al. |
| 5,360,062 A | 11/1994 | White |
| 5,360,734 A | 11/1994 | Chapman et al. |
| 5,362,213 A | 11/1994 | Komatsu et al. |
| 5,362,307 A | 11/1994 | Guy et al. |
| 5,364,242 A | 11/1994 | Olsen |
| 5,364,387 A | 11/1994 | Sweeny |
| 5,366,904 A | 11/1994 | Quereshi et al. |
| 5,367,910 A | 11/1994 | Woodward |
| 5,368,555 A | 11/1994 | Sussman et al. |
| 5,368,562 A | 11/1994 | Blomquist et al. |
| 5,369,976 A | 12/1994 | Ratton |
| 5,370,622 A | 12/1994 | Livingston et al. |
| 5,370,870 A | 12/1994 | Wong |
| 5,373,865 A | 12/1994 | Jung et al. |
| 5,376,070 A | 12/1994 | Purvis et al. |
| 5,381,823 A | 1/1995 | Dibartolo |
| 5,384,709 A | 1/1995 | Seder et al. |
| 5,387,192 A | 2/1995 | Glantz et al. |
| 5,387,327 A | 2/1995 | Khan |
| 5,388,453 A | 2/1995 | Ratton et al. |
| 5,389,071 A | 2/1995 | Kawahara et al. |
| 5,389,078 A | 2/1995 | Zalesky et al. |
| 5,389,091 A | 2/1995 | Moorehead |
| 5,390,671 A | 2/1995 | Lord et al. |
| 5,391,250 A | 2/1995 | Cheney, II et al. |
| 5,395,320 A | 3/1995 | Padda et al. |
| 5,395,324 A | 3/1995 | Hinrichs |
| 5,395,326 A | 3/1995 | Haber et al. |
| 5,399,166 A | 3/1995 | Laing |
| 5,403,551 A | 4/1995 | Galloway et al. |
| 5,407,444 A | 4/1995 | Kroll |
| 5,410,908 A | 5/1995 | Erichsen |
| 5,411,685 A | 5/1995 | Burgis |
| 5,415,024 A | 5/1995 | Proffitt et al. |
| 5,418,154 A | 5/1995 | Aebischer et al. |
| 5,419,770 A | 5/1995 | Crass et al. |
| 5,421,208 A | 6/1995 | Packard et al. |
| 5,423,743 A | 6/1995 | Buttrefield |

(56) References Cited

U.S. PATENT DOCUMENTS

| | | |
|---|---|---|
| 5,425,374 A | 6/1995 | Ueda et al. |
| 5,425,706 A | 6/1995 | Gross et al. |
| 5,425,742 A | 6/1995 | Joy |
| 5,427,870 A | 6/1995 | Joshi et al. |
| 5,431,208 A | 6/1995 | Packard et al. |
| 5,429,483 A | 7/1995 | Tamari |
| 5,429,601 A | 7/1995 | Conley et al. |
| 5,431,171 A | 7/1995 | Harrison et al. |
| 5,433,710 A | 7/1995 | VanAntwerp et al. |
| 5,435,465 A | 7/1995 | El-Amin |
| 5,435,697 A | 7/1995 | Guebeli et al. |
| 5,435,797 A | 7/1995 | Harris |
| 5,438,510 A | 8/1995 | Bryant et al. |
| 5,441,027 A | 8/1995 | Buchanon et al. |
| 5,442,948 A | 8/1995 | Cowing |
| 5,442,950 A | 8/1995 | Unalmiser et al. |
| 5,443,450 A | 8/1995 | Kratoska |
| 5,445,506 A | 8/1995 | Afflerbaugh et al. |
| 5,445,616 A | 8/1995 | Kratoska et al. |
| 5,447,509 A | 9/1995 | Mills et al. |
| 5,447,863 A | 9/1995 | Langley |
| 5,448,034 A | 9/1995 | Skipper et al. |
| 5,448,978 A | 9/1995 | Hasegawa et al. |
| 5,450,750 A | 9/1995 | Abler |
| 5,454,922 A | 10/1995 | Joshi et al. |
| 5,458,469 A | 10/1995 | Hauser |
| 5,460,030 A | 10/1995 | Blosxom et al. |
| 5,460,605 A | 10/1995 | tuttle et al. |
| 5,460,618 A | 10/1995 | Harreld |
| 5,460,945 A | 10/1995 | Springer et al. |
| 5,462,417 A | 10/1995 | Chapman |
| 5,462,525 A | 10/1995 | Srisathapat et al. |
| 5,462,535 A | 10/1995 | Bonnichsen et al. |
| 5,464,392 A | 11/1995 | Epstein et al. |
| 5,464,398 A | 11/1995 | Haindl |
| 5,466,218 A | 11/1995 | Srisathapat et al. |
| 5,466,229 A | 11/1995 | Elson et al. |
| 5,469,846 A | 11/1995 | Khan |
| 5,470,318 A | 11/1995 | Griffith, III et al. |
| 5,472,577 A | 12/1995 | Porter et al. |
| 5,476,444 A | 12/1995 | Keeling et al. |
| 5,476,449 A | 12/1995 | Richmond |
| 5,476,460 A | 12/1995 | Montalvo |
| 5,478,316 A | 12/1995 | Bitdinger et al. |
| 5,478,751 A | 12/1995 | Oosta et al. |
| 5,480,294 A | 1/1996 | Di Perna et al. |
| 5,480,381 A | 1/1996 | Weston |
| 5,482,446 A | 1/1996 | Williamson et al. |
| 5,482,745 A | 1/1996 | Cuellar et al. |
| 5,483,930 A | 1/1996 | Moriya et al. |
| 5,485,408 A | 1/1996 | Blomquist |
| 5,487,528 A | 1/1996 | Richmond |
| 5,568,806 A | 1/1996 | Cheney, II et al. |
| 5,489,265 A | 2/1996 | Montalvo et al. |
| 5,492,534 A | 2/1996 | Athayde et al. |
| 5,494,578 A | 2/1996 | Brown et al. |
| 5,510,336 A | 2/1996 | Saven et al. |
| 5,497,772 A | 3/1996 | Schulman et al. |
| 5,498,421 A | 3/1996 | Grinstaff et al. |
| 5,503,538 A | 4/1996 | Wiernicki et al. |
| 5,505,709 A | 4/1996 | Minimed |
| 5,505,777 A | 4/1996 | Ciardella et al. |
| 5,509,294 A | 4/1996 | Gowing |
| 5,514,103 A | 5/1996 | Srisathapat et al. |
| 5,518,730 A | 5/1996 | Fuisz |
| 5,522,798 A | 6/1996 | Johnson et al. |
| 5,526,675 A | 6/1996 | Ratton |
| 5,527,288 A | 6/1996 | Gross et al. |
| 5,527,307 A | 6/1996 | Srisathapat et al. |
| 5,527,704 A | 6/1996 | Wolf, Jr. et al. |
| 5,531,697 A | 7/1996 | Olsen et al. |
| 5,533,876 A | 7/1996 | Nelson, II |
| 5,533,981 A | 7/1996 | Mandro et al. |
| 5,536,249 A | 7/1996 | Castellano et al. |
| 5,538,002 A | 7/1996 | Boussignac et al. |
| 5,538,043 A | 7/1996 | Salazar |
| 5,538,399 A | 7/1996 | Johnson |
| 5,540,562 A | 7/1996 | Giter |
| 5,544,519 A | 8/1996 | Hammarberg et al. |
| 5,545,140 A | 8/1996 | Conero et al. |
| 5,545,252 A | 8/1996 | Hinshaw et al. |
| 5,549,458 A | 8/1996 | Chapman et al. |
| 5,551,391 A | 9/1996 | Beck et al. |
| 5,551,850 A | 9/1996 | Williamson et al. |
| 5,554,177 A | 9/1996 | Kieval et al. |
| 5,556,421 A | 9/1996 | Prutchi et al. |
| 5,558,638 A | 9/1996 | Evers et al. |
| 5,562,079 A | 10/1996 | Gray, Jr. |
| 5,562,618 A | 10/1996 | Cai et al. |
| 5,563,347 A | 10/1996 | Martin et al. |
| 5,564,915 A | 10/1996 | Johnson |
| 5,566,865 A | 10/1996 | Jouillat et al. |
| 5,567,136 A | 10/1996 | Johnson |
| 5,567,287 A | 10/1996 | Joshi et al. |
| 5,568,038 A | 10/1996 | Tatsumi |
| 5,568,884 A | 10/1996 | Bruna |
| 5,569,186 A | 10/1996 | Lord et al. |
| 5,584,815 A | 10/1996 | Pawelka et al. |
| 5,575,310 A | 11/1996 | Kamen et al. |
| 5,575,632 A | 11/1996 | Morris et al. |
| 5,575,770 A | 11/1996 | Melsky et al. |
| 5,578,005 A | 11/1996 | Sancoff et al. |
| 5,578,014 A | 11/1996 | Erez et al. |
| 5,578,832 A | 11/1996 | Trulson et al. |
| 5,582,168 A | 12/1996 | Samuels et al. |
| 5,584,667 A | 12/1996 | Davis |
| 5,586,553 A | 12/1996 | Halili et al. |
| 5,586,727 A | 12/1996 | Shekalim |
| 5,590,648 A | 1/1997 | Mitchell et al. |
| 5,593,552 A | 1/1997 | Joshi et al. |
| 5,602,040 A | 2/1997 | May et al. |
| 5,603,729 A | 2/1997 | Brown et al. |
| 5,605,152 A | 2/1997 | Slate et al. |
| 5,605,701 A | 2/1997 | Bymaster et al. |
| 5,606,131 A | 2/1997 | Pope |
| 5,607,418 A | 3/1997 | Arzbaecher |
| 5,613,945 A | 3/1997 | Cai et al. |
| 5,615,671 A | 4/1997 | Schoonen et al. |
| 5,616,123 A | 4/1997 | Cheikh |
| 5,616,132 A | 4/1997 | Newman |
| 5,617,650 A | 4/1997 | Grim |
| 5,621,797 A | 4/1997 | Rosen |
| RE35,501 E | 5/1997 | Ross et al. |
| 5,626,566 A | 5/1997 | Petersen et al. |
| 5,628,324 A | 5/1997 | Sarbach |
| 5,628,349 A | 5/1997 | Diggins et al. |
| 5,628,624 A | 5/1997 | Nelson, II |
| 5,628,922 A | 5/1997 | Chen |
| 5,634,491 A | 6/1997 | Benedict |
| 5,634,779 A | 6/1997 | Eysymontt |
| 5,634,896 A | 6/1997 | Bryant et al. |
| 5,637,092 A | 6/1997 | Shaw |
| 5,637,095 A | 6/1997 | Nason et al. |
| 5,639,220 A | 6/1997 | Hawakawa |
| 5,639,441 A | 6/1997 | Sievers et al. |
| 5,639,473 A | 6/1997 | Grinstaff et al. |
| 5,641,405 A | 6/1997 | Keshaviah et al. |
| 5,643,773 A | 7/1997 | Aebisher et al. |
| 5,645,526 A | 7/1997 | Flower |
| 5,647,853 A | 7/1997 | Feldmann et al. |
| 5,647,854 A | 7/1997 | Olsen et al. |
| 5,651,980 A | 7/1997 | Lanza et al. |
| 5,656,032 A | 8/1997 | Kriesel et al. |
| 5,656,501 A | 8/1997 | Yedgar et al. |
| 5,656,503 A | 8/1997 | May et al. |
| 5,658,250 A | 8/1997 | Blomquist |
| 5,658,252 A | 8/1997 | Johnson |
| 5,659,126 A | 8/1997 | Farber |
| 5,660,150 A | 8/1997 | Anderson et al. |
| 5,660,163 A | 8/1997 | Schulman et al. |
| 5,665,065 A | 9/1997 | Colman et al. |
| 5,665,070 A | 9/1997 | McPhee |
| 5,669,877 A | 9/1997 | Blomquist |
| 5,671,874 A | 9/1997 | Behar et al. |

(56) References Cited

U.S. PATENT DOCUMENTS

| | | | |
|---|---|---|---|
| 5,676,651 A | 10/1997 | Larson, Jr. et al. |
| 5,681,285 A | 10/1997 | Ford et al. |
| 5,681,435 A | 10/1997 | Joshi et al. |
| 5,685,844 A | 11/1997 | Marttila |
| 5,688,113 A | 11/1997 | Bareiss et al. |
| 5,688,225 A | 11/1997 | Walker |
| 5,688,232 A | 11/1997 | Flower |
| 5,693,018 A | 12/1997 | Kriesel et al. |
| 5,694,961 A | 12/1997 | Begemann et al. |
| 5,695,464 A | 12/1997 | Viallet |
| 5,695,472 A | 12/1997 | Wyrick |
| 5,695,473 A | 12/1997 | Olsen |
| 5,700,244 A | 12/1997 | Kriesel |
| 5,702,384 A | 12/1997 | Umeyama et al. |
| 5,704,366 A | 1/1998 | Tacklind et al. |
| 5,704,520 A | 1/1998 | Gross |
| 5,707,212 A | 1/1998 | Matthews |
| 5,707,361 A | 1/1998 | Slettenmark |
| 5,711,989 A | 1/1998 | Ciardella et al. |
| 5,712,795 A | 1/1998 | Layman et al. |
| 5,713,856 A | 2/1998 | Eggers et al. |
| 5,713,858 A | 2/1998 | Heruth et al. |
| 5,718,562 A | 2/1998 | Lawless et al. |
| 5,719,761 A | 2/1998 | Gatti et al. |
| 5,720,241 A | 2/1998 | Gail |
| 5,720,921 A | 2/1998 | Mersol |
| 5,722,367 A | 3/1998 | Izadorek |
| 5,728,396 A | 3/1998 | Peery et al. |
| 5,730,149 A | 3/1998 | Nayakama et al. |
| 5,735,818 A | 4/1998 | Kriesel et al. |
| 5,738,650 A | 4/1998 | Gregg |
| 5,740,718 A | 4/1998 | Rathweg |
| 5,741,211 A | 4/1998 | Renirie et al. |
| 5,741,242 A | 4/1998 | Kriesel et al. |
| 5,743,291 A | 4/1998 | Nehm et al. |
| 5,743,873 A | 4/1998 | Cai et al. |
| 5,746,733 A | 5/1998 | Capaccio et al. |
| 5,755,683 A | 5/1998 | Houle et al. |
| 5,755,696 A | 5/1998 | Caizza |
| 5,759,018 A | 6/1998 | Thanscheidt |
| 5,759,199 A | 6/1998 | Snell et al. |
| 5,763,267 A | 6/1998 | Kurjan et al. |
| 5,763,398 A | 6/1998 | Bengtsson |
| 5,765,464 A | 6/1998 | Morita |
| 5,765,729 A | 6/1998 | Miller et al. |
| 5,769,615 A | 6/1998 | Giter |
| 5,770,149 A | 6/1998 | Raible |
| 5,770,160 A | 6/1998 | Smith et al. |
| 5,771,770 A | 6/1998 | Muller |
| 5,772,409 A | 6/1998 | Johnson |
| 5,772,635 A | 6/1998 | Dastur et al. |
| 5,782,931 A | 6/1998 | Yang et al. |
| 5,785,681 A | 7/1998 | Indravudh |
| 5,785,688 A | 7/1998 | Joshi et al. |
| 5,788,642 A | 8/1998 | Hamatake et al. |
| 5,788,669 A | 8/1998 | Peterson |
| 5,788,671 A | 8/1998 | Johnson |
| 5,788,682 A | 8/1998 | Maget |
| 5,792,603 A | 8/1998 | Dunkelman et al. |
| 5,794,505 A | 8/1998 | Fischer et al. |
| 5,794,515 A | 8/1998 | Bethke |
| 5,795,327 A | 8/1998 | Wilson et al. |
| 5,797,867 A | 8/1998 | Guererra et al. |
| 5,798,114 A | 8/1998 | Elsberry et al. |
| 5,730,723 A | 9/1998 | Castellano et al. |
| 5,800,387 A | 9/1998 | Duffy et al. |
| 5,800,420 A | 9/1998 | Gross et al. |
| 5,803,319 A | 9/1998 | Smith et al. |
| 5,803,917 A | 9/1998 | Butterfield et al. |
| 5,807,315 A | 9/1998 | Van Antwerp et al. |
| 5,807,335 A | 9/1998 | Kriesel et al. |
| 5,807,336 A | 9/1998 | Russo et al. |
| 5,807,374 A | 9/1998 | Caizza et al. |
| 5,807,375 A | 9/1998 | Gross et al. |
| 5,810,737 A | 9/1998 | Dardik |
| 5,810,771 A | 9/1998 | Blomquist |
| 5,810,783 A | 9/1998 | Claro |
| 5,814,020 A | 9/1998 | Gross |
| 5,814,100 A | 9/1998 | Carpentier et al. |
| 5,820,587 A | 10/1998 | Place |
| 5,820,589 A | 10/1998 | Torgerson et al. |
| 5,820,622 A | 10/1998 | Gross et al. |
| 5,822,715 A | 10/1998 | Worthington et al. |
| 5,823,388 A | 10/1998 | Green |
| 5,823,746 A | 10/1998 | Johnson |
| 5,823,998 A | 10/1998 | Yamagata |
| 5,826,621 A | 10/1998 | Jemmott |
| 5,830,175 A | 11/1998 | Flower |
| 5,830,187 A | 11/1998 | Kriesel et al. |
| 5,832,972 A * | 11/1998 | Thomas .................. B67D 7/02 137/888 |
| 5,837,220 A | 11/1998 | Blake et al. |
| 5,837,444 A | 11/1998 | Shah |
| 5,840,069 A | 11/1998 | Robinson |
| 5,840,071 A | 11/1998 | Kriesel et al. |
| 5,840,770 A | 11/1998 | Hill |
| 5,848,593 A | 12/1998 | McGrady et al. |
| 5,848,880 A | 12/1998 | Helmig |
| 5,848,990 A | 12/1998 | Cirelli et al. |
| 5,848,991 A | 12/1998 | Gross et al. |
| 5,849,031 A | 12/1998 | Martinez et al. |
| 5,849,737 A | 12/1998 | Chaplan et al. |
| 5,851,197 A | 12/1998 | Marano et al. |
| 5,851,198 A | 12/1998 | Castellano et al. |
| 5,851,549 A | 12/1998 | Svec |
| 5,851,985 A | 12/1998 | Tepic et al. |
| 5,853,386 A | 12/1998 | Davis et al. |
| 5,854,074 A | 12/1998 | Charlton et al. |
| 5,854,719 A | 12/1998 | Ginosar et al. |
| 5,858,001 A | 1/1999 | Tsals et al. |
| 5,858,201 A | 1/1999 | Atsuka et al. |
| 5,858,388 A | 1/1999 | Grossman et al. |
| 5,858,393 A | 1/1999 | Bymaster et al. |
| 5,859,365 A | 1/1999 | Kataoka et al. |
| 5,860,957 A | 1/1999 | Jacobson et al. |
| 5,863,187 A | 1/1999 | Bensley et al. |
| 5,865,603 A | 2/1999 | Francart, Jr. |
| 5,871,125 A | 2/1999 | Gross |
| 5,871,515 A | 2/1999 | Wiklund et al. |
| 5,873,857 A | 2/1999 | Kriesel |
| 5,876,370 A | 2/1999 | Blomquist |
| 5,876,189 A | 3/1999 | Lukas et al. |
| 5,876,368 A | 3/1999 | Flower |
| 5,877,146 A | 3/1999 | McKenzie et al. |
| 5,877,216 A | 3/1999 | Place et al. |
| 5,878,992 A | 3/1999 | Edwards et al. |
| 5,879,143 A | 3/1999 | Cote et al. |
| 5,879,144 A | 3/1999 | Johnson |
| 5,880,101 A | 3/1999 | Stankov |
| 5,882,494 A | 3/1999 | Van Antwerp et al. |
| 5,883,138 A | 3/1999 | Hershkowitz et al. |
| 5,885,211 A | 3/1999 | Eppstein et al. |
| 5,885,250 A | 3/1999 | Kriesel et al. |
| 5,885,614 A | 3/1999 | Hirsch |
| 5,886,056 A | 3/1999 | Hershkowitz et al. |
| 5,887,793 A | 3/1999 | Kieffer |
| 5,890,413 A | 4/1999 | Bayer et al. |
| 5,891,097 A | 4/1999 | Saito et al. |
| 5,893,708 A | 4/1999 | Nelson, II |
| 5,894,992 A | 4/1999 | Liu et al. |
| 5,895,369 A | 4/1999 | Flower |
| 5,897,530 A | 4/1999 | Jackson |
| 5,902,336 A | 5/1999 | Mishkin |
| 5,903,710 A | 5/1999 | Wefler et al. |
| 5,912,005 A | 6/1999 | Lanza et al. |
| 5,916,191 A | 6/1999 | Plunkett et al. |
| 5,919,156 A | 6/1999 | Stropkay et al. |
| 5,919,209 A | 6/1999 | Schouten |
| 5,919,216 A | 6/1999 | Houben et al. |
| 5,924,456 A | 6/1999 | Simon |
| 5,925,629 A | 6/1999 | Place |
| 5,928,194 A | 6/1999 | Maget |
| 5,928,281 A | 6/1999 | Huynh et al. |
| 5,924,448 A | 7/1999 | West |

(56) References Cited

U.S. PATENT DOCUMENTS

| | | |
|---|---|---|
| 5,928,196 A | 7/1999 | Johnson et al. |
| 5,928,201 A | 7/1999 | Poulsen et al. |
| 5,931,814 A | 8/1999 | Alex et al. |
| 5,933,287 A | 8/1999 | Muller |
| 5,935,099 A | 8/1999 | Peeterson et al. |
| 5,935,106 A | 8/1999 | Olsen |
| 5,935,168 A | 8/1999 | Yang et al. |
| 5,935,598 A | 8/1999 | Sage et al. |
| 5,938,636 A | 8/1999 | Kramer et al. |
| 5,938,640 A | 8/1999 | Maget |
| 5,938,642 A | 8/1999 | Burroughs et al. |
| 5,941,846 A | 8/1999 | Duffy et al. |
| 5,950,879 A | 8/1999 | Ritsche |
| 5,948,367 A | 9/1999 | Gmeiner et al. |
| 5,951,521 A | 9/1999 | Mastrototaro et al. |
| 5,951,523 A | 9/1999 | Osterlund et al. |
| 5,954,485 A | 9/1999 | Johnson et al. |
| 5,954,643 A | 9/1999 | Van Antwerp et al. |
| 5,954,685 A | 9/1999 | Tierney |
| 5,954,696 A | 9/1999 | Ryan |
| 5,954,697 A | 9/1999 | Srisathapat et al. |
| 5,954,752 A | 9/1999 | Mongeon et al. |
| 5,957,861 A | 9/1999 | Combs et al. |
| 5,957,885 A | 9/1999 | Bollish et al. |
| 5,957,889 A | 9/1999 | Poulson et al. |
| 5,957,890 A | 9/1999 | Mann et al. |
| 5,957,895 A | 9/1999 | Sage et al. |
| 5,958,760 A | 9/1999 | Freeman |
| 5,960,403 A | 9/1999 | Brown |
| 5,961,305 A | 10/1999 | Eek et al. |
| 5,961,483 A | 10/1999 | Sage et al. |
| 5,962,566 A | 10/1999 | Grandfilis et al. |
| 5,962,794 A | 10/1999 | Kriesel et al. |
| 5,964,377 A | 10/1999 | Demarest et al. |
| 5,964,724 A | 10/1999 | Rivera et al. |
| 5,971,722 A | 10/1999 | Maget et al. |
| 5,973,012 A | 10/1999 | Behrmann et al. |
| 5,976,109 A | 11/1999 | Heruth |
| 5,980,489 A | 11/1999 | Kriesel |
| 5,980,596 A | 11/1999 | Hershkowitz et al. |
| 5,983,976 A | 11/1999 | Kono |
| 5,984,894 A | 11/1999 | Poulson et al. |
| 5,984,897 A | 11/1999 | Peterson et al. |
| 5,984,906 A | 11/1999 | Bonnichsen et al. |
| 5,985,305 A | 11/1999 | Peery et al. |
| 5,985,894 A | 11/1999 | Poulsen et al. |
| 5,988,165 A | 11/1999 | Richey et al. |
| 5,988,851 A | 11/1999 | Gent |
| 5,988,998 A | 11/1999 | Glover |
| 5,989,216 A | 11/1999 | Johnson et al. |
| 5,989,222 A | 11/1999 | Cole et al. |
| 5,989,238 A | 11/1999 | Ginsburg |
| 5,989,409 A | 11/1999 | Kurnik et al. |
| 5,992,695 A | 11/1999 | Start |
| 5,993,421 A | 11/1999 | Kriesel |
| 5,993,425 A | 11/1999 | Kriesel |
| 5,995,860 A | 11/1999 | Sun et al. |
| 5,997,475 A | 12/1999 | Bortz |
| 5,997,501 A | 12/1999 | Gross et al. |
| 5,997,518 A | 12/1999 | Laibovitz et al. |
| 6,001,089 A | 12/1999 | Burroughs et al. |
| 6,001,585 A | 12/1999 | Gramer |
| 6,003,566 A | 12/1999 | Thibault et al. |
| 6,003,736 A | 12/1999 | Ljunggren |
| 6,006,800 A | 12/1999 | Nakano |
| 6,007,314 A | 12/1999 | Nelson, II |
| 6,007,518 A | 12/1999 | Kriesel et al. |
| 6,012,034 A | 1/2000 | Hamparian et al. |
| 6,012,492 A | 1/2000 | Kozyuk |
| 6,013,020 A | 1/2000 | Meloul et al. |
| 6,016,044 A | 1/2000 | Holdaway |
| 6,017,318 A | 1/2000 | Gauthier |
| 6,017,545 A | 1/2000 | Modi |
| 6,019,747 A | 2/2000 | McPhee |
| 6,023,629 A | 2/2000 | Tamada |
| 6,023,641 A | 2/2000 | Thompson |
| 6,024,009 A | 2/2000 | Morita |
| 6,024,539 A | 2/2000 | Blomquist |
| 6,024,699 A | 2/2000 | Surwit |
| 6,030,358 A | 2/2000 | Odland |
| 6,030,363 A | 2/2000 | Kriesel |
| 6,033,377 A | 3/2000 | Rasmussen et al. |
| 6,034,054 A | 3/2000 | DeFelippis et al. |
| 6,035,639 A | 3/2000 | Kolmanovsky |
| 6,037,346 A | 3/2000 | Doherty, Jr. et al. |
| 6,038,960 A | 3/2000 | Fukushima et al. |
| 6,040,834 A | 3/2000 | Jain et al. |
| 6,042,561 A | 3/2000 | Ash et al. |
| 6,045,537 A | 4/2000 | Klitmose |
| 6,048,337 A | 4/2000 | Svedman |
| 6,051,256 A | 4/2000 | Platz et al. |
| 6,053,887 A | 4/2000 | Levitas |
| 6,056,522 A | 5/2000 | Johnson |
| 6,056,718 A | 5/2000 | Funderburk et al. |
| 6,059,507 A | 5/2000 | Adams |
| 6,059,753 A | 5/2000 | Faust et al. |
| 6,062,022 A | 5/2000 | Folsom et al. |
| 6,062,531 A | 5/2000 | Rapp et al. |
| 6,063,053 A | 5/2000 | Castellano et al. |
| 6,063,059 A | 5/2000 | Kriesel |
| 6,065,279 A | 5/2000 | Kuromitsu et al. |
| 6,065,289 A | 5/2000 | Phillips |
| 6,065,941 A | 5/2000 | Gray et al. |
| 6,070,761 A | 6/2000 | Bloom et al. |
| 6,071,423 A | 6/2000 | Brown et al. |
| 6,073,048 A | 6/2000 | Kieval et al. |
| 6,074,359 A | 6/2000 | Keshaviah et al. |
| 6,077,055 A | 6/2000 | Vilks |
| 6,077,246 A | 6/2000 | Kullas et al. |
| 6,080,130 A | 6/2000 | Castellano et al. |
| 6,083,602 A | 7/2000 | Caldwell et al. |
| 6,083,710 A | 7/2000 | Heller et al. |
| 6,086,561 A | 7/2000 | Kriesel et al. |
| 6,086,562 A | 7/2000 | Jacobson et al. |
| 6,093,167 A | 7/2000 | Houben et al. |
| 6,093,172 A | 7/2000 | Funderburk et al. |
| 6,093,312 A | 7/2000 | Boulter |
| 6,095,134 A | 8/2000 | Sievers et al. |
| 6,096,216 A | 8/2000 | Shanbrom et al. |
| 6,099,293 A | 8/2000 | Kern et al. |
| 6,099,495 A | 8/2000 | Kinghorn et al. |
| 6,099,504 A | 8/2000 | Gross et al. |
| 6,102,127 A | 8/2000 | Pierce |
| 6,103,033 A | 8/2000 | Say et al. |
| 6,103,275 A | 8/2000 | Seitz et al. |
| 6,105,442 A | 8/2000 | Kriesel et al. |
| 6,106,477 A | 8/2000 | Miesel et al. |
| 6,109,896 A | 8/2000 | Schuller et al. |
| 6,110,148 A | 8/2000 | Brown et al. |
| 6,110,149 A | 8/2000 | Klitgaard et al. |
| 6,110,152 A | 8/2000 | Kovelman |
| 6,110,427 A | 8/2000 | Uffenheimer |
| RE36,871 E | 9/2000 | Epstein et al. |
| 6,113,782 A | 9/2000 | Leonard |
| 6,117,122 A | 9/2000 | Din et al. |
| 6,120,460 A | 9/2000 | Abreu |
| 6,122,536 A | 9/2000 | Sun et al. |
| 6,123,175 A | 9/2000 | Fett |
| 6,123,686 A | 9/2000 | Olsen et al. |
| 6,126,642 A | 10/2000 | Kriesel et al. |
| 6,126,956 A | 10/2000 | Grossman et al. |
| 6,127,363 A | 10/2000 | Doherty, Jr. et al. |
| 6,132,686 A | 10/2000 | Gallup et al. |
| 6,135,196 A | 10/2000 | Kono |
| 6,135,949 A | 10/2000 | Russo et al. |
| 6,135,978 A | 10/2000 | Houben et al. |
| D433,755 S | 11/2000 | Mastrotaro et al. |
| 6,142,939 A | 11/2000 | Eppstein et al. |
| 6,143,238 A | 11/2000 | Konishi et al. |
| 6,143,252 A | 11/2000 | Haxo, Jr. et al. |
| 6,144,866 A | 11/2000 | Miesel et al. |
| 6,144,869 A | 11/2000 | Berner et al. |
| 6,145,625 A | 11/2000 | Prokop et al. |
| 6,146,361 A | 11/2000 | DiBiasi et al. |

(56) References Cited

U.S. PATENT DOCUMENTS

| | | |
|---|---|---|
| 6,147,070 A | 11/2000 | Facchini |
| 6,147,109 A | 11/2000 | Liao et al. |
| 6,152,898 A | 11/2000 | Olsen |
| 6,155,748 A | 12/2000 | Allen et al. |
| 6,156,753 A | 12/2000 | Doherty, Jr. et al. |
| 6,158,431 A | 12/2000 | Poole |
| 6,158,965 A | 12/2000 | Butterfield et al. |
| 6,163,721 A | 12/2000 | Thompson |
| 6,164,924 A | 12/2000 | Gruett et al. |
| 6,165,155 A | 12/2000 | Jacobson et al. |
| 6,167,290 A | 12/2000 | Yang et al. |
| 6,168,575 B1 | 1/2001 | Soultanpour |
| 6,175,752 B1 | 1/2001 | Say et al. |
| 6,176,692 B1 | 1/2001 | Reinartz et al. |
| 6,178,996 B1 | 1/2001 | Suzuki |
| 6,179,583 B1 | 1/2001 | Weston |
| 6,180,416 B1 | 1/2001 | Kurnik et al. |
| 6,180,597 B1 | 1/2001 | Liao et al. |
| 6,185,460 B1 | 2/2001 | Thompson |
| 6,186,982 B1 | 2/2001 | Gross et al. |
| 6,190,359 B1 | 2/2001 | Heruth |
| 6,198,383 B1 | 3/2001 | Sekura et al. |
| 6,202,708 B1 | 3/2001 | Bynum |
| 6,205,961 B1 | 3/2001 | Bailey et al. |
| 6,210,135 B1 | 4/2001 | Rassin et al. |
| 6,210,361 B1 | 4/2001 | Kamen et al. |
| 6,210,368 B1 | 4/2001 | Rogers |
| 6,210,957 B1 | 4/2001 | Carpentier et al. |
| 6,211,147 B1 | 4/2001 | Unemori |
| 6,211,426 B1 | 4/2001 | Abrams |
| 6,212,948 B1 | 4/2001 | Ekdahl et al. |
| 6,213,120 B1 | 4/2001 | Block et al. |
| 6,213,408 B1 | 4/2001 | Shekalim |
| 6,217,826 B1 | 4/2001 | Reeder et al. |
| 6,218,666 B1 | 4/2001 | Lukica et al. |
| 6,221,378 B1 | 4/2001 | Modi |
| 6,223,080 B1 | 4/2001 | Thompson |
| 6,223,703 B1 | 5/2001 | Galvin |
| 6,223,746 B1 | 5/2001 | Jewett et al. |
| 6,224,347 B1 | 5/2001 | Clark et al. |
| 6,224,352 B1 | 5/2001 | Hauser et al. |
| 6,225,999 B1 | 5/2001 | Jain et al. |
| 6,227,818 B1 | 5/2001 | Falk et al. |
| 6,228,044 B1 | 5/2001 | Jensen et al. |
| 6,229,584 B1 | 5/2001 | Chuo et al. |
| 6,231,545 B1 | 5/2001 | Kriesel et al. |
| 6,231,882 B1 | 5/2001 | Modi |
| 6,233,471 B1 | 5/2001 | Berner et al. |
| 6,236,887 B1 | 5/2001 | Ben-Hamin et al. |
| 6,238,423 B1 | 5/2001 | Bardy |
| 6,241,704 B1 | 6/2001 | Peterson et al. |
| 6,241,743 B1 | 6/2001 | Levin et al. |
| 6,245,347 B1 | 6/2001 | Zhang et al. |
| 6,247,493 B1 | 6/2001 | Henderson |
| 6,248,067 B1 | 6/2001 | Causey, III et al. |
| 6,248,093 B1 | 6/2001 | Moberg |
| 6,248,280 B1 | 6/2001 | Kern et al. |
| 6,251,098 B1 | 6/2001 | Rake et al. |
| 6,251,293 B1 | 6/2001 | Snodgrass et al. |
| 6,251,932 B1 | 6/2001 | Reicht et al. |
| 6,254,355 B1 | 7/2001 | Gharib |
| 6,254,569 B1 | 7/2001 | O'Donnell |
| 6,254,576 B1 | 7/2001 | Shekalim |
| 6,254,586 B1 | 7/2001 | Mann et al. |
| 6,256,533 B1 | 7/2001 | Yuzhakov et al. |
| 6,257,178 B1 | 7/2001 | Laimbock |
| 6,257,191 B1 | 7/2001 | Kutlucinar |
| 6,261,272 B1 | 7/2001 | Gross et al. |
| 6,261,280 B1 | 7/2001 | Houbin et al. |
| 6,264,439 B1 | 7/2001 | Falk et al. |
| 6,264,680 B1 | 7/2001 | Ash et al. |
| 6,266,564 B1 | 7/2001 | Hill et al. |
| 6,267,564 B1 | 7/2001 | Rapheal |
| 6,269,340 B1 | 7/2001 | Ford et al. |
| 6,270,478 B1 | 8/2001 | Mernoe |
| 6,272,364 B1 | 8/2001 | Kurnik |
| 6,275,717 B1 | 8/2001 | Gross et al. |
| 6,276,434 B1 | 8/2001 | Kono |
| 6,277,095 B1 | 8/2001 | Kriesel et al. |
| 6,277,097 B1 | 8/2001 | Mikkelsen et al. |
| 6,277,819 B1 | 8/2001 | Efendic |
| 6,280,408 B1 | 8/2001 | Sipin |
| 6,280,409 B1 | 8/2001 | Sipin |
| 6,280,416 B1 | 8/2001 | Van Antwerp et al. |
| 6,283,197 B1 | 8/2001 | Kono |
| 6,283,680 B1 | 9/2001 | Vidal |
| 6,283,943 B1 | 9/2001 | Dy et al. |
| 6,283,944 B1 | 9/2001 | McMullen et al. |
| 6,283,949 B1 | 9/2001 | Roorda |
| 6,284,725 B1 | 9/2001 | Coolidge et al. |
| 6,288,518 B1 | 9/2001 | Yang et al. |
| 6,289,248 B1 | 9/2001 | Conley |
| 6,290,683 B1 | 9/2001 | Erez et al. |
| 6,293,159 B1 | 9/2001 | Kriesel et al. |
| 6,293,242 B1 | 9/2001 | Kutlucinar |
| 6,293,429 B2 | 9/2001 | Sadler et al. |
| 6,293,756 B1 | 9/2001 | Andersson |
| 6,294,550 B1 | 9/2001 | Place et al. |
| 6,296,456 B1 | 10/2001 | Thornelow et al. |
| 6,296,623 B2 | 10/2001 | Spinello |
| 6,298,254 B2 | 10/2001 | Tamada |
| 6,298,760 B1 | 10/2001 | Danby |
| 6,298,941 B1 | 10/2001 | Spadafora |
| 6,299,415 B1 | 10/2001 | Bahrton |
| 6,299,578 B1 | 10/2001 | Kurnik et al. |
| 6,302,107 B1 | 10/2001 | Richey et al. |
| 6,302,653 B1 | 10/2001 | Bryant et al. |
| 6,302,855 B1 | 10/2001 | Lav et al. |
| 6,304,911 B1 | 10/2001 | Brcich et al. |
| 6,306,420 B1 | 10/2001 | Cheikh |
| 6,306,841 B1 | 10/2001 | Place et al. |
| 6,309,351 B1 | 10/2001 | Kurnik et al. |
| 6,309,371 B1 | 10/2001 | Deboer et al. |
| 6,310,270 B1 | 10/2001 | Huang et al. |
| 6,312,409 B1 | 11/2001 | Gross |
| 6,314,317 B1 | 11/2001 | Willis |
| 6,315,769 B1 | 11/2001 | Peer et al. |
| 6,319,215 B1 | 11/2001 | Peer et al. |
| 6,319,245 B1 | 11/2001 | Berrigan |
| 6,323,022 B1 | 11/2001 | Chang et al. |
| 6,325,999 B1 | 12/2001 | Bellgrau et al. |
| 6,327,964 B1 | 12/2001 | Schuller et al. |
| 6,328,004 B1 | 12/2001 | Rynhart |
| 6,331,172 B1 | 12/2001 | Epstein et al. |
| 6,334,761 B1 | 1/2002 | Tai et al. |
| 6,338,942 B2 | 1/2002 | Kraus et al. |
| 6,340,357 B1 | 1/2002 | Poulsen et al. |
| 6,340,421 B1 | 1/2002 | Vachon et al. |
| 6,340,783 B1 | 1/2002 | Snow |
| 6,341,232 B1 | 1/2002 | Conn et al. |
| 6,342,037 B1 | 1/2002 | Roe et al. |
| 6,342,484 B1 | 1/2002 | Kulkarni et al. |
| 6,344,457 B1 | 2/2002 | Jeanpetit et al. |
| 6,346,095 B1 | 2/2002 | Gross et al. |
| 6,349,783 B1 | 2/2002 | Galbraith et al. |
| 6,350,589 B1 | 2/2002 | Morris et al. |
| 6,355,030 B1 | 3/2002 | Aldrich et al. |
| 6,358,225 B1 | 3/2002 | Butterfield |
| 6,358,519 B1 | 3/2002 | Waterman |
| 6,360,888 B1 | 3/2002 | McIvor et al. |
| 6,362,591 B1 | 3/2002 | Moberg |
| 6,364,865 B1 | 4/2002 | Lavi et al. |
| 6,365,185 B1 | 4/2002 | Ritchel et al. |
| 6,365,628 B1 | 4/2002 | Berge |
| 6,366,808 B1 | 4/2002 | Schroppel et al. |
| 6,368,272 B1 | 4/2002 | Porumbescu |
| 6,368,314 B1 | 4/2002 | Kipfer et al. |
| 6,371,732 B1 | 4/2002 | Moubayed et al. |
| 6,372,182 B1 | 4/2002 | Mauro et al. |
| 6,372,508 B1 | 4/2002 | Schinzer et al. |
| 6,374,683 B1 | 4/2002 | Hunicke-Smith et al. |
| 6,374,876 B2 | 4/2002 | Bynum |
| 6,375,638 B2 | 4/2002 | Nason et al. |
| 6,381,493 B1 | 4/2002 | Stadler et al. |

(56) References Cited

U.S. PATENT DOCUMENTS

| | | |
|---|---|---|
| 6,382,923 B1 | 5/2002 | gray |
| 6,393,318 B1 | 5/2002 | Conn et al. |
| 6,393,893 B1 | 5/2002 | Fetz et al. |
| 6,394,981 B2 | 5/2002 | Heruth |
| 6,395,292 B2 | 5/2002 | Peery et al. |
| 6,395,536 B2 | 5/2002 | Freeman |
| 6,397,199 B1 | 5/2002 | Goodwin, III |
| 6,398,718 B1 | 6/2002 | Yachia et al. |
| 6,398,760 B1 | 6/2002 | Danby |
| 6,399,024 B1 | 6/2002 | Bevirt et al. |
| 6,402,689 B1 | 6/2002 | Scarantino et al. |
| 6,406,455 B1 | 6/2002 | Willis et al. |
| 6,409,698 B1 | 6/2002 | Robinson |
| 6,412,273 B1 | 7/2002 | Rohs |
| 6,413,238 B1 | 7/2002 | Maget et al. |
| 6,413,254 B1 | 7/2002 | Hissong et al. |
| 6,415,961 B2 | 7/2002 | Bonnigue |
| 6,416,215 B1 | 7/2002 | Terentiev |
| 6,416,291 B1 | 7/2002 | Butterfield et al. |
| 6,416,293 B1 | 7/2002 | Bouchard et al. |
| 6,420,169 B1 | 7/2002 | Read et al. |
| 6,422,057 B1 | 7/2002 | Anderson |
| 6,422,256 B1 | 7/2002 | Balazy et al. |
| 6,423,029 B1 | 7/2002 | Elsberry |
| 6,423,035 B1 | 7/2002 | Das et al. |
| 6,423,344 B1 | 7/2002 | Platz et al. |
| 6,424,847 B1 | 7/2002 | Mastrototaro et al. |
| 6,425,740 B1 | 7/2002 | Jacobsen et al. |
| 6,425,878 B1 | 7/2002 | Shekalim |
| 6,427,088 B1 | 7/2002 | Bowman, IV et al. |
| 6,429,160 B1 | 7/2002 | Bloch |
| 6,428,491 B1 | 8/2002 | Weiss |
| 6,429,197 B1 | 8/2002 | Coolidge et al. |
| 6,429,230 B1 | 8/2002 | Cavazza |
| 6,429,232 B1 | 8/2002 | Kinsella et al. |
| 6,433,040 B1 | 8/2002 | Dellamary et al. |
| 6,436,072 B1 | 8/2002 | Kullas et al. |
| 6,436,078 B1 | 8/2002 | Svedman |
| 6,438,408 B1 | 8/2002 | Mulligan et al. |
| 6,438,414 B1 | 8/2002 | Conn et al. |
| 6,440,096 B1 | 8/2002 | Lastovich et al. |
| 6,441,036 B1 | 8/2002 | Berge |
| 6,442,433 B1 | 8/2002 | Linberg |
| 6,443,097 B1 | 9/2002 | Zohar et al. |
| 6,443,942 B2 | 9/2002 | Van Antwerp |
| 6,446,513 B1 | 9/2002 | Henderson |
| 6,447,443 B1 | 9/2002 | Keogh et al. |
| 6,447,446 B1 | 9/2002 | Smith et al. |
| 6,447,475 B1 | 9/2002 | Castellano et al. |
| 6,447,522 B2 | 9/2002 | Gambale et al. |
| 6,450,942 B1 | 9/2002 | Lapanashvili et al. |
| 6,450,953 B1 | 9/2002 | Place et al. |
| 6,454,707 B1 | 9/2002 | Casscells, III |
| 6,454,785 B2 | 9/2002 | De Hoyos Garza |
| 6,457,956 B1 | 10/2002 | Hauser et al. |
| 6,458,102 B1 | 10/2002 | Mann et al. |
| 6,458,109 B1 | 10/2002 | Henley et al. |
| 6,458,256 B1 | 10/2002 | Zhong |
| 6,458,762 B1 | 10/2002 | McKenzie et al. |
| 6,461,329 B1 | 10/2002 | Van Antwerp et al. |
| 6,461,331 B1 | 10/2002 | Van Antwerp |
| 6,461,334 B1 | 10/2002 | Buch-Rasmussen et al. |
| 6,461,828 B1 | 10/2002 | Stanton et al. |
| 6,463,794 B1 | 10/2002 | Moshe et al. |
| 6,464,667 B1 | 10/2002 | Kamen et al. |
| 6,467,267 B2 | 10/2002 | Kanazawa et al. |
| 6,468,200 B1 | 10/2002 | Fischi |
| 6,468,242 B1 | 10/2002 | Wilson et al. |
| 6,469,016 B1 | 10/2002 | Place et al. |
| 6,470,234 B1 | 10/2002 | McGrady |
| 6,471,496 B1 | 10/2002 | Merklein et al. |
| 6,471,689 B1 | 10/2002 | Joseph et al. |
| 6,471,855 B1 | 10/2002 | Odak et al. |
| 6,472,434 B1 | 10/2002 | Place et al. |
| 6,474,219 B2 | 11/2002 | Kitmose et al. |
| 6,475,180 B2 | 11/2002 | Peterson et al. |
| 6,475,750 B1 | 11/2002 | Han et al. |
| 6,477,774 B1 | 11/2002 | Marando et al. |
| 6,478,385 B1 | 11/2002 | Nishii et al. |
| 6,478,771 B1 | 11/2002 | Lavi et al. |
| 6,482,186 B1 | 11/2002 | Douglas et al. |
| 6,484,906 B2 | 11/2002 | Bonnigue |
| 6,485,263 B1 | 11/2002 | Bryant et al. |
| 6,485,452 B1 | 11/2002 | French et al. |
| 6,485,461 B1 | 11/2002 | Mason et al. |
| 6,485,463 B1 | 11/2002 | Yeh |
| 6,485,464 B1 | 11/2002 | Christenson et al. |
| 6,485,465 B2 | 11/2002 | Moberg et al. |
| 6,485,471 B1 | 11/2002 | Zivitz et al. |
| 6,488,652 B1 | 12/2002 | Weijand et al. |
| 6,488,697 B1 | 12/2002 | Ariura et al. |
| 6,489,346 B1 | 12/2002 | Phillips |
| 6,490,483 B2 | 12/2002 | Willis |
| 6,494,865 B1 | 12/2002 | Alchas |
| 6,500,150 B1 | 12/2002 | Gross et al. |
| 6,505,059 B1 | 1/2003 | Kollias et al. |
| 6,506,594 B1 | 1/2003 | Barany et al. |
| 6,508,788 B2 | 1/2003 | Preuthun |
| 6,511,435 B1 | 1/2003 | Bluth et al. |
| 6,512,949 B1 | 1/2003 | Combs et al. |
| 6,514,689 B2 | 2/2003 | Han et al. |
| 6,517,482 B1 | 2/2003 | Elden et al. |
| 6,520,936 B1 | 2/2003 | Mann |
| 6,520,938 B1 | 2/2003 | Funderburk et al. |
| 6,522,980 B1 | 2/2003 | Arnold |
| 6,583,111 B1 | 2/2003 | DiMarchi et al. |
| 6,530,900 B1 | 3/2003 | Daily et al. |
| 6,533,183 B2 | 3/2003 | Aasmul et al. |
| 6,535,714 B2 | 3/2003 | Melker et al. |
| 6,537,241 B1 | 3/2003 | Odland |
| 6,537,251 B2 | 3/2003 | Klitmose |
| 6,537,268 B1 | 3/2003 | Gibson et al. |
| 6,537,272 B2 | 3/2003 | Christopherson et al. |
| 6,540,006 B2 | 4/2003 | Kono |
| 6,540,161 B1 | 4/2003 | Gordon |
| 6,540,727 B2 | 4/2003 | Harper et al. |
| 6,540,996 B1 | 4/2003 | Zwaal et al. |
| 6,541,021 B1 | 4/2003 | Johnson et al. |
| 6,542,774 B2 | 4/2003 | Hill et al. |
| 6,542,775 B2 | 4/2003 | Ding et al. |
| 6,544,212 B2 | 4/2003 | Hill et al. |
| 6,544,229 B1 | 4/2003 | Danby et al. |
| 6,544,233 B1 | 4/2003 | Fukui et al. |
| 6,546,269 B1 | 4/2003 | Kurnik |
| 6,547,775 B1 | 4/2003 | Ding et al. |
| 6,550,245 B2 | 4/2003 | Nishii et al. |
| 6,551,276 B1 | 4/2003 | Mann et al. |
| 6,551,277 B1 | 4/2003 | Ford |
| 6,551,992 B1 | 4/2003 | DeFelippis et al. |
| 6,553,244 B2 | 4/2003 | Lesho et al. |
| 6,553,245 B1 | 4/2003 | Grace et al. |
| 6,554,798 B1 | 4/2003 | Mann et al. |
| 6,554,800 B1 | 4/2003 | Nezhadian et al. |
| 6,555,986 B2 | 4/2003 | Moberg |
| 6,557,454 B2 | 5/2003 | Miyazawa |
| 6,558,320 B1 | 5/2003 | Causey et al. |
| 6,558,351 B1 | 5/2003 | Steil et al. |
| 6,558,665 B1 | 5/2003 | Cohen et al. |
| 6,560,478 B1 | 5/2003 | Alfano et al. |
| 6,561,978 B1 | 5/2003 | Conn et al. |
| 6,562,001 B2 | 5/2003 | Lebel et al. |
| 6,562,011 B1 | 5/2003 | Buch-Rasmussen et al. |
| 6,564,093 B1 | 5/2003 | Ostrow et al. |
| 6,564,104 B2 | 5/2003 | Nelson et al. |
| 6,564,105 B2 | 5/2003 | Starkweather et al. |
| 6,565,802 B1 | 5/2003 | Hanley et al. |
| 6,565,872 B2 | 5/2003 | Wu et al. |
| 6,568,898 B2 | 5/2003 | Nishimura et al. |
| 6,568,922 B1 | 5/2003 | Winsel |
| 6,569,123 B2 | 5/2003 | Alchas et al. |
| 6,569,143 B2 | 5/2003 | Alchas et al. |
| 6,569,456 B2 | 5/2003 | Faour et al. |
| 6,571,128 B2 | 5/2003 | Lebel et al. |
| 6,558,345 B1 | 6/2003 | Houben et al. |

(56) References Cited

U.S. PATENT DOCUMENTS

| | | |
|---|---|---|
| 6,558,902 B1 | 6/2003 | Hillenkamp |
| 6,571,831 B1 | 6/2003 | Hart |
| 6,572,542 B1 | 6/2003 | Houben et al. |
| 6,572,566 B2 | 6/2003 | Effenhauser |
| 6,572,586 B1 | 6/2003 | Wojcik |
| 6,575,935 B1 | 6/2003 | Oliver et al. |
| 6,577,899 B2 | 6/2003 | Lebel et al. |
| 6,579,496 B1 | 6/2003 | Fausset et al. |
| 6,582,366 B1 | 6/2003 | Porumbescu |
| 6,582,393 B2 | 6/2003 | Sage, Jr. |
| 6,582,418 B1 | 6/2003 | Verbeek et al. |
| 6,585,644 B2 | 7/2003 | Lebel et al. |
| 6,585,695 B1 | 7/2003 | Adair et al. |
| 6,585,707 B2 | 7/2003 | Cabiri et al. |
| 6,587,705 B1 | 7/2003 | Kim et al. |
| 6,589,158 B2 | 7/2003 | Winkler |
| 6,589,229 B1 | 7/2003 | Connelly et al. |
| 6,592,544 B1 | 7/2003 | Mooney et al. |
| 6,592,571 B1 | 7/2003 | Verbeek et al. |
| 6,592,860 B1 | 7/2003 | Levy et al. |
| 6,592,904 B2 | 7/2003 | Platz et al. |
| 6,593,313 B2 | 7/2003 | Place et al. |
| 6,594,514 B2 | 7/2003 | Berner et al. |
| 6,594,634 B1 | 7/2003 | Hampton et al. |
| 6,595,756 B2 | 7/2003 | Gray et al. |
| 6,595,919 B2 | 7/2003 | Berner et al. |
| 6,595,948 B2 | 7/2003 | Suzuki et al. |
| 6,595,956 B1 | 7/2003 | Gross et al. |
| 6,599,281 B1 | 7/2003 | Struys et al. |
| 6,602,241 B2 | 8/2003 | Makower et al. |
| 6,604,908 B1 | 8/2003 | Bryant et al. |
| 6,605,072 B2 | 8/2003 | Struys et al. |
| 6,607,513 B1 | 8/2003 | Down et al. |
| 6,607,658 B1 | 8/2003 | Heller et al. |
| 6,607,739 B1 | 8/2003 | Wallo |
| 6,610,003 B1 | 8/2003 | Meloul et al. |
| 6,612,535 B1 | 9/2003 | Tai et al. |
| 6,613,019 B2 | 9/2003 | Munk |
| 6,616,196 B1 | 9/2003 | Weh et al. |
| 6,616,627 B2 | 9/2003 | Willis et al. |
| 6,618,603 B2 | 9/2003 | Varalli et al. |
| 6,620,140 B1 | 9/2003 | Metzger |
| 6,620,379 B1 | 9/2003 | Piuk et al. |
| 6,623,698 B2 | 9/2003 | Kuo |
| 6,625,479 B1 | 9/2003 | Weber et al. |
| 6,626,644 B2 | 9/2003 | Ozaki |
| 6,629,934 B2 | 10/2003 | Mault et al. |
| 6,629,938 B1 | 10/2003 | Engvall et al. |
| 6,629,949 B1 | 10/2003 | Douglas |
| 6,629,954 B1 | 10/2003 | Heruth |
| 6,634,939 B2 | 10/2003 | Johnson |
| 6,635,014 B2 | 10/2003 | Starkweather et al. |
| 6,635,048 B1 | 10/2003 | Ullestad et al. |
| 6,636,796 B2 | 10/2003 | Kolmanovsky et al. |
| 6,639,381 B2 | 10/2003 | Tamura et al. |
| 6,641,533 B2 | 11/2003 | Causey et al. |
| 6,641,562 B1 | 11/2003 | Peterson |
| 6,641,565 B1 | 11/2003 | Lavi et al. |
| 6,641,566 B2 | 11/2003 | Douglas et al. |
| 6,642,019 B1 | 11/2003 | Anderson et al. |
| 6,645,176 B1 | 11/2003 | Christenson et al. |
| 6,645,181 B1 | 11/2003 | Lavi et al. |
| 6,645,448 B2 | 11/2003 | Cho et al. |
| 6,648,821 B2 | 11/2003 | Lebel et al. |
| 6,648,859 B2 | 11/2003 | Bitdinger et al. |
| 6,648,861 B2 | 11/2003 | Platt et al. |
| 6,649,403 B1 | 11/2003 | McDevitt et al. |
| 6,650,919 B2 | 11/2003 | Edelberg et al. |
| 6,650,951 B1 | 11/2003 | Jones et al. |
| 6,651,546 B2 | 11/2003 | Sandlin |
| 6,652,493 B1 | 11/2003 | Das |
| 6,652,510 B2 | 11/2003 | Lord et al. |
| 6,653,091 B1 | 11/2003 | Dunn et al. |
| 6,656,114 B1 | 12/2003 | Poulsen et al. |
| 6,656,148 B2 | 12/2003 | Das et al. |
| 6,656,158 B2 | 12/2003 | Manhoney et al. |
| 6,656,159 B2 | 12/2003 | Flaherty et al. |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,359 B2 | 12/2003 | Gray |
| 6,663,602 B2 | 12/2003 | Moller |
| 6,666,021 B1 | 12/2003 | Keimel |
| 6,666,665 B1 | 12/2003 | Nguyen et al. |
| 6,666,821 B2 | 12/2003 | Keimel |
| 6,668,196 B1 | 12/2003 | Villegas et al. |
| 6,668,701 B1 | 12/2003 | Everitt |
| 6,669,663 B1 | 12/2003 | Thompson |
| 6,669,669 B2 | 12/2003 | Flaherty et al. |
| 6,673,033 B1 | 1/2004 | Sciulli et al. |
| 6,676,387 B1 | 1/2004 | Penn |
| 6,677,320 B2 | 1/2004 | Diederich et al. |
| 6,679,865 B2 | 1/2004 | Shekalim |
| 6,682,497 B2 | 1/2004 | Jensen et al. |
| 6,683,690 B1 | 1/2004 | Tobias |
| 6,687,522 B2 | 2/2004 | Tamada |
| 6,687,546 B2 | 2/2004 | Lebel et al. |
| 6,689,100 B2 | 2/2004 | Connelly et al. |
| 6,689,108 B2 | 2/2004 | Lavi et al. |
| 6,689,118 B2 | 2/2004 | Alchas et al. |
| 6,689,373 B2 | 2/2004 | Johnson et al. |
| 6,692,456 B1 | 2/2004 | Eppstein et al. |
| 6,692,457 B2 | 2/2004 | Flaherty et al. |
| 6,692,472 B2 | 2/2004 | Hansen et al. |
| 6,692,473 B2 | 2/2004 | St. Cyr et al. |
| 6,694,191 B2 | 2/2004 | Starkweather et al. |
| 6,695,011 B2 | 2/2004 | Sochtig |
| 6,696,090 B1 | 2/2004 | Nilsson et al. |
| 6,696,493 B2 | 2/2004 | Cavazza |
| 6,699,218 B2 | 3/2004 | Flaherty et al. |
| 6,699,234 B2 | 3/2004 | Yeh et al. |
| 6,699,885 B2 | 3/2004 | Phillips |
| 6,702,779 B2 | 3/2004 | Connelly et al. |
| 6,702,857 B2 | 3/2004 | Brauker et al. |
| 6,705,845 B2 | 3/2004 | Kreiger et al. |
| 6,706,008 B2 | 3/2004 | Vishnoi et al. |
| 6,706,009 B2 | 3/2004 | Diermann et al. |
| 6,706,689 B2 | 3/2004 | Coolidge et al. |
| 6,710,051 B1 | 3/2004 | Trier |
| 6,711,489 B2 | 3/2004 | Hasakara et al. |
| 6,712,095 B2 | 3/2004 | Williamson et al. |
| 6,715,516 B2 | 4/2004 | Ohms et al. |
| 6,716,190 B1 | 4/2004 | Glines et al. |
| 6,716,198 B2 | 4/2004 | Larsen |
| 6,718,206 B2 | 4/2004 | Casavant |
| 6,719,302 B2 | 4/2004 | Andrick |
| 6,723,068 B2 | 4/2004 | Lavi et al. |
| 6,723,072 B2 | 4/2004 | Flaherty et al. |
| 6,726,920 B1 | 4/2004 | Theeuwes et al. |
| 6,732,573 B2 | 5/2004 | Shin et al. |
| 6,733,446 B2 | 5/2004 | Lebel et al. |
| 6,734,186 B1 | 5/2004 | Maw et al. |
| 6,736,796 B2 | 5/2004 | Shekalim et al. |
| 6,738,052 B1 | 5/2004 | Manke et al. |
| 6,738,663 B2 | 5/2004 | Schroppel et al. |
| 6,738,707 B2 | 5/2004 | Kotwicki et al. |
| 6,740,059 B2 | 5/2004 | Flaherty et al. |
| 6,740,072 B2 | 5/2004 | Starkweather et al. |
| 6,740,075 B2 | 5/2004 | Lebel et al. |
| 6,743,201 B1 | 6/2004 | Doenig et al. |
| 6,744,152 B2 | 6/2004 | Kroll |
| 6,744,350 B2 | 6/2004 | Blomquist |
| 6,745,079 B2 | 6/2004 | Wohlgemuth et al. |
| 6,746,438 B1 | 6/2004 | Arnissolle |
| 6,748,930 B2 | 6/2004 | Bofinger et al. |
| 6,749,403 B2 | 6/2004 | Bryant et al. |
| 6,749,587 B2 | 6/2004 | Flaherty et al. |
| 6,752,785 B2 | 6/2004 | Van Antwerp et al. |
| 6,752,787 B1 | 6/2004 | Causey, III et al. |
| 6,755,628 B1 | 6/2004 | Howell |
| 6,755,810 B1 | 6/2004 | Buch-Rasmussen et al. |
| 6,758,593 B1 | 7/2004 | Terentiev |
| 6,758,810 B2 | 7/2004 | Lebel et al. |
| 6,759,386 B2 | 7/2004 | Franco |

(56) References Cited

U.S. PATENT DOCUMENTS

| | | |
|---|---|---|
| 6,767,188 B2 | 7/2004 | Vrane et al. |
| 6,767,896 B1 | 7/2004 | McIntosh et al. |
| 6,768,425 B2 | 7/2004 | Flaherty et al. |
| 6,769,384 B2 | 8/2004 | Dougherty |
| 6,770,054 B1 | 8/2004 | Smolyarov et al. |
| 6,770,067 B2 | 8/2004 | Lorenzen et al. |
| 6,773,669 B1 | 8/2004 | Holaday et al. |
| 6,773,739 B2 | 8/2004 | Hauck et al. |
| 6,775,577 B2 | 8/2004 | Crnkovich et al. |
| 6,776,776 B2 | 8/2004 | Alchas et al. |
| 6,780,156 B2 | 8/2004 | Haueter et al. |
| 6,780,171 B2 | 8/2004 | Gabel et al. |
| 6,780,426 B2 | 8/2004 | Zhang et al. |
| 6,780,770 B2 | 8/2004 | Larson |
| 6,780,836 B2 | 8/2004 | Unemori |
| 6,783,107 B2 | 8/2004 | Chatufale |
| 6,783,328 B2 | 8/2004 | Lucke et al. |
| 6,786,246 B2 | 9/2004 | Ohms et al. |
| 6,790,670 B2 | 9/2004 | Munagavalasa et al. |
| 6,796,956 B2 | 9/2004 | Hartlaub et al. |
| 6,801,420 B2 | 10/2004 | Talbot et al. |
| 6,804,002 B2 | 10/2004 | Fine et al. |
| 6,804,555 B2 | 10/2004 | Warkentin |
| 6,805,122 B2 | 10/2004 | Richey, II et al. |
| 6,805,687 B2 | 10/2004 | Dextradeur et al. |
| 6,808,506 B2 | 10/2004 | Lastovich et al. |
| 6,809,653 B1 | 10/2004 | Mann et al. |
| 6,810,290 B2 | 10/2004 | Lebel et al. |
| RE38,654 E | 11/2004 | Hill et al. |
| 6,811,533 B2 | 11/2004 | Lebel et al. |
| 6,811,534 B2 | 11/2004 | Bowman, IV et al. |
| 6,811,792 B2 | 11/2004 | Roser et al. |
| 6,813,519 B2 | 11/2004 | Lebel et al. |
| 6,813,964 B1 | 11/2004 | Clark et al. |
| 6,814,547 B2 | 11/2004 | Childers et al. |
| 6,821,249 B2 | 11/2004 | Casscells, III et al. |
| 6,821,484 B1 | 11/2004 | Gregersen |
| 6,824,529 B2 | 11/2004 | Gross et al. |
| 6,827,524 B2 | 12/2004 | Starry, Jr. et al. |
| 6,827,702 B2 | 12/2004 | Lebel et al. |
| 6,827,710 B1 | 12/2004 | Mooney et al. |
| 6,827,898 B1 | 12/2004 | Fausset et al. |
| 6,828,552 B2 | 12/2004 | Hartley |
| 6,830,558 B2 | 12/2004 | Flaherty et al. |
| 6,830,560 B1 | 12/2004 | Gross et al. |
| 6,835,175 B1 | 12/2004 | Porumbescu |
| 6,835,194 B2 | 12/2004 | Johnson et al. |
| 6,842,042 B2 | 1/2005 | Vanhout |
| 6,842,642 B2 | 1/2005 | Vanhout |
| 6,843,782 B2 | 1/2005 | Gross et al. |
| 6,847,898 B1 | 1/2005 | Chen et al. |
| 6,851,449 B2 | 2/2005 | Kleibrink |
| 6,852,104 B2 | 2/2005 | Blomquist |
| 6,852,487 B1 | 2/2005 | Barany et al. |
| 6,854,432 B2 | 2/2005 | Hirano |
| 6,854,620 B2 | 2/2005 | Ramey |
| 6,858,011 B2 | 2/2005 | Sehgal |
| 6,858,403 B2 | 2/2005 | Han et al. |
| 6,859,673 B2 | 2/2005 | Steffen |
| 6,862,466 B2 | 3/2005 | Ackerman |
| 6,864,101 B1 | 3/2005 | Winkler et al. |
| 6,867,196 B1 | 3/2005 | Wolff et al. |
| 6,868,358 B2 | 3/2005 | Brown, Jr. |
| 6,872,200 B2 | 3/2005 | Mann et al. |
| 6,873,268 B2 | 3/2005 | Lebel et al. |
| 6,876,885 B2 | 4/2005 | Swoyer et al. |
| 6,877,713 B1 | 4/2005 | Gray et al. |
| 6,880,564 B2 | 4/2005 | Erickson |
| 6,882,940 B2 | 4/2005 | Potts et al. |
| 6,884,122 B2 | 4/2005 | Robinson et al. |
| 6,884,228 B2 | 4/2005 | Brown et al. |
| 6,885,881 B2 | 4/2005 | Leonhardt |
| 6,885,888 B2 | 4/2005 | Rezai |
| 6,886,556 B2 | 5/2005 | Fuchs |
| 6,892,755 B2 | 5/2005 | Black |
| 6,892,900 B2 | 5/2005 | Drechsel |
| 6,893,415 B2 | 5/2005 | Madsen et al. |
| 6,894,024 B2 | 5/2005 | Coolidge et al. |
| 6,895,263 B2 | 5/2005 | Shin et al. |
| 6,896,666 B2 | 5/2005 | Kochamba |
| 6,899,699 B2 | 5/2005 | Enggaard |
| RE38,749 E | 6/2005 | Dardik |
| 6,902,905 B2 | 6/2005 | Burson et al. |
| 6,905,314 B2 | 6/2005 | Danby |
| 6,905,479 B1 | 6/2005 | Bouchard et al. |
| 6,906,028 B2 | 6/2005 | DeFelippis et al. |
| 6,908,591 B2 | 6/2005 | MacPhee et al. |
| 6,909,840 B2 | 6/2005 | Harwig et al. |
| 6,912,425 B2 | 6/2005 | Nova et al. |
| 6,913,933 B2 | 7/2005 | Jacobs et al. |
| 6,914,076 B2 | 7/2005 | Cavazza |
| 6,916,010 B2 | 7/2005 | Beck et al. |
| 6,916,159 B2 | 7/2005 | Rush et al. |
| 6,918,542 B2 | 7/2005 | Silverbrook et al. |
| 6,923,006 B2 | 8/2005 | Walton |
| 6,923,180 B2 | 8/2005 | Richey, II et al. |
| 6,923,764 B2 | 8/2005 | Aceti et al. |
| 6,926,694 B2 | 8/2005 | Marano-Ford et al. |
| 6,928,338 B1 | 8/2005 | Buchser et al. |
| 6,930,093 B2 | 8/2005 | Brantl |
| 6,931,845 B2 | 8/2005 | Schaeffer |
| 6,931,925 B2 | 8/2005 | Huemer et al. |
| 6,932,114 B2 | 8/2005 | Sparks |
| 6,932,584 B2 | 8/2005 | Gray et al. |
| 6,932,796 B2 | 8/2005 | Sage et al. |
| 6,935,531 B1 | 8/2005 | Clayton |
| 6,935,539 B2 | 8/2005 | Krieger et al. |
| 6,936,026 B2 | 8/2005 | Diermann et al. |
| 6,936,029 B2 | 8/2005 | Mann et al. |
| 6,936,035 B2 | 8/2005 | Rake et al. |
| 6,936,046 B2 | 8/2005 | Hissong et al. |
| 6,939,323 B2 | 9/2005 | Angel et al. |
| 6,939,324 B2 | 9/2005 | Gonneli et al. |
| 6,942,636 B2 | 9/2005 | Holst et al. |
| 6,943,034 B1 | 9/2005 | Winkler et al. |
| 6,945,760 B2 | 9/2005 | Gray et al. |
| 6,946,117 B1 | 9/2005 | Schutt et al. |
| 6,948,918 B2 | 9/2005 | Hansen |
| 6,949,081 B1 | 9/2005 | Chance |
| 6,950,708 B2 | 9/2005 | Bowman, IV et al. |
| 6,951,165 B2 | 10/2005 | Kuhn et al. |
| 6,951,553 B2 | 10/2005 | Bubb et al. |
| 6,952,604 B2 | 10/2005 | DeNuzzio et al. |
| 6,952,963 B2 | 10/2005 | Delnevo |
| 6,953,323 B2 | 10/2005 | Childers et al. |
| 6,955,819 B2 | 10/2005 | Zhang et al. |
| 6,955,915 B2 | 10/2005 | Fodor et al. |
| 6,956,204 B2 | 10/2005 | Dong et al. |
| 6,957,655 B2 | 10/2005 | Erickson et al. |
| 6,957,924 B1 | 10/2005 | McMeekin et al. |
| 6,958,073 B2 | 10/2005 | Rogers et al. |
| 6,958,691 B1 | 10/2005 | Anderson et al. |
| 6,958,705 B2 | 10/2005 | Lebel et al. |
| 6,960,184 B2 | 11/2005 | Willis et al. |
| 6,960,192 B1 | 11/2005 | Flaherty et al. |
| 6,962,103 B2 | 11/2005 | Sandlin |
| 6,962,151 B1 | 11/2005 | Knoch et al. |
| 6,963,770 B2 | 11/2005 | Scarantino et al. |
| 6,964,356 B2 | 11/2005 | Kim |
| 6,966,325 B2 | 11/2005 | Erickson |
| 6,966,895 B2 | 11/2005 | Tribe |
| 6,969,369 B2 | 11/2005 | Struble |
| 6,970,741 B1 | 11/2005 | Whitehurst et al. |
| 6,970,742 B2 | 11/2005 | Mann et al. |
| 6,971,999 B2 | 12/2005 | Py et al. |
| 6,973,374 B2 | 12/2005 | Ader |
| 6,974,055 B2 | 12/2005 | Moore et al. |
| 6,974,115 B2 | 12/2005 | Silva |
| 6,974,437 B2 | 12/2005 | Lebel et al. |
| 6,974,438 B2 | 12/2005 | Shekalim |
| 6,974,588 B1 | 12/2005 | Miranda et al. |
| 6,979,308 B1 | 12/2005 | MacDonald et al. |
| 6,979,315 B2 | 12/2005 | Rogers et al. |
| 6,979,316 B1 | 12/2005 | Rubin et al. |

(56) References Cited

U.S. PATENT DOCUMENTS

| | | |
|---|---|---|
| 6,979,326 B2 | 12/2005 | Mann et al. |
| 6,980,855 B2 | 12/2005 | Cho |
| 6,981,499 B2 | 1/2006 | Anderson et al. |
| 6,981,967 B2 | 1/2006 | Massengale et al. |
| 6,982,248 B2 | 1/2006 | Coolidge et al. |
| 6,983,209 B2 | 1/2006 | Jaynes |
| 6,985,770 B2 | 1/2006 | Nyhart, Jr. |
| 6,985,771 B2 | 1/2006 | Fischell et al. |
| 6,986,867 B2 | 1/2006 | Hanley et al. |
| 6,987,129 B2 | 1/2006 | Mak et al. |
| 6,990,809 B2 | 1/2006 | Abouraphael |
| 6,991,619 B2 | 1/2006 | Marano-Ford et al. |
| 6,991,620 B2 | 1/2006 | Marano-Ford et al. |
| 6,993,795 B2 | 2/2006 | Prineppi |
| 6,994,691 B2 | 2/2006 | Ejlersen |
| 6,994,700 B2 | 2/2006 | Elkins et al. |
| 6,997,202 B2 | 2/2006 | Olander |
| 6,997,905 B2 | 2/2006 | Gillespie, Jr. et al. |
| 6,997,911 B2 | 2/2006 | Klitmose |
| 6,997,916 B2 | 2/2006 | Simas, Jr. et al. |
| 6,997,920 B2 | 2/2006 | Mann et al. |
| 6,997,921 B2 | 2/2006 | Gray et al. |
| 6,998,387 B1 | 2/2006 | Goke et al. |
| 6,998,404 B2 | 2/2006 | Moskowitz |
| 6,999,810 B2 | 2/2006 | Berner et al. |
| 6,999,854 B2 | 2/2006 | Roth |
| 7,003,336 B2 | 2/2006 | Holker et al. |
| 7,004,928 B2 | 2/2006 | Aceti et al. |
| 7,008,399 B2 | 3/2006 | Larson et al. |
| 7,008,403 B1 | 3/2006 | Mallett |
| 7,008,413 B2 | 3/2006 | Kovach et al. |
| 7,010,340 B2 | 3/2006 | Scarantino et al. |
| 7,011,630 B2 | 3/2006 | Desai et al. |
| 7,011,682 B2 | 3/2006 | Lashinski et al. |
| 7,013,727 B2 | 3/2006 | Delnevo |
| 7,015,782 B2 | 3/2006 | Kincaid et al. |
| 7,018,336 B2 | 3/2006 | Enegren et al. |
| 7,018,360 B2 | 3/2006 | Flaherty et al. |
| 7,018,361 B2 | 3/2006 | Gillespie, Jr. et al. |
| 7,018,630 B2 | 3/2006 | Takaoka |
| 7,022,071 B2 | 4/2006 | Schaupp et al. |
| 7,022,072 B2 | 4/2006 | Fox et al. |
| 7,022,087 B2 | 4/2006 | Dempster et al. |
| 7,022,108 B2 | 4/2006 | Marano-Ford et al. |
| 7,024,244 B2 | 4/2006 | Muhlenberg et al. |
| 7,024,245 B2 | 4/2006 | Lebel et al. |
| 7,025,716 B1 | 4/2006 | Meloul et al. |
| 7,025,743 B2 | 4/2006 | Mann et al. |
| 7,027,478 B2 | 4/2006 | Ackley |
| 7,027,871 B2 | 4/2006 | Burnes et al. |
| 7,029,455 B2 | 4/2006 | Flaherty |
| 7,031,772 B2 | 4/2006 | Condie et al. |
| 7,033,338 B2 | 4/2006 | Vilks et al. |
| 7,033,539 B2 | 4/2006 | Krensky et al. |
| 7,033,843 B2 | 4/2006 | Hasegawa et al. |
| 7,011,647 B2 | 5/2006 | Purdy et al. |
| 7,041,082 B2 | 5/2006 | Blomquist et al. |
| 7,047,070 B2 | 5/2006 | Wilkinson et al. |
| 7,048,193 B2 | 5/2006 | Tsukada et al. |
| 7,048,951 B1 | 5/2006 | Seitz et al. |
| 7,052,251 B2 | 5/2006 | Nason et al. |
| 7,052,483 B2 | 5/2006 | Wojcik |
| 7,053,761 B2 | 5/2006 | Schofield et al. |
| 7,056,179 B2 | 6/2006 | Courtney |
| 7,056,302 B2 | 6/2006 | Douglas |
| 7,056,494 B2 | 6/2006 | Adjei et al. |
| 7,056,887 B2 | 6/2006 | Coolidge et al. |
| 7,058,438 B2 | 6/2006 | Grace et al. |
| 7,059,348 B2 | 6/2006 | Nat |
| 7,060,856 B2 | 6/2006 | Macikenas et al. |
| 7,063,684 B2 | 6/2006 | Moberg |
| 7,064,472 B2 | 6/2006 | Pelrine et al. |
| 7,066,359 B2 | 6/2006 | Greiner-Perth |
| 7,066,910 B2 | 6/2006 | Bauhahn et al. |
| 7,066,915 B2 | 6/2006 | Olsen |
| 7,066,922 B2 | 6/2006 | Angel et al. |
| 7,069,075 B2 | 6/2006 | Olson |
| 7,070,577 B1 | 7/2006 | Haller et al. |
| 7,072,802 B2 | 7/2006 | Hartlaub |
| 7,073,485 B2 | 7/2006 | Truscott et al. |
| 7,073,713 B2 | 7/2006 | Silverbrook et al. |
| 7,074,200 B2 | 7/2006 | Lewis |
| 7,077,822 B1 | 7/2006 | Howard, III |
| 7,078,163 B2 | 7/2006 | Torrianni |
| 7,081,105 B2 | 7/2006 | Reilly et al. |
| 7,082,333 B1 | 7/2006 | Bauhahn et al. |
| 7,082,812 B2 | 8/2006 | Lenormand et al. |
| 7,083,108 B2 | 8/2006 | Silverbrook et al. |
| 7,083,592 B2 | 8/2006 | Lastovich et al. |
| 7,083,599 B2 | 8/2006 | Alchas et al. |
| 7,089,608 B2 | 8/2006 | Erb |
| 7,090,648 B2 | 8/2006 | Sackner et al. |
| 7,091,179 B2 | 8/2006 | Franco |
| 7,092,011 B2 | 8/2006 | Silverbrook et al. |
| 7,092,796 B2 | 8/2006 | Vanderveen |
| 7,095,210 B2 | 8/2006 | Tamura et al. |
| 7,096,889 B1 | 8/2006 | Roys |
| 7,097,104 B2 | 8/2006 | Silverbrook et al. |
| 7,098,803 B2 | 8/2006 | Mann et al. |
| 7,104,973 B2 | 9/2006 | Woolston et al. |
| 7,104,981 B2 | 9/2006 | Elkins et al. |
| 7,107,706 B1 | 9/2006 | Bailey, Sr. et al. |
| 7,107,837 B2 | 9/2006 | Lauman et al. |
| 7,108,491 B2 | 9/2006 | Ganser |
| 7,108,679 B2 | 9/2006 | Alchas |
| 7,109,878 B2 | 9/2006 | Mann et al. |
| 7,111,346 B2 | 9/2006 | Inman et al. |
| 7,115,108 B2 | 10/2006 | Wilkinson et al. |
| 7,118,351 B2 | 10/2006 | Effenhauser et al. |
| 7,118,676 B2 | 10/2006 | Mueth et al. |
| 7,122,151 B2 | 10/2006 | Johannsson et al. |
| 7,127,292 B2 | 10/2006 | Warman et al. |
| 7,128,727 B2 | 10/2006 | Flaherty et al. |
| 7,128,730 B2 | 10/2006 | Marano-Ford et al. |
| 7,131,967 B2 | 11/2006 | Gray et al. |
| 7,133,329 B2 | 11/2006 | Skyggebjerg et al. |
| 7,136,701 B2 | 11/2006 | Greatbatch et al. |
| 7,137,951 B2 | 11/2006 | Pilarski |
| 7,137,964 B2 | 11/2006 | Flaherty et al. |
| 7,138,141 B2 | 11/2006 | Platz et al. |
| 7,140,332 B2 | 11/2006 | Klein et al. |
| 7,141,425 B2 | 11/2006 | Dzekunov et al. |
| 7,141,812 B2 | 11/2006 | Appleby et al. |
| 7,144,384 B2 | 12/2006 | Gorman et al. |
| 7,144,729 B2 | 12/2006 | Rolland et al. |
| 7,147,386 B2 | 12/2006 | Zhang et al. |
| 7,147,839 B2 | 12/2006 | Sampath et al. |
| 7,150,409 B2 | 12/2006 | Gonneli et al. |
| 7,150,724 B2 | 12/2006 | Morris et al. |
| 7,150,726 B2 | 12/2006 | Dalton |
| 7,150,737 B2 | 12/2006 | Purdy et al. |
| 7,150,741 B2 | 12/2006 | Erickson et al. |
| 7,152,673 B2 | 12/2006 | Lohbeck |
| 7,153,286 B2 | 12/2006 | Busby et al. |
| 7,153,823 B2 | 12/2006 | Franco |
| 7,156,808 B2 | 1/2007 | Quy |
| 7,156,838 B2 | 1/2007 | Gabel et al. |
| 7,159,271 B2 | 1/2007 | Sepke et al. |
| 7,162,303 B2 | 1/2007 | Levin et al. |
| 7,163,385 B2 | 1/2007 | Gharib et al. |
| 7,163,520 B2 | 1/2007 | Bernard et al. |
| 7,166,280 B2 | 1/2007 | Franco |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,181,505 B2 | 2/2007 | Haller et al. |
| 7,183,068 B2 | 2/2007 | Burson et al. |
| 7,186,236 B2 | 3/2007 | Gibson et al. |
| 7,187,404 B2 | 3/2007 | Silverbrook et al. |
| 7,187,528 B2 | 3/2007 | Talbot et al. |
| 7,187,969 B2 | 3/2007 | Willis |
| 7,189,352 B2 | 3/2007 | Carpenter et al. |
| 7,193,521 B2 | 3/2007 | Moberg et al. |
| 7,194,890 B2 | 3/2007 | Tanaka et al. |

(56) References Cited

U.S. PATENT DOCUMENTS

| | | |
|---|---|---|
| 7,195,616 B2 | 3/2007 | Diller et al. |
| 7,198,603 B2 | 4/2007 | Penner et al. |
| 7,198,637 B2 | 4/2007 | Deshmukh et al. |
| 7,198,751 B2 | 4/2007 | Carpenter et al. |
| 7,198,940 B2 | 4/2007 | Vellinger et al. |
| 7,201,319 B2 | 4/2007 | Silverbrook et al. |
| 7,201,730 B2 | 4/2007 | Davidner et al. |
| 7,204,823 B2 | 4/2007 | Estes et al. |
| 7,204,958 B2 | 4/2007 | Olsen et al. |
| 7,207,952 B2 | 4/2007 | Takinami et al. |
| 7,207,964 B2 | 4/2007 | Davidner et al. |
| 7,208,119 B1 | 4/2007 | Kurtock et al. |
| 7,208,120 B2 | 4/2007 | Bitensky et al. |
| 7,214,207 B2 | 5/2007 | Fentress et al. |
| 7,214,221 B2 | 5/2007 | Fentress et al. |
| 7,214,658 B2 | 5/2007 | Tobinick |
| 7,217,699 B2 | 5/2007 | Yakubov |
| 7,217,796 B2 | 5/2007 | Wang et al. |
| 7,220,109 B2 | 5/2007 | Kultgen |
| 7,220,236 B2 | 5/2007 | Pan |
| 7,220,248 B2 | 5/2007 | Mernoe et al. |
| 7,220,365 B2 | 5/2007 | Qu et al. |
| 7,224,815 B2 | 5/2007 | Maltan et al. |
| 7,225,807 B2 | 6/2007 | Papania et al. |
| 7,226,278 B2 | 6/2007 | Nason et al. |
| 7,226,910 B2 | 6/2007 | Wilson et al. |
| 7,229,288 B2 | 6/2007 | Stuart et al. |
| 7,231,263 B2 | 6/2007 | Choi |
| 7,232,423 B2 | 6/2007 | Mernoe et al. |
| 7,232,430 B2 | 6/2007 | Carlisle et al. |
| 7,232,435 B2 | 6/2007 | Hildebrand et al. |
| 7,234,645 B2 | 6/2007 | Silverbrook |
| 7,235,164 B2 | 6/2007 | Anex et al. |
| 7,235,583 B1 | 6/2007 | Webb et al. |
| 7,237,694 B2 | 7/2007 | Freudinger |
| 7,238,165 B2 | 7/2007 | Vincent et al. |
| 7,239,941 B2 | 7/2007 | Mori et al. |
| 7,244,225 B2 | 7/2007 | Loeb et al. |
| 7,244,354 B2 | 7/2007 | Burris et al. |
| 7,247,138 B2 | 7/2007 | Reghabi et al. |
| 7,247,428 B2 | 7/2007 | Makrigiorgos |
| 7,247,702 B2 | 7/2007 | Gardner et al. |
| 7,250,037 B2 | 7/2007 | Shermer et al. |
| 7,251,516 B2 | 7/2007 | Walker et al. |
| 7,252,014 B1 | 8/2007 | Mayer et al. |
| 7,252,651 B2 | 8/2007 | Haider et al. |
| 7,254,782 B1 | 8/2007 | Sherer |
| 7,255,690 B2 | 8/2007 | Gray et al. |
| 7,256,771 B2 | 8/2007 | Novak et al. |
| 7,256,824 B2 | 8/2007 | Silverbrook et al. |
| 7,256,888 B2 | 8/2007 | Staehr et al. |
| 7,258,864 B2 | 8/2007 | Clark |
| RE39,816 E | 9/2007 | Stanton et al. |
| 7,264,730 B2 | 9/2007 | Connell et al. |
| 7,265,091 B2 | 9/2007 | Lue et al. |
| 7,267,665 B2 | 9/2007 | Steil et al. |
| 7,267,753 B2 | 9/2007 | Anex et al. |
| 7,267,771 B2 | 9/2007 | Gorsuch et al. |
| 7,268,859 B2 | 9/2007 | Sage, Jr. et al. |
| 7,272,544 B2 | 9/2007 | Gopal et al. |
| 7,276,027 B2 | 10/2007 | Haar et al. |
| 7,276,057 B2 | 10/2007 | Gerber |
| 7,278,983 B2 | 10/2007 | Ireland et al. |
| 7,281,519 B2 | 10/2007 | Schroeder et al. |
| 7,282,029 B1 | 10/2007 | Poulsen |
| 7,285,293 B2 | 10/2007 | Castillo et al. |
| 7,287,289 B1 | 10/2007 | Hagopian |
| 7,287,485 B2 | 10/2007 | Petrakis |
| 7,288,085 B2 | 10/2007 | Olsen |
| 7,288,760 B2 | 10/2007 | Weitz |
| 7,289,142 B2 | 10/2007 | Silverbrook |
| 7,291,126 B2 | 11/2007 | Shekalim et al. |
| 7,291,132 B2 | 11/2007 | Deruntz et al. |
| 7,291,133 B1 | 11/2007 | Kindler et al. |
| 7,295,867 B2 | 11/2007 | Berner et al. |
| 7,297,151 B2 | 11/2007 | Boecker et al. |
| 7,302,295 B2 | 11/2007 | Stahmann et al. |
| 7,303,543 B1 | 12/2007 | Maule et al. |
| 7,303,549 B2 | 12/2007 | Flaherty et al. |
| 7,303,680 B2 | 12/2007 | Connell et al. |
| 7,304,033 B2 | 12/2007 | Larsen et al. |
| 7,305,975 B2 | 12/2007 | Reddy |
| 7,306,555 B2 | 12/2007 | Dolecek et al. |
| 7,306,578 B2 | 12/2007 | Gray et al. |
| 7,311,693 B2 | 12/2007 | Shekalim et al. |
| 7,316,700 B2 | 1/2008 | Alden et al. |
| 7,316,899 B2 | 1/2008 | McDevitt et al. |
| 7,318,892 B2 | 1/2008 | Connell et al. |
| 7,320,675 B2 | 1/2008 | Pastore et al. |
| 7,320,677 B2 | 1/2008 | Brouillette et al. |
| 7,322,321 B2 | 1/2008 | Robinson |
| 7,323,141 B2 | 1/2008 | Kirchhevel |
| 7,323,543 B2 | 1/2008 | Van Antwerp et al. |
| 7,324,012 B2 | 1/2008 | Mann et al. |
| 7,324,949 B2 | 1/2008 | Bristol et al. |
| 7,334,556 B2 | 2/2008 | Wachigai et al. |
| 7,335,377 B2 | 2/2008 | Stern et al. |
| 7,338,464 B2 | 3/2008 | Blischak et al. |
| 7,341,577 B2 | 3/2008 | Gill |
| 7,341,581 B2 | 3/2008 | Mallet |
| 7,344,500 B2 | 3/2008 | Talbot et al. |
| 7,344,507 B2 | 3/2008 | Briggs et al. |
| 7,344,894 B2 | 3/2008 | Greenstein et al. |
| 7,347,201 B2 | 3/2008 | Djupesland |
| 7,347,836 B2 | 3/2008 | Peterson et al. |
| 7,347,854 B2 | 3/2008 | Shelton et al. |
| 7,348,176 B2 | 3/2008 | DiMilla et al. |
| 7,350,190 B2 | 3/2008 | Torres et al. |
| 7,351,239 B2 | 4/2008 | Gill |
| 7,351,340 B2 | 4/2008 | Connell et al. |
| 7,351,411 B2 | 4/2008 | Holash et al. |
| 7,351,695 B2 | 4/2008 | Almarssoo et al. |
| 7,354,420 B2 | 4/2008 | Steil et al. |
| 7,356,382 B2 | 4/2008 | Vanderveen |
| 7,357,794 B2 | 4/2008 | Makower et al. |
| 7,357,899 B2 | 4/2008 | Gaillard et al. |
| 7,358,091 B2 | 4/2008 | Phillips et al. |
| 7,361,155 B2 | 4/2008 | Sage, Jr. et al. |
| 7,362,971 B2 | 4/2008 | Silverbrook et al. |
| 7,363,072 B2 | 4/2008 | Movahed |
| 7,363,075 B2 | 4/2008 | Stern et al. |
| 7,364,566 B2 | 4/2008 | Elkins et al. |
| 7,364,568 B2 | 4/2008 | Angel et al. |
| 7,366,925 B2 | 4/2008 | Keely et al. |
| 7,368,003 B2 | 5/2008 | Crapser et al. |
| 7,371,418 B2 | 5/2008 | Sheabar et al. |
| 7,373,083 B2 | 5/2008 | Silverbrook et al. |
| 7,373,690 B2 | 5/2008 | Sepke et al. |
| 7,373,826 B2 | 5/2008 | Weber et al. |
| 7,374,544 B2 | 5/2008 | Freeman et al. |
| 7,374,556 B2 | 5/2008 | Mallett |
| 7,377,706 B2 | 5/2008 | Silverbrook et al. |
| 7,377,907 B2 | 5/2008 | Shekalim et al. |
| 7,378,270 B2 | 5/2008 | Azarnia et al. |
| 7,378,443 B2 | 5/2008 | Berge |
| 7,380,447 B2 | 6/2008 | Rollinger et al. |
| 7,384,397 B2 | 6/2008 | Zhang et al. |
| 7,384,410 B2 | 6/2008 | Eggers et al. |
| 7,384,413 B2 | 6/2008 | Gross et al. |
| 7,384,912 B2 | 6/2008 | Stewart |
| 7,385,443 B1 | 6/2008 | Denison |
| 7,386,346 B2 | 6/2008 | Struble |
| 7,390,311 B2 | 6/2008 | Hildebrand et al. |
| 7,390,314 B2 | 6/2008 | Stutz, Jr. et al. |
| 7,390,458 B2 | 6/2008 | Burow et al. |
| 7,394,182 B2 | 7/2008 | Pelrine et al. |
| 7,396,353 B2 | 7/2008 | Lorenzen et al. |
| 7,399,277 B2 | 7/2008 | Saidara et al. |
| 7,399,304 B2 | 7/2008 | Gambale et al. |
| 7,399,401 B2 | 7/2008 | Rush |
| 7,399,772 B2 | 7/2008 | Phillips |
| 7,402,153 B2 | 7/2008 | Steil et al. |
| 7,402,154 B2 | 7/2008 | Holst et al. |
| 7,405,055 B2 | 7/2008 | Dunn et al. |

(56) References Cited

U.S. PATENT DOCUMENTS

| | | |
|---|---|---|
| 7,407,489 B2 | 8/2008 | Holst et al. |
| 7,407,490 B2 | 8/2008 | Bendsen et al. |
| 7,410,468 B2 | 8/2008 | Freeman et al. |
| 7,410,475 B2 | 8/2008 | Krensky et al. |
| 7,411,204 B2 | 8/2008 | Appleby et al. |
| 7,416,644 B2 | 8/2008 | Bonde |
| 7,421,316 B2 | 9/2008 | Gray et al. |
| 7,421,882 B2 | 9/2008 | Leddy et al. |
| 7,425,204 B2 | 9/2008 | Angel et al. |
| 7,426,408 B2 | 9/2008 | DeNuzzio et al. |
| 7,427,275 B2 | 9/2008 | Deruntz et al. |
| 7,429,255 B2 | 9/2008 | Thompson |
| 7,429,258 B2 | 9/2008 | Angel et al. |
| 7,429,269 B2 | 9/2008 | Schwammenthal et al. |
| 7,435,250 B2 | 10/2008 | Francischelli et al. |
| 7,435,717 B2 | 10/2008 | Bisgaier et al. |
| 7,440,806 B1 | 10/2008 | Whitehurst et al. |
| 7,442,682 B2 | 10/2008 | Kitaura et al. |
| 7,444,436 B2 | 10/2008 | Wille |
| RE40,570 E | 11/2008 | Carpentier et al. |
| 7,445,616 B2 | 11/2008 | Petrakis |
| 7,446,091 B2 | 11/2008 | Van Den Berghe |
| 7,449,333 B2 | 11/2008 | Rolland et al. |
| 7,452,301 B2 | 11/2008 | Yoshioka |
| 7,455,663 B2 | 11/2008 | Bikovsky |
| 7,455,835 B2 | 11/2008 | Cohen et al. |
| 7,459,305 B2 | 12/2008 | Levy |
| 7,460,152 B2 | 12/2008 | Silverbrook et al. |
| 7,460,350 B2 | 12/2008 | Talbot et al. |
| 7,463,934 B2 | 12/2008 | Tronnes et al. |
| 7,464,010 B2 | 12/2008 | Yang et al. |
| 7,464,580 B2 | 12/2008 | Zeng et al. |
| 7,464,704 B2 | 12/2008 | Braithwaite |
| 7,465,285 B2 | 12/2008 | Hutchinson et al. |
| 7,465,375 B2 | 12/2008 | Demers et al. |
| 7,467,027 B2 | 12/2008 | Ding et al. |
| 7,467,613 B2 | 12/2008 | Taylor, Sr. |
| 7,468,033 B2 | 12/2008 | Van Antwerp et al. |
| 7,469,383 B2 | 12/2008 | Busch |
| 7,469,697 B2 | 12/2008 | Lee et al. |
| 7,469,844 B2 | 12/2008 | Conway et al. |
| 7,470,246 B2 | 12/2008 | Mori et al. |
| 7,471,994 B2 | 12/2008 | Ford et al. |
| 7,473,239 B2 | 1/2009 | Wang et al. |
| 7,473,247 B2 | 1/2009 | Mikszta et al. |
| 7,474,968 B2 | 1/2009 | Ding et al. |
| 7,475,825 B2 | 1/2009 | Silverbrook et al. |
| 7,476,200 B2 | 1/2009 | Tal |
| 7,476,209 B2 | 1/2009 | Gara et al. |
| 7,479,123 B2 | 1/2009 | Briggs |
| 7,481,218 B2 | 1/2009 | Djupesland |
| 7,481,759 B2 | 1/2009 | Whitehurst et al. |
| 7,481,776 B2 | 1/2009 | Boecker et al. |
| 7,481,792 B2 | 1/2009 | Gonelli et al. |
| 7,483,050 B2 | 1/2009 | Silverbrook et al. |
| 7,483,743 B2 | 1/2009 | Mann et al. |
| 7,485,298 B2 | 2/2009 | Powell |
| 7,491,178 B2 | 2/2009 | Boecker et al. |
| 7,491,187 B2 | 2/2009 | Van Den Berghe et al. |
| 7,491,335 B2 | 2/2009 | Reddy et al. |
| 7,493,154 B2 | 2/2009 | Bonner et al. |
| 7,493,171 B1 | 2/2009 | Whitehurst et al. |
| 7,494,481 B2 | 2/2009 | Moberg et al. |
| 7,497,841 B2 | 3/2009 | Alchas |
| 7,498,563 B2 | 3/2009 | Mandro et al. |
| 7,500,959 B2 | 3/2009 | Munk |
| 7,503,903 B2 | 3/2009 | Carlisle et al. |
| 7,505,869 B2 | 3/2009 | Hartlaub |
| 7,507,220 B2 | 3/2009 | Childers et al. |
| 7,507,235 B2 | 3/2009 | Keogh et al. |
| 7,509,169 B2 | 3/2009 | Eigler et al. |
| 7,510,544 B2 | 3/2009 | Vilks et al. |
| 7,510,552 B2 | 3/2009 | Lebel et al. |
| 7,511,914 B2 | 3/2009 | Hiller et al. |
| 7,514,075 B2 | 4/2009 | Hedrick et al. |
| 7,514,401 B2 | 4/2009 | Franco |
| 7,515,060 B2 | 4/2009 | Blomquist |
| 7,517,332 B2 | 4/2009 | Tonelli et al. |
| 7,517,335 B2 | 4/2009 | Gravesen et al. |
| 7,517,440 B2 | 4/2009 | Anex et al. |
| 7,517,498 B2 | 4/2009 | Fredrick |
| 7,517,530 B2 | 4/2009 | Clark |
| 7,520,867 B2 | 4/2009 | Bowman et al. |
| 7,524,045 B2 | 4/2009 | Silverbrook et al. |
| 7,524,287 B2 | 4/2009 | Bharmi |
| 7,524,293 B2 | 4/2009 | Freeman et al. |
| 7,524,304 B2 | 4/2009 | Genosar |
| 7,530,968 B2 | 5/2009 | Gonnelli |
| 7,530,975 B2 | 5/2009 | Hunter |
| 7,534,221 B2 | 5/2009 | Pile-Spellman |
| 7,534,226 B2 | 5/2009 | Mernoe et al. |
| 7,536,983 B2 | 5/2009 | Layher et al. |
| 7,537,571 B2 | 5/2009 | Freeman et al. |
| 7,540,859 B2 | 6/2009 | Claude et al. |
| 7,540,880 B2 | 6/2009 | Nolting |
| 7,543,581 B2 | 6/2009 | Djupesland |
| 7,547,281 B2 | 6/2009 | Hayes et al. |
| 7,547,287 B2 | 6/2009 | Boecker et al. |
| 7,548,314 B2 | 6/2009 | Altobelli et al. |
| 7,551,202 B2 | 6/2009 | Silverbrook |
| 7,553,281 B2 | 6/2009 | Hellwig et al. |
| 7,553,291 B2 | 6/2009 | Duffy et al. |
| 7,553,813 B2 | 6/2009 | Unemori |
| 7,556,613 B2 | 7/2009 | Wittmann et al. |
| 7,556,841 B2 | 7/2009 | Kimball et al. |
| 7,558,629 B2 | 7/2009 | Keimel et al. |
| 7,559,223 B2 | 7/2009 | Chen et al. |
| 7,559,524 B2 | 7/2009 | Gray et al. |
| 7,563,232 B2 | 7/2009 | Freeman et al. |
| 7,563,253 B2 | 7/2009 | Tanner et al. |
| 7,563,255 B2 | 7/2009 | Adamis et al. |
| D598,109 S | 8/2009 | Collins et al. |
| 7,569,030 B2 | 8/2009 | Lebel et al. |
| 7,569,036 B2 | 8/2009 | Domkowski et al. |
| 7,569,050 B2 | 8/2009 | Moberg et al. |
| 7,571,635 B2 | 8/2009 | Lyon |
| 7,572,789 B2 | 8/2009 | Cowen et al. |
| 7,577,477 B2 | 8/2009 | Allen et al. |
| 7,582,063 B2 | 9/2009 | Wurster et al. |
| 7,582,099 B2 | 9/2009 | Freeman et al. |
| 7,583,190 B2 | 9/2009 | Reggiardo et al. |
| 7,584,846 B2 | 9/2009 | Senter |
| 7,588,046 B1 | 9/2009 | Erickson |
| 7,588,550 B2 | 9/2009 | Leonard et al. |
| 7,588,563 B2 | 9/2009 | Guala |
| 7,588,784 B2 | 9/2009 | Maday et al. |
| 7,589,059 B2 | 9/2009 | Wolff et al. |
| 7,590,443 B2 | 9/2009 | Bharmi |
| 7,591,801 B2 | 9/2009 | Brauker et al. |
| 7,594,889 B2 | 9/2009 | St. Ores et al. |
| 7,597,682 B2 | 10/2009 | Moberg |
| 7,598,031 B2 | 10/2009 | Liew |
| 7,602,310 B2 | 10/2009 | Mann et al. |
| 7,603,174 B2 | 10/2009 | De Ridder |
| 7,604,592 B2 | 10/2009 | Freeman et al. |
| 7,604,619 B2 | 10/2009 | Eich et al. |
| 7,605,710 B2 | 10/2009 | Crnkovich et al. |
| 7,606,274 B2 | 10/2009 | Mirov et al. |
| 7,606,615 B2 | 10/2009 | Makower et al. |
| 7,607,965 B1 | 10/2009 | Frazier |
| 7,608,060 B2 | 10/2009 | Gillespie, Jr. et al. |
| 7,608,640 B2 | 10/2009 | Messadek |
| 7,618,615 B2 | 10/2009 | Frey, II et al. |
| 7,615,046 B2 | 11/2009 | Shehata |
| 7,618,369 B2 | 11/2009 | Hayter et al. |
| 7,618,954 B2 | 11/2009 | Nicolau et al. |
| 7,621,893 B2 | 11/2009 | Moberg et al. |
| 7,624,409 B2 | 11/2009 | Whymark |
| 7,625,354 B2 | 12/2009 | Hochman |
| 7,625,358 B2 | 12/2009 | Mernoe |
| 7,625,369 B2 | 12/2009 | Abboud et al. |
| 7,628,590 B2 | 12/2009 | Jacobsen et al. |
| 7,628,772 B2 | 12/2009 | McConnell et al. |
| 7,628,782 B2 | 12/2009 | Adair et al. |

(56) References Cited

U.S. PATENT DOCUMENTS

| | | | |
|---|---|---|---|
| 7,630,748 B2 | 12/2009 | Budiman |
| 7,630,773 B2 | 12/2009 | Seeberger et al. |
| 7,630,791 B2 | 12/2009 | Nguyen et al. |
| 7,632,228 B2 | 12/2009 | Brauker et al. |
| 7,632,247 B2 | 12/2009 | Adams |
| 7,632,248 B2 | 12/2009 | Delk et al. |
| 7,635,349 B2 | 12/2009 | Tribe et al. |
| 7,635,575 B2 | 12/2009 | Scherze et al. |
| 7,637,279 B2 | 12/2009 | Amley et al. |
| 7,637,931 B2 | 12/2009 | Heaton |
| 7,638,095 B2 | 12/2009 | Sabol |
| 7,641,649 B2 | 1/2010 | Moberg et al. |
| 7,642,232 B2 | 1/2010 | Green et al. |
| 7,644,203 B2 | 1/2010 | Ingles |
| 7,645,253 B2 | 1/2010 | Gura et al. |
| 7,645,264 B2 | 1/2010 | Marsh et al. |
| 7,647,107 B2 | 1/2010 | Warman et al. |
| 7,647,115 B2 | 1/2010 | Levin et al. |
| 7,647,237 B2 | 1/2010 | Malave et al. |
| 7,650,181 B2 | 1/2010 | Freeman et al. |
| 7,650,190 B2 | 1/2010 | Zhou et al. |
| 7,651,489 B2 | 1/2010 | Estes et al. |
| 7,651,868 B2 | 1/2010 | McDevitt et al. |
| 7,653,425 B2 | 1/2010 | Hayter et al. |
| 7,653,639 B2 | 1/2010 | Classen |
| 7,654,127 B2 | 2/2010 | Krulevitch et al. |
| 7,654,131 B2 | 2/2010 | Ascheman |
| 7,654,484 B2 | 2/2010 | Mogensen et al. |
| 7,654,976 B2 | 2/2010 | Peterson et al. |
| 7,654,982 B2 | 2/2010 | Carlisle et al. |
| 7,655,221 B2 | 2/2010 | Rasmussen et al. |
| 7,657,313 B2 | 2/2010 | Rom |
| 7,662,105 B2 | 2/2010 | Hatlestad |
| 7,662,140 B2 | 2/2010 | Heruth et al. |
| 7,662,558 B2 | 2/2010 | Liew |
| 7,668,731 B2 | 2/2010 | Martucci et al. |
| 7,674,243 B2 | 3/2010 | Dacquay et al. |
| 7,674,485 B2 | 3/2010 | Bhaskaran et al. |
| 7,676,263 B2 | 3/2010 | Harris et al. |
| 7,676,519 B2 | 3/2010 | McBride et al. |
| 7,678,071 B2 | 3/2010 | Lebel et al. |
| 7,678,084 B2 | 3/2010 | Judson et al. |
| 7,678,761 B2 | 3/2010 | Coleman |
| 7,678,762 B2 | 3/2010 | Green et al. |
| 7,678,763 B2 | 3/2010 | Green et al. |
| 7,678,772 B2 | 3/2010 | Jia et al. |
| 7,678,833 B2 | 3/2010 | Ott |
| 7,681,570 B2 | 3/2010 | Vedrine et al. |
| 7,682,338 B2 | 3/2010 | Griffin |
| 7,682,430 B2 | 3/2010 | Kraemer et al. |
| 7,682,563 B2 | 3/2010 | Carpenter et al. |
| 7,683,029 B2 | 3/2010 | Hindle et al. |
| 7,685,865 B2 | 3/2010 | Norenberg |
| 7,686,787 B2 | 3/2010 | Moberg et al. |
| 7,687,272 B1 | 3/2010 | Buchwald et al. |
| RE41,288 E | 4/2010 | Coolidge et al. |
| D613,411 S | 4/2010 | Collins et al. |
| 7,691,330 B1 | 4/2010 | Winkler et al. |
| 7,695,454 B2 | 4/2010 | Barron et al. |
| 7,695,627 B2 | 4/2010 | Bosch et al. |
| 7,697,967 B2 | 4/2010 | Stafford |
| 7,697,995 B2 | 4/2010 | Cross, Jr. et al. |
| 7,699,767 B2 | 4/2010 | Mueth et al. |
| 7,699,775 B2 | 4/2010 | Desai et al. |
| 7,699,808 B2 | 4/2010 | Marrs et al. |
| 7,699,833 B2 | 4/2010 | Moberg et al. |
| 7,704,226 B2 | 4/2010 | Mueller, Jr. et al. |
| 7,704,227 B2 | 4/2010 | Moberg et al. |
| 7,704,237 B2 | 4/2010 | Fisher et al. |
| 7,704,238 B2 | 4/2010 | Diller et al. |
| 7,708,717 B2 | 5/2010 | Estes et al. |
| 7,708,872 B2 | 5/2010 | Eidsned et al. |
| 7,708,915 B2 | 5/2010 | Castor |
| 7,713,238 B2 | 5/2010 | Mernoe |
| 7,713,240 B2 | 5/2010 | Istoc et al. |
| 7,713,262 B2 | 5/2010 | Adams et al. |
| 7,713,574 B2 | 5/2010 | Brister et al. |
| 7,714,757 B2 | 5/2010 | Denison et al. |
| 7,714,889 B2 | 5/2010 | Silverbrook |
| 7,715,917 B2 | 5/2010 | Chinchoy et al. |
| 7,716,964 B2 | 5/2010 | Kurtz et al. |
| 7,717,856 B2 | 5/2010 | Chen et al. |
| 7,717,871 B2 | 5/2010 | Odland |
| 7,717,903 B2 | 5/2010 | Estes et al. |
| 7,722,536 B2 | 5/2010 | Goodnow |
| 7,736,338 B2 | 5/2010 | Kavazov et al. |
| 7,726,955 B2 | 6/2010 | Ryser et al. |
| 7,727,148 B2 | 6/2010 | Talbot et al. |
| 7,727,181 B2 | 6/2010 | Rush |
| 7,734,323 B2 | 6/2010 | Blomquist et al. |
| 7,736,309 B2 | 6/2010 | Miller et al. |
| 7,736,344 B2 | 6/2010 | Moberg et al. |
| 7,737,581 B2 | 6/2010 | Spurlin et al. |
| 7,740,708 B2 | 6/2010 | Lofton et al. |
| 7,743,007 B2 | 6/2010 | Jung et al. |
| 7,744,554 B2 | 6/2010 | Howard |
| 7,744,589 B2 | 6/2010 | Mounce et al. |
| 7,749,528 B2 | 7/2010 | De Carvalho et al. |
| 7,751,907 B2 | 7/2010 | Blomquist et al. |
| 7,753,660 B2 | 7/2010 | Gray |
| 7,753,873 B2 | 7/2010 | Rush |
| 7,753,879 B2 | 7/2010 | Mernoe |
| 7,753,885 B2 | 7/2010 | Duchon et al. |
| 7,756,722 B2 | 7/2010 | Levine et al. |
| 7,758,547 B2 | 7/2010 | Tonelli |
| 7,758,568 B2 | 7/2010 | Olsen |
| 7,760,601 B2 | 7/2010 | Igi |
| 7,762,793 B2 | 7/2010 | Gray et al. |
| 7,766,301 B2 | 8/2010 | Gray et al. |
| 7,766,829 B2 | 8/2010 | Sloan et al. |
| 7,766,830 B2 | 8/2010 | Fox et al. |
| 7,766,831 B2 | 8/2010 | Essenpreis et al. |
| 7,766,863 B2 | 8/2010 | Gillespie, Jr. et al. |
| 7,766,873 B2 | 8/2010 | Moberg et al. |
| 7,768,386 B2 | 8/2010 | Hayter et al. |
| 7,768,408 B2 | 8/2010 | Reggiardo et al. |
| 7,771,385 B2 | 8/2010 | Eggers et al. |
| 7,771,386 B2 | 8/2010 | Eggers et al. |
| 7,771,414 B2 | 8/2010 | Trieu |
| 7,774,145 B2 | 8/2010 | Brauker et al. |
| 7,775,975 B2 | 8/2010 | Brister et al. |
| 7,776,006 B2 | 8/2010 | Childers et al. |
| 7,776,030 B2 | 8/2010 | Estes et al. |
| 7,776,031 B2 | 8/2010 | Hartlaub et al. |
| 7,778,680 B2 | 8/2010 | Goode, Jr. et al. |
| 7,779,183 B2 | 8/2010 | Koehler et al. |
| 7,780,981 B2 | 8/2010 | DiPierro et al. |
| 7,782,192 B2 | 8/2010 | Jeckelmann et al. |
| 7,785,288 B2 | 8/2010 | Mernoe et al. |
| 7,785,293 B2 | 8/2010 | Gray et al. |
| 7,785,313 B2 | 8/2010 | Mastrototaro |
| 7,788,369 B2 | 8/2010 | McAllen et al. |
| 7,789,849 B2 | 9/2010 | Busby et al. |
| 7,789,857 B2 | 9/2010 | Moberg et al. |
| 7,790,103 B2 | 9/2010 | Shah et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,794,434 B2 | 9/2010 | Mounce et al. |
| 7,797,028 B2 | 9/2010 | Goode, Jr. et al. |
| 7,797,649 B1 | 9/2010 | Etawil et al. |
| 7,801,582 B2 | 9/2010 | Peyser |
| 7,806,853 B2 | 10/2010 | Wittmann et al. |
| 7,806,854 B2 | 10/2010 | Damiano et al. |
| 7,806,867 B2 | 10/2010 | Willis et al. |
| 7,806,868 B2 | 10/2010 | De Polo et al. |
| 7,806,886 B2 | 10/2010 | Kanderian, Jr. et al. |
| 7,811,231 B2 | 10/2010 | Jin et al. |
| 7,811,246 B2 | 10/2010 | Koops |
| 7,811,262 B2 | 10/2010 | Moberg et al. |
| 7,811,279 B2 | 10/2010 | John |
| 7,815,595 B2 | 10/2010 | Busby et al. |
| 7,815,602 B2 | 10/2010 | Mann et al. |
| 7,815,609 B2 | 10/2010 | Hines et al. |

(56) References Cited

U.S. PATENT DOCUMENTS

| | | |
|---|---|---|
| 7,815,622 B2 | 10/2010 | Istoc |
| 7,819,843 B2 | 10/2010 | Mann et al. |
| 7,822,455 B2 | 10/2010 | Hoss et al. |
| RE41,956 E | 11/2010 | Klitgaard et al. |
| 7,826,382 B2 | 11/2010 | Sicurello et al. |
| 7,826,879 B2 | 11/2010 | Hoss et al. |
| 7,828,528 B2 | 11/2010 | Estes et al. |
| 7,828,747 B2 | 11/2010 | Heske et al. |
| 7,828,764 B2 | 11/2010 | Moberg et al. |
| 7,828,771 B2 | 11/2010 | Chiang et al. |
| 7,831,310 B2 | 11/2010 | Lebel et al. |
| 7,833,196 B2 | 11/2010 | Estes et al. |
| 7,835,927 B2 | 11/2010 | Schlotterbeck et al. |
| 7,837,647 B2 | 11/2010 | Estes et al. |
| 7,837,648 B2 | 11/2010 | Blair et al. |
| 7,837,651 B2 | 11/2010 | Bishop et al. |
| 7,849,872 B2 | 12/2010 | Phillips et al. |
| 7,850,641 B2 | 12/2010 | Lebel et al. |
| 7,850,658 B2 | 12/2010 | Faust et al. |
| 7,850,674 B2 | 12/2010 | Goodnow et al. |
| 7,851,509 B2 | 12/2010 | Miller et al. |
| 7,857,756 B2 | 12/2010 | Warren et al. |
| 7,857,791 B2 | 12/2010 | Jacobs et al. |
| 7,860,544 B2 | 12/2010 | Say et al. |
| 7,860,583 B2 | 12/2010 | Condurso et al. |
| 7,867,189 B2 | 1/2011 | Childers et al. |
| 7,869,853 B1 | 1/2011 | Say et al. |
| 7,874,718 B2 | 1/2011 | Demers et al. |
| 7,875,022 B2 | 1/2011 | Wenger et al. |
| 7,877,489 B2 | 1/2011 | Salesky et al. |
| 7,877,703 B1 | 1/2011 | Fleming |
| 7,879,026 B2 | 2/2011 | Estes et al. |
| 7,881,883 B2 | 2/2011 | Remde |
| 7,882,611 B2 | 2/2011 | Shah et al. |
| 7,883,464 B2 | 2/2011 | Stafford |
| 7,884,729 B2 | 2/2011 | Reggiardo et al. |
| 7,885,699 B2 | 2/2011 | Say et al. |
| 7,887,505 B2 | 2/2011 | Flaherty |
| 7,887,511 B2 | 2/2011 | Mernoe et al. |
| 7,887,512 B2 | 2/2011 | Estes et al. |
| 7,890,295 B2 | 2/2011 | Shin et al. |
| 7,892,199 B2 | 2/2011 | Mhatre et al. |
| 7,892,206 B2 | 2/2011 | Moberg et al. |
| 7,896,842 B2 | 3/2011 | Palmroos et al. |
| 7,901,394 B2 | 3/2011 | Ireland et al. |
| 7,905,710 B2 | 3/2011 | Wang et al. |
| 7,905,859 B2 | 3/2011 | Bynum et al. |
| 7,905,866 B2 | 3/2011 | Haider et al. |
| 7,905,868 B2 | 3/2011 | Moberg et al. |
| 7,912,674 B2 | 3/2011 | Redl et al. |
| 7,914,499 B2 | 3/2011 | Gonneli et al. |
| 7,914,500 B2 | 3/2011 | Gafner-geiser et al. |
| 7,914,742 B2 | 3/2011 | Arbogast et al. |
| 7,917,186 B2 | 3/2011 | Kamath et al. |
| 7,918,825 B2 | 4/2011 | O'connor et al. |
| 7,919,063 B2 | 4/2011 | Sarofim |
| 7,920,907 B2 | 4/2011 | Mcgarraugh et al. |
| 7,922,096 B2 | 4/2011 | Eilersen |
| 7,922,458 B2 | 4/2011 | Rush et al. |
| 7,922,462 B2 | 4/2011 | Preuthun et al. |
| 7,928,850 B2 | 4/2011 | Hayter et al. |
| 7,931,592 B2 | 4/2011 | Currie et al. |
| 7,931,613 B2 | 4/2011 | Haueter et al. |
| 7,931,642 B2 | 4/2011 | Tonnies |
| 7,931,864 B2 | 4/2011 | Kloepfer et al. |
| 7,933,639 B2 | 4/2011 | Goode et al. |
| 7,933,780 B2 | 4/2011 | De La Huerga |
| 7,935,074 B2 | 5/2011 | Plahey et al. |
| 7,935,076 B2 | 5/2011 | Estes et al. |
| 7,935,079 B2 | 5/2011 | Ludin et al. |
| 7,935,104 B2 | 5/2011 | Yodfat et al. |
| 7,935,105 B2 | 5/2011 | Miller et al. |
| 7,935,499 B2 | 5/2011 | Dunn et al. |
| 7,937,163 B2 | 5/2011 | Sekiguchi |
| 7,938,792 B2 | 5/2011 | Roger et al. |
| 7,938,797 B2 | 5/2011 | Estes et al. |
| 7,938,802 B2 | 5/2011 | Bicknell et al. |
| 7,938,803 B2 | 5/2011 | Mernoe et al. |
| 7,941,200 B2 | 5/2011 | Weinert et al. |
| 7,942,069 B2 | 5/2011 | Peterson |
| 7,942,844 B2 | 5/2011 | Moberg et al. |
| 7,944,366 B2 | 5/2011 | Krulevitch et al. |
| 7,945,452 B2 | 5/2011 | Fathallah et al. |
| 7,946,985 B2 | 5/2011 | Mastrototaro et al. |
| 7,948,370 B2 | 5/2011 | Reggiardo et al. |
| 7,951,112 B2 | 5/2011 | Patzer |
| 7,951,114 B2 | 5/2011 | Rush et al. |
| 7,951,122 B2 | 5/2011 | Shekalim |
| 7,955,261 B2 | 6/2011 | Goode et al. |
| 7,955,305 B2 | 6/2011 | Moberg et al. |
| 7,955,319 B2 | 6/2011 | Miesel |
| 7,955,843 B2 | 6/2011 | Barringer, Jr. |
| 7,957,984 B1 | 6/2011 | Vallone |
| 7,959,569 B2 | 6/2011 | Goode et al. |
| 7,959,598 B2 | 6/2011 | Estes et al. |
| 7,959,608 B2 | 6/2011 | Nash et al. |
| 7,959,715 B2 | 6/2011 | Kavazov et al. |
| 7,959,938 B2 | 6/2011 | Rohloff et al. |
| 7,963,945 B2 | 6/2011 | Miller et al. |
| 7,963,946 B2 | 6/2011 | Moubayed et al. |
| 7,963,954 B2 | 6/2011 | Kavazov et al. |
| 7,964,555 B2 | 6/2011 | Zhou |
| 7,967,010 B2 | 6/2011 | Vedrine et al. |
| 7,967,022 B2 | 6/2011 | Grant et al. |
| 7,967,740 B2 | 6/2011 | Mertens et al. |
| 7,967,752 B2 | 6/2011 | Oevirk et al. |
| 7,967,773 B2 | 6/2011 | Amnorn et al. |
| 7,967,785 B2 | 6/2011 | Morgan et al. |
| 7,967,806 B2 | 6/2011 | Jasperson et al. |
| 7,967,810 B2 | 6/2011 | Freedman et al. |
| 7,967,812 B2 | 6/2011 | Jasperson et al. |
| 7,970,620 B2 | 6/2011 | Brown |
| 7,955,295 B2 | 7/2011 | Lee et al. |
| 7,972,286 B2 | 7/2011 | Prausnitz et al. |
| 7,972,296 B2 | 7/2011 | Braig et al. |
| 7,972,302 B2 | 7/2011 | Caizza et al. |
| 7,972,303 B2 | 7/2011 | Caizza et al. |
| 7,972,304 B2 | 7/2011 | Caizza et al. |
| 7,973,667 B2 | 7/2011 | Crnkovich et al. |
| 7,976,478 B2 | 7/2011 | Fujiwara et al. |
| 7,976,492 B2 | 7/2011 | Brauker et al. |
| 7,976,493 B2 | 7/2011 | Carter et al. |
| 7,976,499 B2 | 7/2011 | Grunhut et al. |
| 7,976,500 B2 | 7/2011 | Adams et al. |
| 7,976,505 B2 | 7/2011 | Hines et al. |
| 7,976,508 B2 | 7/2011 | Hoag |
| 7,976,514 B2 | 7/2011 | Abry et al. |
| 7,976,530 B2 | 7/2011 | Johnson et al. |
| 7,976,778 B2 | 7/2011 | Drucker et al. |
| 7,976,865 B2 | 7/2011 | Kawamura et al. |
| 7,976,870 B2 | 7/2011 | Berner et al. |
| 7,979,104 B2 | 7/2011 | Kamath et al. |
| 7,979,136 B2 | 7/2011 | Young et al. |
| 7,981,034 B2 | 7/2011 | Jennewine et al. |
| 7,981,042 B2 | 7/2011 | Stahmann et al. |
| 7,981,076 B2 | 7/2011 | Sullivan et al. |
| 7,981,081 B2 | 7/2011 | Marsh et al. |
| 7,981,084 B2 | 7/2011 | Estes et al. |
| 7,981,090 B2 | 7/2011 | Plishka et al. |
| 7,981,102 B2 | 7/2011 | Patel et al. |
| 7,981,105 B2 | 7/2011 | Adair et al. |
| 7,981,107 B2 | 7/2011 | Olsen |
| 7,983,745 B2 | 7/2011 | Hatlestad et al. |
| 7,985,057 B2 | 7/2011 | Haar |
| 7,985,330 B2 | 7/2011 | Wang et al. |
| 7,986,986 B2 | 7/2011 | Goode et al. |
| 7,988,630 B1 | 8/2011 | Osorio et al. |
| 7,988,660 B2 | 8/2011 | Byland et al. |
| 7,988,663 B2 | 8/2011 | Schiller et al. |
| 7,988,674 B2 | 8/2011 | Adams et al. |
| 7,988,687 B2 | 8/2011 | Friedli |
| 7,988,849 B2 | 8/2011 | Biewer et al. |
| 7,988,850 B2 | 8/2011 | Roncadi et al. |
| 7,990,251 B1 | 8/2011 | Ford, Jr. |

(56) References Cited

U.S. PATENT DOCUMENTS

| | | |
|---|---|---|
| 7,993,108 B2 | 8/2011 | Rush et al. |
| 7,993,140 B2 | 8/2011 | Sakezles |
| 7,993,300 B2 | 8/2011 | Nyholm et al. |
| 7,993,306 B2 | 8/2011 | Marrs et al. |
| 7,996,158 B2 | 8/2011 | Hayter et al. |
| 7,998,110 B2 | 8/2011 | Leung et al. |
| 7,998,111 B2 | 8/2011 | Moberg et al. |
| 7,998,117 B2 | 8/2011 | Gross et al. |
| 7,999,674 B2 | 8/2011 | Kamen |
| 7,999,927 B2 | 8/2011 | Braig et al. |
| 8,000,763 B2 | 8/2011 | Mazza et al. |
| 8,002,700 B2 | 8/2011 | Ferek-Petric et al. |
| 8,002,747 B2 | 8/2011 | Lord et al. |
| 8,003,630 B2 | 8/2011 | Zagon et al. |
| 8,005,524 B2 | 8/2011 | Brauker et al. |
| 8,005,540 B2 | 8/2011 | Zhang et al. |
| 8,005,688 B2 | 8/2011 | Coffman et al. |
| 8,007,460 B2 | 8/2011 | Gelfand et al. |
| 8,007,487 B2 | 8/2011 | Patrick et al. |
| 8,007,724 B2 | 8/2011 | Guzman |
| RE42,682 E | 9/2011 | Barreras, Sr. et al. |
| 8,011,039 B2 | 9/2011 | Stryker et al. |
| 8,012,104 B2 | 9/2011 | Escutia et al. |
| 8,012,114 B2 | 9/2011 | Daniel et al. |
| 8,012,119 B2 | 9/2011 | Estes et al. |
| 8,012,121 B2 | 9/2011 | Goodson, IV et al. |
| 8,012,132 B2 | 9/2011 | Lum et al. |
| 8,014,857 B2 | 9/2011 | Doerr |
| 8,016,740 B2 | 9/2011 | Connors et al. |
| 8,016,772 B2 | 9/2011 | Keske et al. |
| 8,016,783 B2 | 9/2011 | Pastore et al. |
| 8,016,789 B2 | 9/2011 | Grant et al. |
| 8,016,812 B2 | 9/2011 | Koh |
| 8,016,859 B2 | 9/2011 | Donofrio et al. |
| 8,019,421 B2 | 9/2011 | Young et al. |
| 8,020,564 B2 | 9/2011 | Batch |
| 8,021,299 B2 | 9/2011 | Miesel et al. |
| 8,021,334 B2 | 9/2011 | Shekalim |
| 8,021,680 B2 | 9/2011 | Anderson et al. |
| 8,022,042 B2 | 9/2011 | Ko |
| 8,022,366 B2 | 9/2011 | Hartley |
| 8,025,634 B1 | 9/2011 | Moubayed et al. |
| 8,026,209 B2 | 9/2011 | Gaillard et al. |
| 8,026,215 B2 | 9/2011 | Unemori |
| 8,026,227 B2 | 9/2011 | Hausheer |
| 8,027,740 B2 | 9/2011 | Altman et al. |
| 8,029,245 B2 | 10/2011 | Rush et al. |
| 8,029,250 B2 | 10/2011 | Rush et al. |
| 8,029,454 B2 | 10/2011 | Kelly et al. |
| 8,029,459 B2 | 10/2011 | Rush et al. |
| 8,029,460 B2 | 10/2011 | Rush et al. |
| 8,030,058 B1 | 10/2011 | Benedict et al. |
| 8,030,802 B2 | 10/2011 | Lindegger et al. |
| 8,030,891 B2 | 10/2011 | Welsch et al. |
| 8,032,226 B2 | 10/2011 | Miller et al. |
| 8,034,015 B2 | 10/2011 | Braig et al. |
| 8,034,019 B2 | 10/2011 | Nair et al. |
| 8,034,026 B2 | 10/2011 | Grant et al. |
| 8,034,793 B2 | 10/2011 | Heidenreich et al. |
| 8,038,650 B2 | 10/2011 | Shekalim |
| 8,038,709 B2 | 10/2011 | Palasis et al. |
| 8,043,074 B2 | 10/2011 | Tada |
| 8,043,258 B2 | 10/2011 | Ostroot |
| 8,043,277 B2 | 10/2011 | Junker |
| 8,043,281 B2 | 10/2011 | Heruth et al. |
| 8,043,744 B2 | 10/2011 | Traulsen et al. |
| 8,046,043 B2 | 10/2011 | Asano et al. |
| RE42,958 E | 11/2011 | Loeb et al. |
| 8,047,202 B2 | 11/2011 | Djupesland |
| 8,047,811 B2 | 11/2011 | Rush et al. |
| 8,047,812 B2 | 11/2011 | Rush et al. |
| 8,047,819 B2 | 11/2011 | Lawrence et al. |
| 8,048,041 B2 | 11/2011 | Cefai et al. |
| 8,048,619 B2 | 11/2011 | Chow |
| 8,049,059 B2 | 11/2011 | Bleyer et al. |
| 8,050,729 B2 | 11/2011 | Shekalim |
| 8,052,614 B2 | 11/2011 | Heske et al. |
| 8,053,429 B2 | 11/2011 | Cumming et al. |
| 8,056,582 B2 | 11/2011 | DiPerna |
| 8,057,156 B2 | 11/2011 | List |
| 8,057,426 B2 | 11/2011 | Nayak et al. |
| 8,057,679 B2 | 11/2011 | Yu et al. |
| 8,060,185 B2 | 11/2011 | Hunter et al. |
| 8,060,209 B2 | 11/2011 | Jaax et al. |
| 8,062,249 B2 | 11/2011 | Wilinska et al. |
| 8,062,256 B2 | 11/2011 | Carter et al. |
| 8,062,257 B2 | 11/2011 | Moberg et al. |
| 8,062,264 B2 | 11/2011 | Godfrey et al. |
| 8,065,096 B2 | 11/2011 | Moberg et al. |
| 8,065,161 B2 | 11/2011 | Howard et al. |
| 8,066,197 B2 | 11/2011 | Sheppard |
| 8,066,198 B2 | 11/2011 | Palanchon et al. |
| 8,066,629 B2 | 11/2011 | Dlugos |
| 8,066,665 B2 | 11/2011 | Rush et al. |
| 8,066,668 B2 | 11/2011 | Wayman et al. |
| 8,066,671 B2 | 11/2011 | Busby et al. |
| 8,066,680 B2 | 11/2011 | Alchas et al. |
| 8,066,688 B2 | 11/2011 | Zinger et al. |
| 8,066,940 B2 | 11/2011 | Denkewicz, Jr. et al. |
| 8,067,031 B2 | 11/2011 | Daniloff et al. |
| 8,067,173 B2 | 11/2011 | Liew |
| 8,070,723 B2 | 12/2011 | Bazargan et al. |
| 8,070,726 B2 | 12/2011 | Gonnelli et al. |
| 8,070,741 B2 | 12/2011 | Barrelle et al. |
| 8,070,742 B2 | 12/2011 | Woo |
| 8,071,075 B2 | 12/2011 | Reed et al. |
| 8,071,722 B2 | 12/2011 | Kaplan et al. |
| 8,073,543 B2 | 12/2011 | Pyles |
| 8,073,549 B2 | 12/2011 | Chen |
| 8,075,503 B2 | 12/2011 | Jaeb |
| 8,075,522 B2 | 12/2011 | Larsen et al. |
| 8,075,527 B2 | 12/2011 | Rush et al. |
| 8,075,919 B2 | 12/2011 | Brown et al. |
| 8,078,983 B2 | 12/2011 | Davis et al. |
| 8,079,983 B2 | 12/2011 | Rush et al. |
| 8,079,984 B2 | 12/2011 | Rush et al. |
| 8,080,002 B2 | 12/2011 | Stergiopulos et al. |
| 8,081,069 B2 | 12/2011 | Haueter et al. |
| 8,082,041 B1 | 12/2011 | Radziemski |
| 8,083,209 B2 | 12/2011 | Kozdras et al. |
| 8,083,711 B2 | 12/2011 | Enggaard |
| 8,083,718 B2 | 12/2011 | Rush et al. |
| 8,083,720 B2 | 12/2011 | Solar et al. |
| 8,083,722 B2 | 12/2011 | McKay |
| 8,083,730 B2 | 12/2011 | Miesel |
| 8,088,098 B2 | 1/2012 | Yodfat et al. |
| 8,088,789 B2 | 1/2012 | Yan et al. |
| 8,089,787 B2 | 1/2012 | Melse |
| 8,090,430 B2 | 1/2012 | Makower et al. |
| 8,090,435 B2 | 1/2012 | Gill et al. |
| 8,092,428 B2 | 1/2012 | Ramey et al. |
| 8,093,038 B2 | 1/2012 | Hatziavramidis |
| 8,093,212 B2 | 1/2012 | Gardner et al. |
| 8,093,214 B2 | 1/2012 | Crockford |
| 8,093,781 B2 | 1/2012 | Chiang et al. |
| 8,094,009 B2 | 1/2012 | Allen et al. |
| 8,095,197 B2 | 1/2012 | Santini, Jr. et al. |
| 8,096,329 B2 | 1/2012 | Thuot et al. |
| 8,096,487 B2 | 1/2012 | Hornsby |
| 8,096,972 B2 | 1/2012 | Varner et al. |
| 8,096,983 B2 | 1/2012 | Uchino et al. |
| 8,099,800 B2 | 1/2012 | Sawalski et al. |
| 8,100,842 B2 | 1/2012 | Rousso |
| 8,100,852 B2 | 1/2012 | Moberg et al. |
| 8,100,871 B2 | 1/2012 | Haase |
| 8,101,358 B2 | 1/2012 | Liew |
| 8,101,402 B2 | 1/2012 | Holmes |
| 8,101,727 B2 | 1/2012 | Stover et al. |
| 8,105,265 B2 | 1/2012 | Demers et al. |
| 8,105,268 B2 | 1/2012 | Lebel et al. |
| 8,105,269 B2 | 1/2012 | Zhou |
| 8,105,279 B2 | 1/2012 | Mernoe et al. |
| 8,105,280 B2 | 1/2012 | Iddan et al. |
| 8,105,351 B2 | 1/2012 | Lehman et al. |

(56) References Cited

U.S. PATENT DOCUMENTS

| | | |
|---|---|---|
| 8,106,534 B2 | 1/2012 | Spurlin et al. |
| 8,108,051 B2 | 1/2012 | Cross, Jr. et al. |
| 8,109,893 B2 | 2/2012 | Lande |
| 8,109,906 B2 | 2/2012 | Smisson et al. |
| 8,109,912 B2 | 2/2012 | Alferness et al. |
| 8,109,921 B2 | 2/2012 | Estes et al. |
| 8,110,224 B2 | 2/2012 | Ausborn et al. |
| 8,110,358 B2 | 2/2012 | Liew |
| 8,110,555 B2 | 2/2012 | Jia et al. |
| 8,112,287 B1 | 2/2012 | Paul et al. |
| 8,112,288 B1 | 2/2012 | Paul et al. |
| 8,114,023 B2 | 2/2012 | Ward et al. |
| 8,114,056 B2 | 2/2012 | Niklaus et al. |
| 8,114,064 B2 | 2/2012 | Alferness et al. |
| 8,114,350 B1 | 2/2012 | Silver et al. |
| 8,114,430 B2 | 2/2012 | Rohloff et al. |
| 8,114,597 B2 | 2/2012 | Liew |
| 8,115,600 B2 | 2/2012 | Stevenson et al. |
| 8,116,862 B2 | 2/2012 | Stevenson et al. |
| 8,118,571 B2 | 2/2012 | Krisher |
| 8,118,770 B2 | 2/2012 | Galley et al. |
| 8,118,782 B2 | 2/2012 | Remde |
| 8,119,159 B2 | 2/2012 | Cumming et al. |
| 8,119,593 B2 | 2/2012 | Richardson et al. |
| 8,121,857 B2 | 2/2012 | Galasso et al. |
| 8,123,717 B2 | 2/2012 | Weinert et al. |
| 8,123,720 B2 | 2/2012 | Solomon |
| 8,124,689 B2 | 2/2012 | Loubert et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,127,046 B2 | 2/2012 | Grant et al. |
| 8,128,589 B2 | 3/2012 | Freeman et al. |
| 8,128,597 B2 | 3/2012 | Cross et al. |
| 8,128,946 B2 | 3/2012 | Kawamura et al. |
| 8,129,429 B2 | 3/2012 | Sporn et al. |
| 8,130,095 B2 | 3/2012 | Allen et al. |
| 8,147,451 B2 | 4/2012 | Brockman et al. |
| 8,147,511 B2 | 4/2012 | Perry |
| 8,149,131 B2 | 4/2012 | Blomquist |
| 8,152,764 B2 | 4/2012 | Istoc et al. |
| 8,156,070 B2 | 4/2012 | Buck |
| 8,167,832 B2 | 5/2012 | Bowman |
| 8,172,082 B2 | 5/2012 | Edwards |
| 8,172,798 B2 | 5/2012 | Hungerford |
| 8,177,739 B2 | 5/2012 | Cartledge |
| 8,182,447 B2 | 5/2012 | Moberg et al. |
| 8,182,461 B2 | 5/2012 | Pope et al. |
| 8,182,462 B2 | 5/2012 | Istoc et al. |
| 8,187,228 B2 | 5/2012 | Bikovsky |
| 8,192,394 B2 | 6/2012 | Estes et al. |
| 8,202,267 B2 | 6/2012 | Field et al. |
| 8,206,296 B2 | 6/2012 | Jennewine |
| 8,206,350 B2 | 6/2012 | Mann et al. |
| 8,206,378 B1 | 6/2012 | Kalpin et al. |
| 8,211,062 B2 | 7/2012 | Estes et al. |
| 8,211,093 B2 | 7/2012 | Miller et al. |
| 8,211,364 B2 | 7/2012 | Drucker et al. |
| 8,223,028 B2 | 7/2012 | Mandro et al. |
| 8,231,562 B2 | 7/2012 | Buck et al. |
| 8,231,572 B2 | 7/2012 | Carter et al. |
| 8,231,578 B2 | 7/2012 | Fathallah et al. |
| 8,234,126 B1 | 7/2012 | Estes |
| 8,234,128 B2 | 7/2012 | Martucci et al. |
| 8,237,715 B2 | 8/2012 | Buck et al. |
| 8,257,652 B2 | 9/2012 | Drucker et al. |
| 8,257,653 B2 | 9/2012 | Drucker et al. |
| 8,267,892 B2 | 9/2012 | Spencer et al. |
| 8,267,893 B2 | 9/2012 | Moberg et al. |
| 8,282,601 B2 | 10/2012 | Mernoe et al. |
| 8,285,328 B2 | 10/2012 | Caffey et al. |
| 8,287,454 B2 | 10/2012 | Wolpert et al. |
| 8,287,495 B2 | 10/2012 | Michaud et al. |
| 8,287,514 B2 | 10/2012 | Miller et al. |
| 8,287,521 B2 | 10/2012 | Kriesel et al. |
| 8,292,876 B2 | 10/2012 | Kriesel et al. |
| 8,298,183 B2 | 10/2012 | Menot et al. |
| 8,298,184 B2 | 10/2012 | DiPerna et al. |
| 8,310,415 B2 | 11/2012 | Mclaughlin et al. |
| 8,317,752 B2 | 11/2012 | Cozmi et al. |
| 8,323,188 B2 | 12/2012 | Tran |
| 8,328,754 B2 | 12/2012 | Estes et al. |
| 8,328,793 B2 | 12/2012 | Birkenbach et al. |
| 8,344,847 B2 | 1/2013 | Moberg et al. |
| 8,348,886 B2 | 1/2013 | Kanderian et al. |
| 8,348,923 B2 | 1/2013 | Kanderian et al. |
| 8,361,030 B2 | 1/2013 | Carter |
| 8,372,040 B2 | 2/2013 | Huang et al. |
| 8,376,943 B2 | 2/2013 | Kovach et al. |
| 8,380,536 B2 | 2/2013 | Howard et al. |
| 8,395,581 B2 | 3/2013 | Graskov |
| 8,398,592 B2 | 3/2013 | Leibner-Druska |
| 8,407,063 B2 | 3/2013 | Brown |
| 8,408,421 B2 | 4/2013 | DiPerna |
| 8,414,532 B2 | 4/2013 | Brandt et al. |
| 8,414,536 B2 | 4/2013 | Grant et al. |
| 8,414,557 B2 | 4/2013 | Istoc |
| 8,414,563 B2 | 4/2013 | Kamen |
| 8,435,206 B2 | 5/2013 | Evans et al. |
| 8,444,592 B2 | 5/2013 | Williams et al. |
| 8,444,595 B2 | 5/2013 | Brukalo et al. |
| 8,448,824 B2 | 5/2013 | DiPerna |
| 8,449,523 B2 | 5/2013 | Brukalo et al. |
| 8,449,524 B2 | 5/2013 | Braig et al. |
| 8,451,230 B2 | 5/2013 | Celentano et al. |
| 8,454,562 B1 | 6/2013 | Sims |
| 8,454,575 B2 | 6/2013 | Estes et al. |
| 8,517,987 B2 | 8/2013 | Istoc |
| 8,524,154 B2 | 9/2013 | Shekalim et al. |
| 8,562,590 B2 | 10/2013 | Yodfat |
| 8,573,027 B2 | 11/2013 | Rosinko et al. |
| 8,608,699 B2 | 12/2013 | Blomquist |
| 8,641,671 B2 | 2/2014 | Michaud et al. |
| 8,694,331 B2 | 4/2014 | Olsen |
| 8,758,323 B2 | 6/2014 | Michaud et al. |
| 8,926,561 B2 | 1/2015 | Verhoef et al. |
| 8,938,306 B2 | 1/2015 | Lebel |
| 8,986,253 B2 | 3/2015 | DiPerna |
| 9,049,982 B2 | 6/2015 | Brukalo |
| 9,173,998 B2 | 11/2015 | Rosinko et al. |
| 9,180,242 B2 * | 11/2015 | Metzmaker ............ A61J 1/2096 |
| 9,180,243 B2 | 11/2015 | Michaud |
| 9,194,383 B2 | 11/2015 | Knobel |
| 9,211,377 B2 | 12/2015 | Diperna et al. |
| 9,421,329 B2 | 8/2016 | Kruse |
| 2001/0000282 A1 | 4/2001 | Poleshuk et al. |
| 2001/0027791 A1 | 10/2001 | Wallace et al. |
| 2001/0041869 A1 | 11/2001 | James, III et al. |
| 2002/0004015 A1 | 1/2002 | Carlisle et al. |
| 2002/0018720 A1 | 2/2002 | Carlisle et al. |
| 2002/0019714 A1 | 2/2002 | Carlisle et al. |
| 2002/0029776 A1 | 3/2002 | Blomquist |
| 2002/0040208 A1 | 4/2002 | Flaherty et al. |
| 2002/0045265 A1 | 4/2002 | Bergh et al. |
| 2002/0048536 A1 | 4/2002 | Bergh et al. |
| 2002/0055787 A1 | 5/2002 | Lennox et al. |
| 2002/0059959 A1 | 5/2002 | Qatu et al. |
| 2002/0065484 A1 | 5/2002 | Douglas et al. |
| 2002/0072733 A1 | 6/2002 | Flaherty |
| 2002/0076679 A1 | 6/2002 | Aman |
| 2002/0117214 A1 | 8/2002 | Tucker et al. |
| 2002/0120234 A1 | 8/2002 | Kong |
| 2002/0154571 A1 | 10/2002 | Cefai et al. |
| 2002/0173769 A1 | 11/2002 | Gray et al. |
| 2003/0014016 A1 | 1/2003 | Purdy |
| 2003/0032930 A1 | 2/2003 | Branch et al. |
| 2003/0036725 A1 | 2/2003 | Lavi et al. |
| 2003/0055380 A1 | 3/2003 | Flaherty |
| 2003/0060765 A1 | 3/2003 | Campbell et al. |
| 2003/0183289 A1 | 3/2003 | Seuret et al. |
| 2003/0065308 A1 | 4/2003 | Lebel et al. |

(56) References Cited

U.S. PATENT DOCUMENTS

| | | |
|---|---|---|
| 2003/0078547 A1 | 4/2003 | Shekalim |
| 2003/0093105 A1 | 5/2003 | Huffmaster |
| 2003/0097082 A1 | 5/2003 | Purdy et al. |
| 2003/0100863 A1 | 5/2003 | Shekalim |
| 2003/0109836 A1 | 6/2003 | Shekalim |
| 2003/0130577 A1 | 7/2003 | Purdy et al. |
| 2003/0161744 A1 | 8/2003 | Vilks et al. |
| 2003/0163088 A1 | 8/2003 | Blomquist |
| 2003/0163789 A1 | 8/2003 | Blomquist |
| 2003/0199378 A1 | 10/2003 | Saviano |
| 2003/0212364 A1 | 11/2003 | Mann et al. |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0051368 A1 | 3/2004 | Caputo |
| 2004/0068230 A1 | 4/2004 | Estes et al. |
| 2004/0073095 A1 | 4/2004 | Causey, III et al. |
| 2004/0073161 A1 | 4/2004 | Tachibana |
| 2004/0074785 A1 | 4/2004 | Holker et al. |
| 2004/0078028 A1 | 4/2004 | Flaherty et al. |
| 2004/0092865 A1 | 5/2004 | Flaherty et al. |
| 2004/0116866 A1 | 6/2004 | Gorman et al. |
| 2004/0116905 A1 | 6/2004 | Pederson et al. |
| 2004/0122353 A1 | 6/2004 | Shahmirian et al. |
| 2004/0133166 A1 | 7/2004 | Moberg et al. |
| 2004/0133220 A1 | 7/2004 | Lashinski et al. |
| 2004/0138744 A1 | 7/2004 | Lashinski et al. |
| 2004/0153146 A1 | 8/2004 | Lashinski et al. |
| 2004/0167478 A1 | 8/2004 | Mooney et al. |
| 2004/0171987 A1 | 9/2004 | Bridle et al. |
| 2004/0176727 A1 | 9/2004 | Shekalim |
| 2004/0193090 A1 | 9/2004 | Lebel et al. |
| 2004/0204673 A1 | 10/2004 | Flaherty |
| 2004/0220551 A1 | 11/2004 | Flaherty et al. |
| 2004/0225252 A1 | 11/2004 | Gillespie et al. |
| 2004/0235446 A1 | 11/2004 | Flaherty et al. |
| 2004/0260233 A1 | 12/2004 | Garibotto et al. |
| 2005/0004514 A1 | 1/2005 | Hochman |
| 2005/0020980 A1 | 1/2005 | Campbell et al. |
| 2005/0022274 A1 | 1/2005 | Campbell et al. |
| 2005/0027182 A1 | 2/2005 | Siddiqui et al. |
| 2005/0038379 A1 | 2/2005 | Beebe et al. |
| 2005/0043710 A1 | 2/2005 | Hadzic et al. |
| 2005/0054994 A1 | 3/2005 | Cioanta et al. |
| 2005/0065464 A1 | 3/2005 | Talbot et al. |
| 2005/0060030 A1 | 5/2005 | Lashinski et al. |
| 2005/0096593 A1 | 5/2005 | Pope et al. |
| 2005/0115622 A1 | 6/2005 | Bennett et al. |
| 2005/0137530 A1 | 6/2005 | Campbell et al. |
| 2005/0137578 A1 | 6/2005 | Heruth et al. |
| 2005/0143864 A1 | 6/2005 | Blomquist |
| 2005/0148832 A1 | 7/2005 | Reghabi et al. |
| 2005/0171512 A1 | 8/2005 | Flaherty |
| 2005/0171513 A1 | 8/2005 | Mann et al. |
| 2005/0171569 A1 | 8/2005 | Girard et al. |
| 2005/0177395 A1 | 8/2005 | Blomquist |
| 2005/0182366 A1 | 8/2005 | Vogt et al. |
| 2005/0211322 A1 | 9/2005 | Lohbeck |
| 2005/0238507 A1 | 10/2005 | Dilanni et al. |
| 2005/0240092 A1 | 10/2005 | Shah et al. |
| 2005/0240119 A1 | 10/2005 | Draudt et al. |
| 2005/0245867 A1 | 11/2005 | Olsen et al. |
| 2005/0246416 A1 | 11/2005 | Blomquist |
| 2005/0267550 A1 | 12/2005 | Hess et al. |
| 2005/0272989 A1 | 12/2005 | Shah et al. |
| 2006/0031094 A1 | 2/2006 | Cohen et al. |
| 2006/0041229 A1 | 2/2006 | Garibotto et al. |
| 2006/0042695 A1 | 3/2006 | Gonia |
| 2006/0076236 A1 | 4/2006 | Shah et al. |
| 2006/0206054 A1 | 4/2006 | Shekalim et al. |
| 2006/0116757 A1 | 6/2006 | Lashinski et al. |
| 2006/0139354 A1 | 6/2006 | Suma |
| 2006/0147313 A1 | 7/2006 | Zengerle et al. |
| 2006/0149214 A1 | 7/2006 | Breiter et al. |
| 2006/0150747 A1 | 7/2006 | Mallet |
| 2006/0150748 A1 | 7/2006 | Mallet |
| 2006/0173444 A1 | 8/2006 | Choy et al. |
| 2006/0178633 A1 | 8/2006 | Garibotto et al. |
| 2006/0189895 A1 | 8/2006 | Neel et al. |
| 2006/0195064 A1 | 8/2006 | Plahey et al. |
| 2006/0202859 A1 | 9/2006 | Mastrototaro et al. |
| 2006/0206029 A1 | 9/2006 | Yair |
| 2006/0229557 A1 | 10/2006 | Fathallah et al. |
| 2006/0243804 A1 | 10/2006 | Cristoffersen et al. |
| 2006/0253086 A1 | 11/2006 | Moberg et al. |
| 2006/0253296 A1 | 11/2006 | Liisberg et al. |
| 2006/0264835 A1 | 11/2006 | Nielson et al. |
| 2006/0271022 A1 | 11/2006 | Steinbeach et al. |
| 2006/0272652 A1 | 12/2006 | Stocker et al. |
| 2006/0281980 A1 | 12/2006 | Randlov et al. |
| 2006/0282290 A1 | 12/2006 | Flaherty et al. |
| 2006/0293576 A1 | 12/2006 | Van Antwerp et al. |
| 2006/0293577 A1 | 12/2006 | Morrison et al. |
| 2007/0000337 A1 | 1/2007 | Gross |
| 2007/0003434 A1 | 1/2007 | Padmanabhan et al. |
| 2007/0016170 A1 | 1/2007 | Kovelman |
| 2007/0016449 A1 | 1/2007 | Cohen et al. |
| 2007/0033074 A1 | 2/2007 | Nitzan et al. |
| 2007/0060869 A1 | 3/2007 | Tolle et al. |
| 2007/0060870 A1 | 3/2007 | Tolle et al. |
| 2007/0066956 A1 | 3/2007 | Finkel |
| 2007/0073129 A1 | 3/2007 | Shah et al. |
| 2007/0073236 A1 | 3/2007 | Mernoe et al. |
| 2007/0088267 A1 | 4/2007 | Shekalim |
| 2007/0093786 A1 | 4/2007 | Goldsmith et al. |
| 2007/0100222 A1 | 5/2007 | Mastrototaro et al. |
| 2007/0100235 A1 | 5/2007 | Kennedy |
| 2007/0112261 A1 | 5/2007 | Enegren et al. |
| 2007/0112301 A1 | 5/2007 | Preuthun et al. |
| 2007/0118405 A1 | 5/2007 | Campbell et al. |
| 2007/0123819 A1 | 5/2007 | Mernoe et al. |
| 2007/0124002 A1 | 5/2007 | Estes et al. |
| 2007/0149926 A1 | 6/2007 | Moberg et al. |
| 2007/0150019 A1 | 6/2007 | Youker et al. |
| 2007/0142822 A1 | 7/2007 | Remde |
| 2007/0156033 A1 | 7/2007 | Causey, III et al. |
| 2007/0156092 A1 | 7/2007 | Estes et al. |
| 2007/0161955 A1 | 7/2007 | Bynum et al. |
| 2007/0167905 A1 | 7/2007 | Estes et al. |
| 2007/0167912 A1 | 7/2007 | Causey et al. |
| 2007/0173712 A1 | 7/2007 | Shah et al. |
| 2007/0173762 A1 | 7/2007 | Estes et al. |
| 2007/0179444 A1 | 8/2007 | Causey et al. |
| 2007/0201992 A1 | 8/2007 | Mernoe et al. |
| 2007/0203459 A1 | 8/2007 | Mernoe et al. |
| 2007/0219480 A1 | 9/2007 | Kamen et al. |
| 2007/0219496 A1 | 9/2007 | Kamen et al. |
| 2007/0219597 A1 | 9/2007 | Kamen et al. |
| 2007/0227907 A1 | 10/2007 | Shah et al. |
| 2007/0228071 A1 | 10/2007 | Kamen et al. |
| 2007/0250007 A1 | 10/2007 | Shekalim et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255348 A1 | 11/2007 | Holtzclaw |
| 2007/0258395 A1 | 11/2007 | Jollota et al. |
| 2007/0264130 A1 | 11/2007 | Mallett |
| 2007/0270750 A1 | 11/2007 | Dacquay |
| 2007/0287985 A1 | 12/2007 | Estes et al. |
| 2007/0288176 A1 | 12/2007 | Carlisle et al. |
| 2007/0299399 A1 | 12/2007 | Alferness et al. |
| 2008/0004601 A1 | 1/2008 | Jennewine et al. |
| 2008/0015510 A1 | 1/2008 | Sandoz et al. |
| 2008/0026473 A1 | 1/2008 | Wang et al. |
| 2008/0029173 A1 | 2/2008 | DiPerna |
| 2008/0033350 A1 | 2/2008 | Wilson et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0033402 A1 | 2/2008 | Blomquist |

(56) References Cited

U.S. PATENT DOCUMENTS

| | | |
|---|---|---|
| 2008/0033749 A1 | 2/2008 | Blomquist |
| 2008/0034323 A1 | 2/2008 | Blomquist |
| 2008/0045891 A1 | 2/2008 | Maule et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0051697 A1 | 2/2008 | Mounce et al. |
| 2008/0051698 A1 | 2/2008 | Mounce et al. |
| 2008/0051709 A1 | 2/2008 | Mounce et al. |
| 2008/0051711 A1 | 2/2008 | Mounce et al. |
| 2008/0051716 A1 | 2/2008 | Stutz |
| 2008/0051727 A1 | 2/2008 | Moberg et al. |
| 2008/0051765 A1 | 2/2008 | Mounce et al. |
| 2008/0058697 A1 | 3/2008 | Kamen et al. |
| 2008/0065007 A1 | 3/2008 | Peterson et al. |
| 2008/0065016 A1 | 3/2008 | Peterson et al. |
| 2008/0071220 A1 | 3/2008 | Rhinehart et al. |
| 2008/0071222 A1 | 3/2008 | Rhad et al. |
| 2008/0071580 A1 | 3/2008 | Marcus et al. |
| 2008/0082040 A1 | 4/2008 | Kubler et al. |
| 2008/0082363 A1 | 4/2008 | Habashi |
| 2008/0092969 A1 | 4/2008 | DiPerna |
| 2008/0097289 A1 | 4/2008 | Steil et al. |
| 2008/0097291 A1 | 4/2008 | Hanson et al. |
| 2008/0097309 A1 | 4/2008 | Enegren et al. |
| 2008/0097327 A1 | 4/2008 | Bente et al. |
| 2008/0097375 A1 | 4/2008 | Bikovsky |
| 2008/0114228 A1 | 5/2008 | McCloskey et al. |
| 2008/0116647 A1 | 5/2008 | Anderson et al. |
| 2008/0119705 A1 | 5/2008 | Patel et al. |
| 2008/0125700 A1 | 5/2008 | Moberg et al. |
| 2008/0126969 A1 | 5/2008 | Blomquist |
| 2008/0281276 A1 | 5/2008 | Shekalim et al. |
| 2008/0139910 A1 | 6/2008 | Mastrototaro et al. |
| 2008/0147004 A1 | 6/2008 | Mann et al. |
| 2008/0147050 A1 | 6/2008 | Mann et al. |
| 2008/0148235 A1 | 6/2008 | Foresti et al. |
| 2008/0156661 A1 | 7/2008 | Cooper et al. |
| 2008/0160492 A1 | 7/2008 | Campbell et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177154 A1 | 7/2008 | Hansen et al. |
| 2008/0177155 A1 | 7/2008 | Hansen et al. |
| 2008/0183060 A1 | 7/2008 | Steil et al. |
| 2008/0188723 A1 | 8/2008 | Kristensen et al. |
| 2008/0196762 A1 | 8/2008 | Mallett et al. |
| 2008/0197801 A1 | 8/2008 | Manor et al. |
| 2008/0200868 A1 | 8/2008 | Alberti et al. |
| 2008/0200869 A1 | 8/2008 | Bedingfield et al. |
| 2008/0206799 A1 | 8/2008 | Blomquist |
| 2008/0221523 A1 | 9/2008 | Moberg et al. |
| 2008/0228056 A1 | 9/2008 | Blomquist et al. |
| 2008/0234637 A1 | 9/2008 | McConnell et al. |
| 2008/0243062 A1 | 10/2008 | DeStefano et al. |
| 2008/0269584 A1 | 10/2008 | Shekalim |
| 2008/0269680 A1 | 10/2008 | Ibranyan et al. |
| 2008/0269681 A1 | 10/2008 | Kavazov et al. |
| 2008/0269682 A1 | 10/2008 | Kavazov et al. |
| 2008/0269714 A1 | 10/2008 | Mastrototaro et al. |
| 2008/0269723 A1 | 10/2008 | Mastrototaro et al. |
| 2008/0287887 A1 | 11/2008 | Mack et al. |
| 2008/0287922 A1 | 11/2008 | Panduro |
| 2008/0289718 A1 * | 11/2008 | Drew .................. A47L 7/0014 141/1 |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300534 A1 | 12/2008 | Blomquist |
| 2008/0300572 A1 | 12/2008 | Rankers et al. |
| 2008/0300651 A1 | 12/2008 | Gerber et al. |
| 2008/0304365 A1 | 12/2008 | Jarvis et al. |
| 2008/0306434 A1 | 12/2008 | Dobbles et al. |
| 2008/0306444 A1 | 12/2008 | Brister et al. |
| 2008/0317605 A1 | 12/2008 | Amley et al. |
| 2009/0014458 A1 | 1/2009 | Heffron |
| 2009/0018495 A1 | 1/2009 | Panduro |
| 2009/0018779 A1 | 1/2009 | Cohen et al. |
| 2009/0030733 A1 | 1/2009 | Cohen et al. |
| 2009/0036870 A1 | 2/2009 | Mounce et al. |
| 2009/0037020 A1 | 2/2009 | Brown |
| 2009/0043290 A1 | 2/2009 | Villegas et al. |
| 2009/0062767 A1 | 3/2009 | Van Antwerp |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069783 A1 | 3/2009 | Ellstrom et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0082728 A1 | 3/2009 | Bikovsky |
| 2009/0628878 | 3/2009 | Mass et al. |
| 2009/0085768 A1 | 4/2009 | Patel et al. |
| 2009/0088701 A1 | 4/2009 | Larsen |
| 2009/0088731 A1 | 4/2009 | Campbell et al. |
| 2009/0099866 A1 | 4/2009 | Newman |
| 2009/0099867 A1 | 4/2009 | Newman |
| 2009/0101549 A1 | 4/2009 | Kamen et al. |
| 2009/0107335 A1 | 4/2009 | Wilt et al. |
| 2009/0108016 A1 | 4/2009 | Brown et al. |
| 2009/0112626 A1 | 4/2009 | Talbot et al. |
| 2009/0113295 A1 | 4/2009 | Halpern et al. |
| 2009/0131863 A1 | 5/2009 | Carlisle et al. |
| 2009/0137987 A1 | 5/2009 | Ali |
| 2009/0143661 A1 | 6/2009 | Taub et al. |
| 2009/0143732 A1 | 6/2009 | O'Connor et al. |
| 2009/0144089 A1 | 6/2009 | Heywood et al. |
| 2009/0150186 A1 | 6/2009 | Cohen et al. |
| 2009/0150484 A1 | 6/2009 | Roberts |
| 2009/0150865 A1 | 6/2009 | Young et al. |
| 2009/0156990 A1 | 6/2009 | Wenger et al. |
| 2009/0156991 A1 | 6/2009 | Roberts |
| 2009/0157202 A1 | 6/2009 | Roberts et al. |
| 2009/0157622 A1 | 6/2009 | Roberts et al. |
| 2009/0157695 A1 | 6/2009 | Roberts |
| 2009/0158274 A1 | 6/2009 | Roberts |
| 2009/0163855 A1 | 6/2009 | Shin et al. |
| 2009/0170056 A1 | 7/2009 | Nam et al. |
| 2009/0171269 A1 | 7/2009 | Jennewine et al. |
| 2009/0171324 A1 | 7/2009 | Chong et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177248 A1 | 7/2009 | Roberts |
| 2009/0177249 A1 | 7/2009 | Roberts et al. |
| 2009/0177769 A1 | 7/2009 | Roberts |
| 2009/0177991 A1 | 7/2009 | Davis et al. |
| 2009/0191067 A1 | 7/2009 | DiPerna |
| 2009/0192366 A1 | 7/2009 | Mensinger |
| 2009/0192724 A1 | 7/2009 | Brauker et al. |
| 2009/0192745 A1 | 7/2009 | Kamath |
| 2009/0204113 A1 | 8/2009 | Mac Adam et al. |
| 2009/0212966 A1 | 8/2009 | Panduro |
| 2009/0217982 A1 | 9/2009 | DiPerna |
| 2009/0221891 A1 | 9/2009 | Yu et al. |
| 2009/0227855 A1 | 9/2009 | Hill et al. |
| 2009/0227888 A1 | 9/2009 | Salmi et al. |
| 2009/0229374 A1 | 9/2009 | Carlisle et al. |
| 2009/0234594 A1 | 9/2009 | Carlisle et al. |
| 2009/0240193 A1 | 9/2009 | Mensinger et al. |
| 2009/0246035 A1 | 10/2009 | Patzer |
| 2009/0247931 A1 | 10/2009 | Damgaard-Sorensen |
| 2009/0247982 A1 | 10/2009 | Krulevitch et al. |
| 2009/0254037 A1 | 10/2009 | Bryant, Jr. et al. |
| 2009/0256527 A1 | 10/2009 | Welsch et al. |
| 2009/0259183 A1 | 10/2009 | Chong et al. |
| 2009/0259198 A1 | 10/2009 | Chong et al. |

(56) References Cited

U.S. PATENT DOCUMENTS

| | | |
|---|---|---|
| 2009/0259209 A1 | 10/2009 | Chong et al. |
| 2009/0264825 A1 | 10/2009 | Cote et al. |
| 2009/0267774 A1 | 10/2009 | Enegren et al. |
| 2009/0267775 A1 | 10/2009 | Enegren et al. |
| 2009/0270705 A1 | 10/2009 | Enegren et al. |
| 2009/0270810 A1 | 10/2009 | DeBelser et al. |
| 2009/0270811 A1 | 10/2009 | Mounce et al. |
| 2009/0270833 A1 | 10/2009 | DeBelser et al. |
| 2009/0272928 A1 | 11/2009 | Alvarez et al. |
| 2009/0275886 A1 | 11/2009 | Blomquist et al. |
| 2009/0275887 A1 | 11/2009 | Estes et al. |
| 2009/0275896 A1 | 11/2009 | Kamen et al. |
| 2009/0281393 A1 | 11/2009 | Smith |
| 2009/0287153 A1 | 11/2009 | Bresina et al. |
| 2009/0287180 A1 | 11/2009 | DiPerna |
| 2009/0289916 A1 | 11/2009 | Dai |
| 2009/0292245 A1 | 11/2009 | Basso et al. |
| 2009/0299438 A1 | 12/2009 | Nolan et al. |
| 2009/0321675 A1 | 12/2009 | Alvarez et al. |
| 2009/0326458 A1 | 12/2009 | Chong et al. |
| 2010/0008795 A1 | 1/2010 | DiPerna |
| 2010/0010330 A1 | 1/2010 | Rankers et al. |
| 2010/0010647 A1 | 1/2010 | Schroeder et al. |
| 2010/0016791 A1 | 1/2010 | Chong et al. |
| 2010/0022937 A1 | 1/2010 | Bedingfield et al. |
| 2010/0028208 A1 | 2/2010 | Shekalim et al. |
| 2010/0030045 A1 | 2/2010 | Gottlieb et al. |
| 2010/0030092 A1 | 2/2010 | Kristensen et al. |
| 2010/0032041 A1 | 2/2010 | DiPerna |
| 2010/0036327 A1 | 2/2010 | DiPerna |
| 2010/0037680 A1 | 2/2010 | Moberg et al. |
| 2010/0038572 A1 | 2/2010 | Alvarez et al. |
| 2010/0043738 A1 | 2/2010 | Grandvallet et al. |
| 2010/0049126 A1 | 2/2010 | Bronfeld et al. |
| 2010/0049164 A1 | 2/2010 | Estes et al. |
| 2010/0050236 A1 | 2/2010 | Miller et al. |
| 2010/0063765 A1 | 3/2010 | Carlisle et al. |
| 2010/0064257 A1 | 3/2010 | Buck et al. |
| 2010/0065578 A1 | 3/2010 | Di Perna et al. |
| 2010/0065579 A1 | 3/2010 | DiPerna |
| 2010/0069890 A1 | 3/2010 | Graskov et al. |
| 2010/0071446 A1 | 3/2010 | Brown |
| 2010/0081993 A1 | 4/2010 | O'Connor |
| 2010/0087777 A1 | 4/2010 | Hopping et al. |
| 2010/0094114 A1 | 4/2010 | Robinson et al. |
| 2010/0095229 A1 | 4/2010 | Dixon et al. |
| 2010/0096019 A1 | 4/2010 | DiPerna |
| 2010/0100026 A1 | 4/2010 | Morris |
| 2010/0100037 A1 | 4/2010 | Cozmi et al. |
| 2010/0105999 A1 | 4/2010 | Dixon et al. |
| 2010/0106100 A1 | 4/2010 | Petersen |
| 2010/0114015 A1 | 5/2010 | Kanderian, Jr. et al. |
| 2010/0114027 A1 | 5/2010 | Jacobson et al. |
| 2010/0119414 A1 | 5/2010 | Eisenhardt et al. |
| 2010/0121169 A1 | 5/2010 | Petisce et al. |
| 2010/0121306 A1 | 5/2010 | Yodfat et al. |
| 2010/0121415 A1 | 5/2010 | Skelton |
| 2010/0130933 A1 | 5/2010 | Holland et al. |
| 2010/0134305 A1 | 6/2010 | Lu et al. |
| 2010/0137833 A1 | 6/2010 | Glynn |
| 2010/0138197 A1 | 6/2010 | Sher |
| 2010/0145262 A1 | 6/2010 | Bengtsson et al. |
| 2010/0145303 A1 | 6/2010 | Yodfat et al. |
| 2010/0152658 A1 | 6/2010 | Hanson et al. |
| 2010/0152674 A1 | 6/2010 | Kavazov et al. |
| 2010/0160740 A1 | 6/2010 | Cohen et al. |
| 2010/0161236 A1 | 6/2010 | Cohen et al. |
| 2010/0161346 A1 | 6/2010 | Getschmann et al. |
| 2010/0162786 A1 | 7/2010 | Keenan et al. |
| 2010/0164727 A1 | 7/2010 | Bazargan et al. |
| 2010/0165795 A1 | 7/2010 | Elder et al. |
| 2010/0168538 A1 | 7/2010 | Keenan et al. |
| 2010/0168539 A1 | 7/2010 | Palerm et al. |
| 2010/0168543 A1 | 7/2010 | Kamath et al. |
| 2010/0168670 A1 | 7/2010 | Srisathapat et al. |
| 2010/0168711 A1 | 7/2010 | Bazargan et al. |
| 2010/0174230 A1 | 7/2010 | Istoc et al. |
| 2010/0174266 A1 | 7/2010 | Estes |
| 2010/0174553 A1 | 7/2010 | Kaufman et al. |
| 2010/0179402 A1 | 7/2010 | Goode, Jr. et al. |
| 2010/0185142 A1 | 7/2010 | Kamen et al. |
| 2010/0185175 A1 | 7/2010 | Kamen et al. |
| 2010/0191084 A1 | 7/2010 | Shah et al. |
| 2010/0191165 A1 | 7/2010 | Appling et al. |
| 2010/0192686 A1 | 8/2010 | Kamen et al. |
| 2010/0198034 A1 | 8/2010 | Thomas et al. |
| 2010/0198107 A1 | 8/2010 | Groll et al. |
| 2010/0198142 A1 | 8/2010 | Sloan et al. |
| 2010/0198143 A1 | 8/2010 | Estes et al. |
| 2010/0198183 A1 | 8/2010 | Lanigan et al. |
| 2010/0198520 A1 | 8/2010 | Breton et al. |
| 2010/0205001 A1 | 8/2010 | Knudsen et al. |
| 2010/0217192 A1 | 8/2010 | Moberg et al. |
| 2010/0217193 A1 | 8/2010 | Moberg et al. |
| 2010/0218132 A1 | 8/2010 | Soni et al. |
| 2010/0218586 A1 | 9/2010 | Rosinko |
| 2010/0222735 A1 | 9/2010 | Plahey et al. |
| 2010/0222765 A1 | 9/2010 | Blomquist et al. |
| 2010/0224192 A1 | 9/2010 | Dixon et al. |
| 2010/0228186 A1 | 9/2010 | Estes et al. |
| 2010/0234708 A1 | 9/2010 | Buck et al. |
| 2010/0234709 A1 | 9/2010 | Say et al. |
| 2010/0235439 A1 | 9/2010 | Goodnow |
| 2010/0241065 A1 | 9/2010 | Moberg et al. |
| 2010/0249530 A1 | 9/2010 | Rankers et al. |
| 2010/0249566 A1 | 9/2010 | Suess et al. |
| 2010/0249706 A1 | 9/2010 | Clemente |
| 2010/0250697 A1 | 9/2010 | Hansen et al. |
| 2010/0251114 A1 | 9/2010 | Wehba et al. |
| 2010/0094251 A1 | 10/2010 | Estes et al. |
| 2010/0253768 A1 | 10/2010 | Ek-Maraghi et al. |
| 2010/0256466 A1 | 10/2010 | Shekalim et al. |
| 2010/0256561 A1 | 10/2010 | Gillespie, Jr. et al. |
| 2010/0256565 A1 | 10/2010 | Mernoe et al. |
| 2010/0256598 A1 | 10/2010 | Mernoe et al. |
| 2010/0261987 A1 | 10/2010 | Kamath |
| 2010/0262078 A1 | 10/2010 | Blomquist |
| 2010/0262434 A1 | 10/2010 | Shaya |
| 2010/0274192 A1 | 10/2010 | Mernoe |
| 2010/0274592 A1 | 10/2010 | Nitzan et al. |
| 2010/0277119 A1 | 11/2010 | Montague et al. |
| 2010/0280329 A1 | 11/2010 | Randlov et al. |
| 2010/0280442 A1 | 11/2010 | Shahmirian et al. |
| 2010/0280486 A1 | 11/2010 | Khair et al. |
| 2010/0286563 A1 | 11/2010 | Bryer et al. |
| 2010/0292556 A1 | 11/2010 | Golden |
| 2010/0298662 A1 | 11/2010 | Yu et al. |
| 2010/0298681 A1 | 11/2010 | Say |
| 2010/0299156 A1 | 11/2010 | Jorgensen |
| 2010/0305421 A1 | 12/2010 | Ow-Wing |
| 2010/0305545 A1 | 12/2010 | Kanderian, Jr. et al. |
| 2010/0312082 A1 | 12/2010 | Batman et al. |
| 2010/0317950 A1 | 12/2010 | Galley et al. |
| 2010/0317951 A1 | 12/2010 | Rutkowski et al. |
| 2010/0323431 A1 | 12/2010 | Rutkowski et al. |
| 2010/0324382 A1 | 12/2010 | Cantwell et al. |
| 2010/0324394 A1 | 12/2010 | Say et al. |
| 2010/0324853 A1 | 12/2010 | Want et al. |
| 2010/0324932 A1 | 12/2010 | Galley et al. |
| 2010/0331651 A1 | 12/2010 | Groll |
| 2010/0331652 A1 | 12/2010 | Groll et al. |
| 2010/0331824 A1 | 12/2010 | Moberg et al. |
| 2011/0004188 A1 | 1/2011 | Shekalim |
| 2011/0006876 A1 | 1/2011 | Moberg et al. |
| 2011/0009725 A1 | 1/2011 | Hill et al. |
| 2011/0009798 A1 | 1/2011 | Kelly et al. |
| 2011/0009813 A1 | 1/2011 | Rankers |
| 2011/0009823 A1 | 1/2011 | Chong et al. |
| 2011/0009825 A1 | 1/2011 | Chong et al. |
| 2011/0009846 A1 | 1/2011 | Istoc et al. |
| 2011/0010105 A1 | 1/2011 | Shah et al. |
| 2011/0015509 A1 | 1/2011 | Peyser |
| 2011/0021898 A1 | 1/2011 | Wei et al. |
| 2011/0022025 A1 | 1/2011 | Sovoie et al. |

(56) References Cited

U.S. PATENT DOCUMENTS

| | | |
|---|---|---|
| 2011/0028937 A1 | 2/2011 | Powers et al. |
| 2011/0030845 A1 | 2/2011 | Chong et al. |
| 2011/0033833 A1 | 2/2011 | Blomquist |
| 2011/0034786 A1 | 2/2011 | Cadio et al. |
| 2011/0040247 A1 | 2/2011 | Mandro et al. |
| 2011/0040251 A1 | 2/2011 | Blomquist et al. |
| 2011/0044333 A1 | 2/2011 | Sicurello et al. |
| 2011/0046051 A1 | 2/2011 | Moerman |
| 2011/0046454 A1 | 2/2011 | Ejlersen et al. |
| 2011/0046469 A1 | 2/2011 | Nelson et al. |
| 2011/0046697 A1 | 2/2011 | Gerber et al. |
| 2011/0046892 A1 | 2/2011 | Moerman |
| 2011/0047499 A1 | 2/2011 | Mandro et al. |
| 2011/0048938 A1 | 3/2011 | Shah et al. |
| 2011/0048941 A1 | 3/2011 | Shah et al. |
| 2011/0050428 A1 | 3/2011 | Istoc |
| 2011/0053121 A1 | 3/2011 | Heaton |
| 2011/0054281 A1 | 3/2011 | Shah et al. |
| 2011/0054390 A1 | 3/2011 | Searle et al. |
| 2011/0054391 A1 | 3/2011 | Ward et al. |
| 2011/0054397 A1 | 3/2011 | Menot et al. |
| 2011/0058485 A1 | 3/2011 | Sloan |
| 2011/0060280 A1 | 3/2011 | Caffey et al. |
| 2011/0060281 A1 | 3/2011 | Aeschlimann et al. |
| 2011/0060328 A1 | 3/2011 | Skwarek et al. |
| 2011/0066108 A1 | 3/2011 | Geipel et al. |
| 2011/0066555 A1 | 3/2011 | Dicks et al. |
| 2011/0071372 A1 | 3/2011 | Sloan et al. |
| 2011/0071464 A1 | 3/2011 | Palerm |
| 2011/0071465 A1 | 3/2011 | Wang et al. |
| 2011/0071765 A1 | 3/2011 | Yodfat et al. |
| 2011/0077481 A1 | 3/2011 | Say et al. |
| 2011/0077493 A1 | 3/2011 | Shadforth et al. |
| 2011/0077554 A1 | 3/2011 | Roe et al. |
| 2011/0077963 A1 | 3/2011 | Knudsen et al. |
| 2011/0078441 A1 | 3/2011 | Dicks et al. |
| 2011/0082439 A1 | 4/2011 | Wenger et al. |
| 2011/0087195 A1 | 4/2011 | Uhland et al. |
| 2011/0092788 A1 | 4/2011 | Long et al. |
| 2011/0092894 A1 | 4/2011 | McGill et al. |
| 2011/0092907 A1 | 4/2011 | Krogh et al. |
| 2011/0092921 A1 | 4/2011 | Beling et al. |
| 2011/0093285 A1 | 4/2011 | Dicks et al. |
| 2011/0093286 A1 | 4/2011 | Dicks et al. |
| 2011/0097480 A1 | 4/2011 | Shah et al. |
| 2011/0098548 A1 | 4/2011 | Budiman |
| 2011/0098637 A1 | 4/2011 | Hill |
| 2011/0098638 A1 | 4/2011 | Chawala et al. |
| 2011/0098674 A1 | 4/2011 | Vincent et al. |
| 2011/0098676 A1 | 4/2011 | Chiang et al. |
| 2011/0101995 A1 | 5/2011 | Shah et al. |
| 2011/0105873 A1 | 5/2011 | Feldman et al. |
| 2011/0105877 A1 | 5/2011 | Wilt et al. |
| 2011/0105955 A1 | 5/2011 | Yudovsky et al. |
| 2011/0105979 A1 | 5/2011 | Schlaeper et al. |
| 2011/0106011 A1 | 5/2011 | Cinar et al. |
| 2011/0106049 A1 | 5/2011 | Damiano et al. |
| 2011/0106050 A1 | 5/2011 | Yodfat et al. |
| 2011/0106318 A1 | 5/2011 | Ledford |
| 2011/0106480 A1 | 5/2011 | Shah et al. |
| 2011/0107853 A1 | 5/2011 | Studer |
| 2011/0108158 A1 | 5/2011 | Huwiler et al. |
| 2011/0111794 A1 | 5/2011 | Bochenko |
| 2011/0112478 A1 | 5/2011 | Gregor et al. |
| 2011/0112504 A1 | 5/2011 | Causey et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118662 A1 | 5/2011 | Mhatre et al. |
| 2011/0118699 A1 | 5/2011 | Yodafat et al. |
| 2011/0118700 A1 | 5/2011 | Remde |
| 2011/0119087 A1 | 5/2011 | Drucker et al. |
| 2011/0120206 A1 | 5/2011 | Troughton et al. |
| 2011/0124996 A1 | 5/2011 | Reinke et al. |
| 2011/0124999 A1 | 5/2011 | Reggiardo et al. |
| 2011/0125085 A1 | 5/2011 | McGill et al. |
| 2011/0125095 A1 | 5/2011 | Lebel et al. |
| 2011/0125530 A1 | 5/2011 | Drucker et al. |
| 2011/0126188 A1 | 5/2011 | Bernstein et al. |
| 2011/0130746 A1 | 6/2011 | Budiman |
| 2011/0133946 A1 | 6/2011 | Kopp et al. |
| 2011/0137239 A1 | 6/2011 | DeBelser et al. |
| 2011/0144569 A1 | 6/2011 | Britton et al. |
| 2011/0144586 A1 | 6/2011 | Michaud et al. |
| 2011/0144616 A1 | 6/2011 | Michaud et al. |
| 2011/0149759 A1 | 6/2011 | Jollota |
| 2011/0151571 A1 | 6/2011 | Wooldridge |
| 2011/0152653 A1 | 6/2011 | Shekalim et al. |
| 2011/0152654 A1 | 6/2011 | Wang et al. |
| 2011/0152757 A1 | 6/2011 | Beck et al. |
| 2011/0152769 A1 | 6/2011 | Ramey et al. |
| 2011/0152770 A1 | 6/2011 | DiPerna et al. |
| 2011/0152824 A1 | 6/2011 | DiPerna et al. |
| 2011/0152970 A1 | 6/2011 | Jollota et al. |
| 2011/0154237 A1 | 6/2011 | Bush et al. |
| 2011/0160650 A1 | 6/2011 | Chong et al. |
| 2011/0160654 A1 | 6/2011 | Hanson et al. |
| 2011/0160666 A1 | 6/2011 | Hanson et al. |
| 2011/0160667 A1 | 6/2011 | Bazargan et al. |
| 2011/0160678 A1 | 6/2011 | Chong et al. |
| 2011/0160695 A1 | 6/2011 | Sigrist et al. |
| 2011/0163125 A1 | 7/2011 | Beavis et al. |
| 2011/0166544 A1 | 7/2011 | Verhoef et al. |
| 2011/0166875 A1 | 7/2011 | Hayter et al. |
| 2011/0172744 A1 | 7/2011 | Davis et al. |
| 2011/0178461 A1 | 7/2011 | Chong et al. |
| 2011/0178462 A1 | 7/2011 | Moberg et al. |
| 2011/0184264 A1 | 7/2011 | Galasso et al. |
| 2011/0190614 A1 | 8/2011 | Brister et al. |
| 2011/0190694 A1 | 8/2011 | Lanier, Jr. et al. |
| 2011/0190700 A1 | 8/2011 | Kavazov et al. |
| 2011/0190701 A1 | 8/2011 | Remde et al. |
| 2011/0192478 A1 | 8/2011 | Chong et al. |
| 2011/0196213 A1 | 8/2011 | Thukral et al. |
| 2011/0196248 A1 | 8/2011 | Grunwald |
| 2011/0196289 A1 | 8/2011 | Plahey et al. |
| 2011/0205065 A1 | 8/2011 | Strachan et al. |
| 2011/0208122 A1 | 8/2011 | Shekalim |
| 2011/0208123 A1 | 8/2011 | Gray et al. |
| 2011/0208155 A1 | 8/2011 | Palerm et al. |
| 2011/0213225 A1 | 9/2011 | Bernstein et al. |
| 2011/0213306 A1 | 9/2011 | Hanson et al. |
| 2011/0224522 A1 | 9/2011 | Fennell |
| 2011/0224601 A1 | 9/2011 | Shekalim |
| 2011/0230821 A1 | 9/2011 | Babic |
| 2011/0230825 A1 | 9/2011 | Kamen et al. |
| 2011/0247397 A1 | 10/2011 | Friedli et al. |
| 2011/0251557 A1 | 10/2011 | Powers |
| 2011/0251579 A1 | 10/2011 | Aklog et al. |
| 2011/0256024 A1 | 10/2011 | Cole et al. |
| 2011/0257895 A1 | 10/2011 | Brauker et al. |
| 2011/0309017 A1 | 12/2011 | Shekalim et al. |
| 2011/0309107 A1 | 12/2011 | Shekalim et al. |
| 2011/0319862 A1 | 12/2011 | Friedman et al. |
| 2012/0013625 A1 | 1/2012 | Blomquist |
| 2012/0013802 A1 | 1/2012 | Blomquist |
| 2012/0017688 A1 | 1/2012 | Shekalim |
| 2012/0022452 A1 | 1/2012 | Welsch et al. |
| 2012/0029433 A1 | 2/2012 | Michaud et al. |
| 2012/0029468 A1 | 2/2012 | DiPerna et al. |
| 2012/0029486 A1 | 2/2012 | DiPerna |
| 2012/0029708 A1 | 2/2012 | Miller et al. |
| 2012/0030610 A1 | 2/2012 | DiPerna et al. |
| 2012/0041384 A1 | 2/2012 | Finke et al. |
| 2012/0059673 A1 | 3/2012 | Cohen et al. |
| 2012/0232520 A1 | 9/2012 | Sloan et al. |
| 2013/0012877 A1 | 1/2013 | Debelser et al. |
| 2013/0012917 A1 | 1/2013 | Miller et al. |
| 2013/0053816 A1 | 2/2013 | DiPerna et al. |
| 2013/0150766 A1 | 6/2013 | Olde et al. |
| 2013/0204542 A1 | 8/2013 | Olde et al. |
| 2013/0237947 A1 | 9/2013 | Amirouche et al. |
| 2013/0283196 A1 | 10/2013 | Farnan et al. |
| 2013/0296788 A1 | 11/2013 | Ogihara |

(56) References Cited

U.S. PATENT DOCUMENTS

| | | |
|---|---|---|
| 2013/0298024 A1 | 11/2013 | Rhee et al. |
| 2013/0306191 A1 | 11/2013 | Metzmaker et al. |
| 2013/0324928 A1 | 12/2013 | Kruse |
| 2013/0332874 A1 | 12/2013 | Rosinko et al. |
| 2014/0039392 A1 | 2/2014 | Geipel et al. |
| 2014/0039805 A1 | 2/2014 | Sharpe, Jr. et al. |
| 2014/0054883 A1 | 2/2014 | Lanigan et al. |
| 2014/0094764 A1 | 4/2014 | Blomquist et al. |
| 2014/0276409 A1 | 9/2014 | Rosinko et al. |
| 2014/0276537 A1 | 9/2014 | Kruse |
| 2014/0276538 A1 | 9/2014 | Michaud |
| 2015/0122052 A1 | 5/2015 | Rosinko et al. |
| 2015/0174320 A1 | 6/2015 | Grant et al. |
| 2016/0051758 A1 | 2/2016 | Rosinko et al. |
| 2016/0058668 A1 | 3/2016 | Metzmaker et al. |
| 2016/0082186 A1 | 3/2016 | Rosinko et al. |
| 2017/0035962 A1 | 2/2017 | Lecanu-Fayet et al. |

FOREIGN PATENT DOCUMENTS

| | | |
|---|---|---|
| CN | 2668847 Y | 1/2005 |
| DE | 399065 | 7/1924 |
| DE | 19819407 | 11/1999 |
| EP | 0055836 | 7/1982 |
| EP | 0272530 | 6/1988 |
| EP | 0376894 | 12/1988 |
| EP | 0385916 | 5/1990 |
| EP | 0494042 | 7/1992 |
| EP | 0560571 | 9/1993 |
| EP | 560571 B1 | 5/1997 |
| EP | 1217275 B1 | 9/2004 |
| EP | 1938750 | 7/2008 |
| GB | 2159496 A | 12/1985 |
| JP | 06-016165 | 4/1994 |
| JP | 08-312820 | 11/1996 |
| JP | 2002-143293 | 5/2002 |
| JP | 2006-009944 | 1/2006 |
| JP | 2006-101985 | 4/2009 |
| JP | 2009-148591 | 7/2009 |
| JP | 2010-075736 | 4/2010 |
| KR | 10-2001-0080519 | 8/2001 |
| WO | WO 90/013795 | 11/1990 |
| WO | WO 91/000753 | 1/1991 |
| WO | WO 94/026329 | 11/1994 |
| WO | WO 95/032013 | 11/1995 |
| WO | WO9532013 A1 | 11/1995 |
| WO | WO 96/008049 | 3/1996 |
| WO | WO9608040 | 3/1996 |
| WO | WO9613288 | 5/1996 |
| WO | WO 96/025189 | 8/1996 |
| WO | WO 98/019627 | 5/1998 |
| WO | WO 98/057683 | 12/1998 |
| WO | WO 99/001088 | 1/1999 |
| WO | WO9964103 | 12/1999 |
| WO | WO 00/010628 | 3/2000 |
| WO | WO 00/035527 | 6/2000 |
| WO | WO 00/040346 | 7/2000 |
| WO | WO 0040346 A1 | 7/2000 |
| WO | WO 00/072900 | 12/2000 |
| WO | WO 01/030422 | 5/2001 |
| WO | WO 02/011049 | 2/2002 |
| WO | WO 02/011791 | 2/2002 |
| WO | WO 02/026102 | 4/2002 |
| WO | WO 03/081052 | 3/2003 |
| WO | WO 0228532 A9 | 5/2003 |
| WO | WO 03/102737 | 6/2003 |
| WO | WO03082091 | 10/2003 |
| WO | WO 04/009152 | 1/2004 |
| WO | WO2004009160 | 1/2004 |
| WO | WO 04/088148 | 3/2004 |
| WO | WO 04/036150 | 4/2004 |
| WO | WO 04/047677 | 6/2004 |
| WO | WO 04/060464 | 7/2004 |
| WO | WO 09/098648 | 8/2004 |
| WO | WO 04/056412 | 12/2004 |
| WO | WO 04/105827 | 12/2004 |
| WO | WO 05/082450 | 2/2005 |
| WO | WO 05/018507 | 3/2005 |
| WO | WO 06/001024 | 1/2006 |
| WO | WO 08/028509 | 9/2006 |
| WO | WO 08/037270 | 9/2006 |
| WO | WO 08/037271 | 9/2006 |
| WO | WO 08/037272 | 9/2006 |
| WO | WO 08/037273 | 9/2006 |
| WO | WO 06/108219 | 10/2006 |
| WO | WO 08/043381 | 10/2006 |
| WO | WO2006127841 | 11/2006 |
| WO | WO 07/038059 | 4/2007 |
| WO | WO 07/038060 | 4/2007 |
| WO | WO 07/038091 | 4/2007 |
| WO | WO2007047279 | 4/2007 |
| WO | WO 07/056504 | 5/2007 |
| WO | WO 07/056592 | 5/2007 |
| WO | WO 2007065944 A1 | 6/2007 |
| WO | WO 07/089983 | 8/2007 |
| WO | WO 07/098265 | 8/2007 |
| WO | WO 07/098287 | 8/2007 |
| WO | WO 07/106232 | 9/2007 |
| WO | WO 07/119149 | 10/2007 |
| WO | WO 08/050126 | 10/2007 |
| WO | WO 08/050128 | 10/2007 |
| WO | WO2008024812 | 2/2008 |
| WO | WO 08/056363 | 5/2008 |
| WO | WO 08/144693 | 5/2008 |
| WO | WO 08/144695 | 5/2008 |
| WO | WO 08/144697 | 5/2008 |
| WO | WO 08/144698 | 5/2008 |
| WO | WO 09/032402 | 7/2008 |
| WO | WO 09/035759 | 7/2008 |
| WO | WO 09/035761 | 7/2008 |
| WO | WO 09/035762 | 7/2008 |
| WO | WO 08/103175 | 8/2008 |
| WO | WO 08/121599 | 10/2008 |
| WO | WO 09/032399 | 10/2008 |
| WO | WO 09/032400 | 10/2008 |
| WO | WO 09/035753 | 10/2008 |
| WO | WO 09/106233 | 2/2009 |
| WO | WO2009016636 | 2/2009 |
| WO | WO2009044221 | 4/2009 |
| WO | WO 09/094590 | 7/2009 |
| WO | WO 09/108639 | 9/2009 |
| WO | WO 09/124133 | 10/2009 |
| WO | WO 2009/143188 A2 | 11/2009 |
| WO | WO 09/147680 | 12/2009 |
| WO | WO 10/016977 | 2/2010 |
| WO | WO 10/016978 | 2/2010 |
| WO | WO 10/097774 | 2/2010 |
| WO | WO 10/033634 | 3/2010 |
| WO | WO 10/033878 | 3/2010 |
| WO | WO 10/038031 | 4/2010 |
| WO | WO 10/096449 | 8/2010 |
| WO | WO 10/099490 | 9/2010 |
| WO | WO 10/113162 | 10/2010 |
| WO | WO2011001267 | 1/2011 |
| WO | WO 11/014704 | 2/2011 |
| WO | WO 11/017667 | 2/2011 |
| WO | WO2011014704 | 2/2011 |
| WO | WO 2011/131777 A1 | 10/2011 |
| WO | WO2012019726 | 2/2012 |
| WO | WO2013173157 | 11/2013 |

OTHER PUBLICATIONS

U.S. Appl. No. 60/789,243, filed Apr. 5, 2006, Beavis.
International Search Report dated Sep. 10, 2004 in International Application: PCT/US2003/022703 filed on Jul. 15, 2003 and published as: WO 04/009152 on Jan. 29, 2004.
International Search Report and Written Opinion dated Jul. 23, 2007 in International Application: PCT/2007/060633 filed on: Jan. 17 2007 and published as: WO 07/089983 on: Aug. 9, 2007.
International Preliminary Report on Patentability dated Jul. 29, 2008 in International Application: PCT/2007/060633 filed on: Jan. 17 2007 and published as: WO 07/089983 on: Aug. 9, 2007.

(56) References Cited

OTHER PUBLICATIONS

International Search Report and Written Opinion dated May 29, 2009 in International Application: PCT/US2009/035022 filed on: Jan. 23, 2009 and published as: WO 09/108639 on: Sep. 3, 2009.
Written Opinion of the International Searching Authority dated Aug. 11, 2008 in International Application: PCT/US2008/058044 filed on: Mar. 24, 2008 and published as: WO 08/121599 on: Oct. 9, 2009.
International Search Report and Written Opinion dated Jan. 27, 2010 in International Application: PCT/US2009/049110 filed on: Jun. 29, 2009 and published as: WO 10/016977 on: Feb. 11, 2010.
International Search Report and Written Opinion dated Feb. 17, 2011 in International Application: PCT/2009/049116 filed on: Jun. 29, 2009 and published as: WO 10/016978 on: Feb. 11, 2010.
International Search Report and Written Opinion dated Feb. 4, 2010 in International Application: PCT/2009/049116 filed on: Jun. 29, 2009 and published as: WO 10/016978 on: Feb. 11, 2010.
International Preliminary Report on Patentability dated Aug. 5, 2010 in International Application: PCT/US2009/031906 filed on Jan. 23, 2009 and published as: WO 09/094590 on Jul. 30, 2009.
International Search Report and Written Opinion dated Jul. 28, 2009 in International Application: PCT/US2009/031906 filed on Jan. 23, 2009 and published as: WO 09/094590 on Jul. 30, 2009.
International Search Report and Written Opinion dated Jan. 4, 2010 in International Application: PCT/US2009/044569 filed on: May 19, 2009 and published as: WO 09/143188 on: Nov. 26, 2009.
International Search Report and Written Opinion dated Apr. 1, 2010 in International Application: PCT/2009/057208 filed on: Sep. 16, 2009 and published as: WO 10/033634 on: Mar. 25, 2010.
International Search Report and Written Opinion dated Sep. 30, 2010 in International Application: PCT/2010/025663 filed on: Feb. 26, 2010 and published as: WO 10/099490 on: Sep. 2, 2010.
International Preliminary Report on Patentability dated Mar. 31, 2011 in International Application: PCT/2009/57591 filed on: Sep. 18, 2009 and published as: WO 10/033878 on: Mar. 25, 2010.
International Search Report and Written Opinion dated Apr. 12, 2010 in International Application: PCT/2009/57591 filed on: Sep. 18, 2009 and published as: WO 10/033878 on: Mar. 25, 2010.
International Search Report and Written Opinion dated Apr. 11, 2011 in International Application: PCT/2010/034789 filed on: Jul. 29, 2010 and published as: WO 11/014704 on: Feb. 3, 2011.
Arrow International Europe Web Page for: Multiple Lumen Peripheral Catheter, Product No. IV-01150, printed from the internet on Nov. 15, 2011.
AngioDynamics, Smart Port, Power-Injectable Ports Product Brochure, Copyright 2010 AngioDynamics,Inc.
I-port ADVANCE product brochure, distributed by: Patton Medical Devices and Manufactured by Unomedical, a Cardiovascular Company, Copyright, 2007-2010 Patton Medical Devices, LP.

Miller, John E., "The Reciprocating Pump, Theory, Design and Use," Chapter 1, "Pump Types", Krieger Publishing Company, Malabar, Florida 1995.
Spring Zone Insulin Delivery System Product Brochure, Copyright 2011 Spring (formerly NiliMEDIX), a D-Medical company.
Extended European Search Report dated Mar. 6, 2012 in European Application No. EP 09751416 based on International Application No. PCT/US2009/044569.
European Search Report dated Mar. 3, 2016 (dated Feb. 23, 2016) for European Application No. 13800986.5.
European Search Report for European Application No. EP15168432 dated Sep. 1, 2015.
International Search Report and Written Opinion for International Application No. PCT/US2014/021171 dated Jun. 8, 2014.
Canadian Examiner's Report for Canadian Application No. 2,769,030 dated Aug. 27, 2014.
International Search Report and Written Opinion for International Application No. PCT/US2013/044259 dated Sep. 6, 2013.
European Search Report for European Application No. EP09751416.0-2319 dated Nov. 21, 2012.
Examination Report No. 1 for Australian Patent Application No. 2009249132 dated Jan. 23, 2014.
European Search Report for European Application No. 14152623.6-1506 dated Mar. 11, 2014.
European Search Report for European Application No. EP09704892 dated Jan. 28, 2013.
International Search Report and Written Opinion for International Application No. PCT/US2009/09116 dated Feb. 4, 2010.
International Search Report and Written Opinion for International Application No. PCT/US2010/043789 dated Apr. 11, 2011.
PCT Search Report and Written Opinion dated Jun. 9, 2014 for PCT Application No. PCT/US2014/018861 filed Feb. 27, 2014, 10 pages.
Search Report and Written Opinion dated Aug. 22, 2013 for PCT Application No. PCT/US2013/040269 filed May 9, 2013, 17 pages.
International Preliminary Report on Patentability dated Oct. 29, 2014 for PCT Application No. PCT/US2013/040269 filed May 9, 2013, 9 pages.
Application and File History for U.S. Patent Application No. PCT/US13/40269 filed May 9, 2013, inventors Metzmaker et al.
Application and File History for U.S. Appl. No. 13/474,032, filed May 17, 2012, inventors Metzmaker et al.
Search Report and Written Opinion dated Mar. 4, 2013 for PCT Application No. PCT/US2012/048020 filed Jul. 24, 2012, 10 pages.
International Preliminary Report on Patentability dated Jan. 28, 2014 for PCT Application No. PCT/US2012/048020 filed Jul. 24, 2012, 7 pages.
Application and File History for U.S. Appl. No. 14/936,979, filed Nov. 10, 2015, inventors Metzmaker et al.
Application and File History for U.S. Appl. No. 13/557,163, filed Jul. 24, 2012, inventors DePerna et al.
Application and File History for U.S. Appl. No. 15/294,845, filed Oct. 17, 2016, inventors Lecanu-Fayet et al.

\* cited by examiner

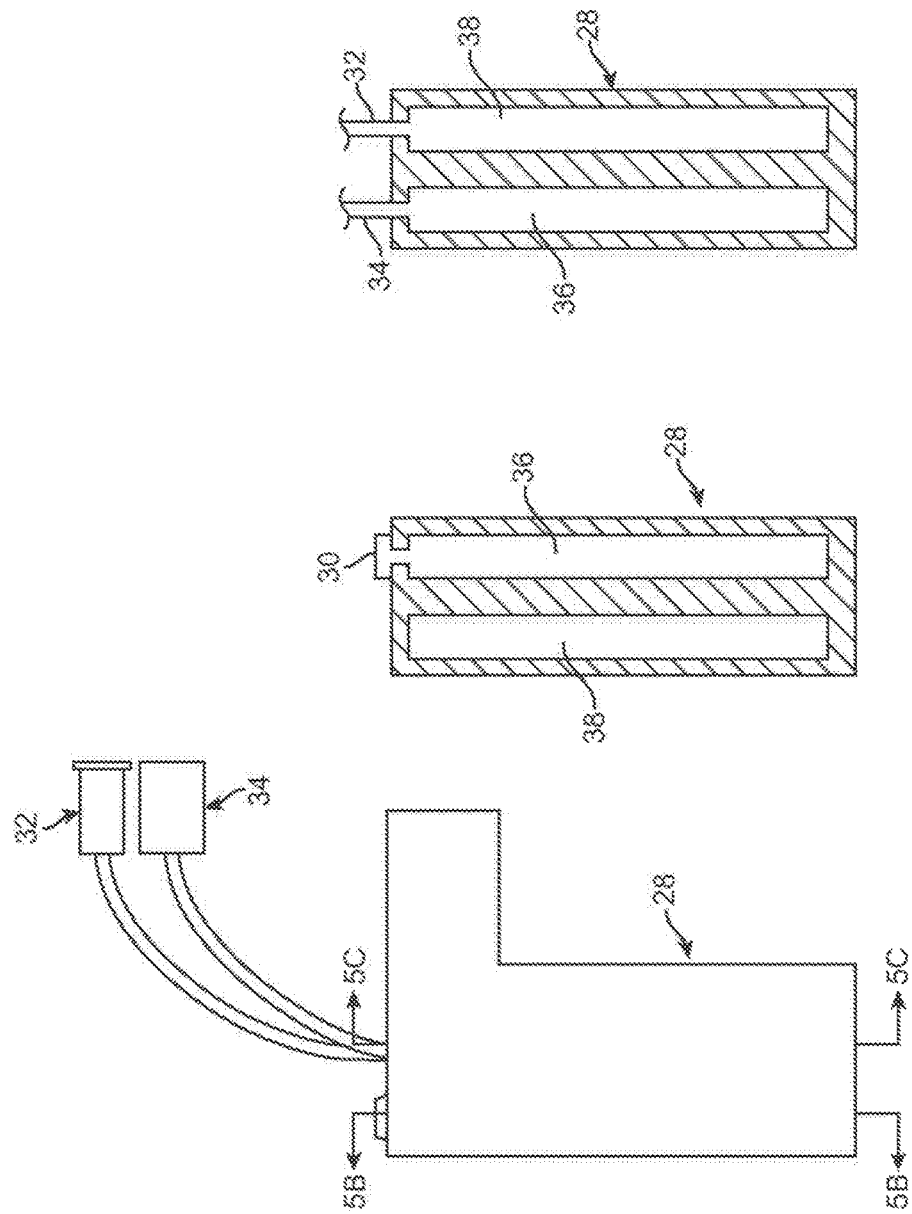

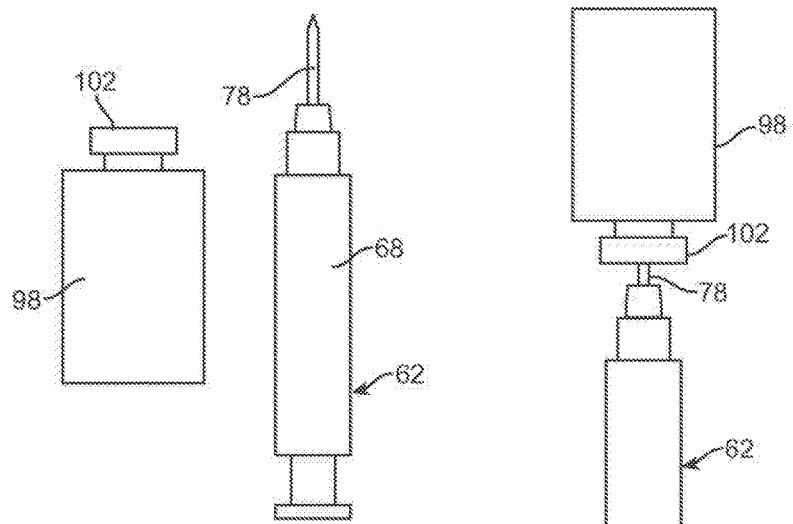
FIG. 6E
FIG. 6F
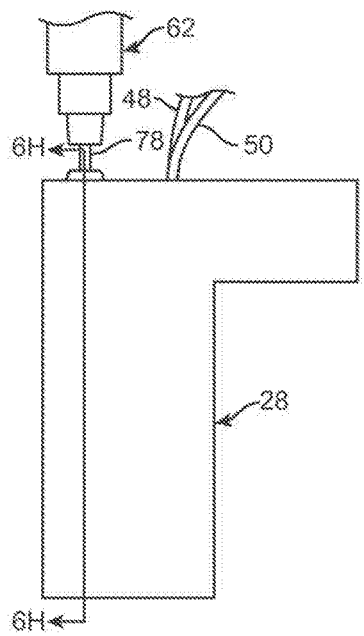
FIG. 6G
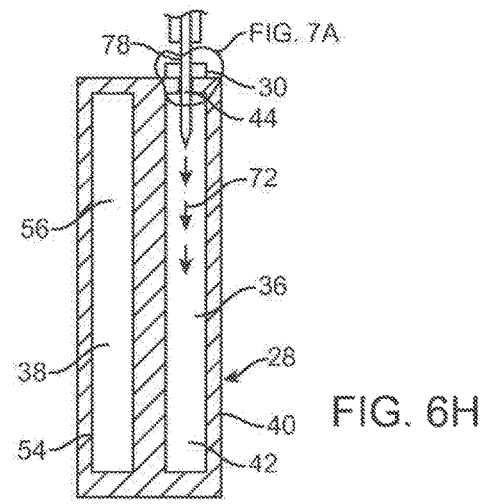
FIG. 6H

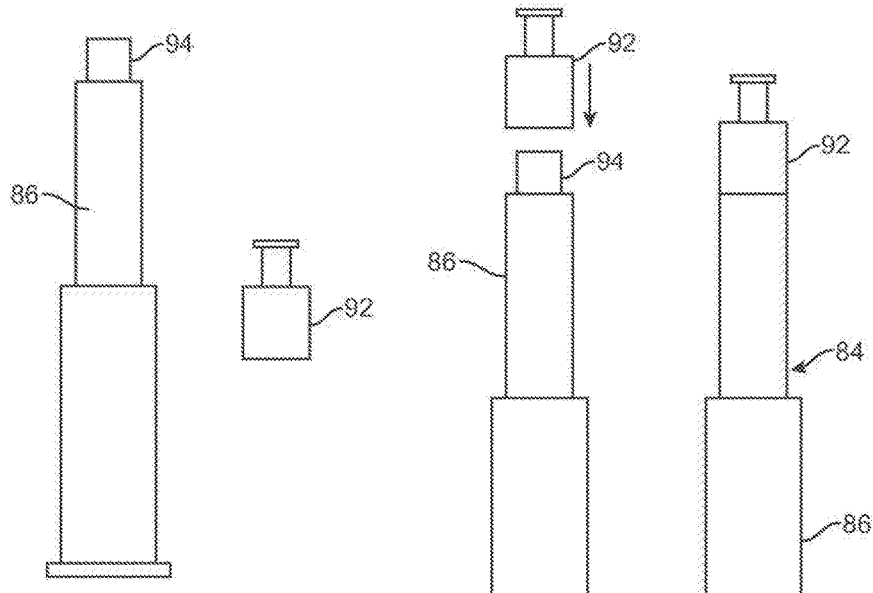
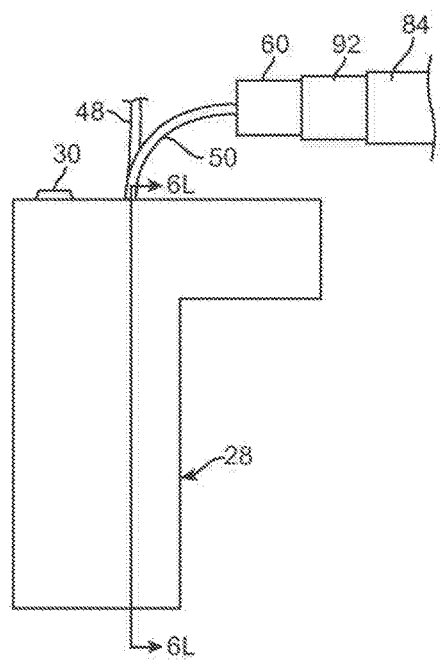
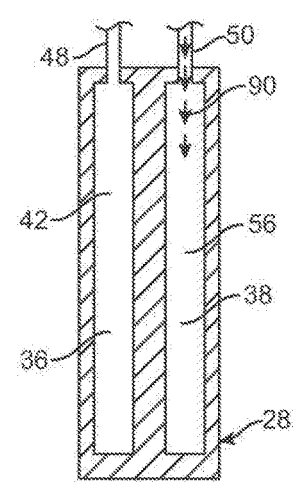
FIG. 6I
FIG. 6J
FIG. 6K
FIG. 6L

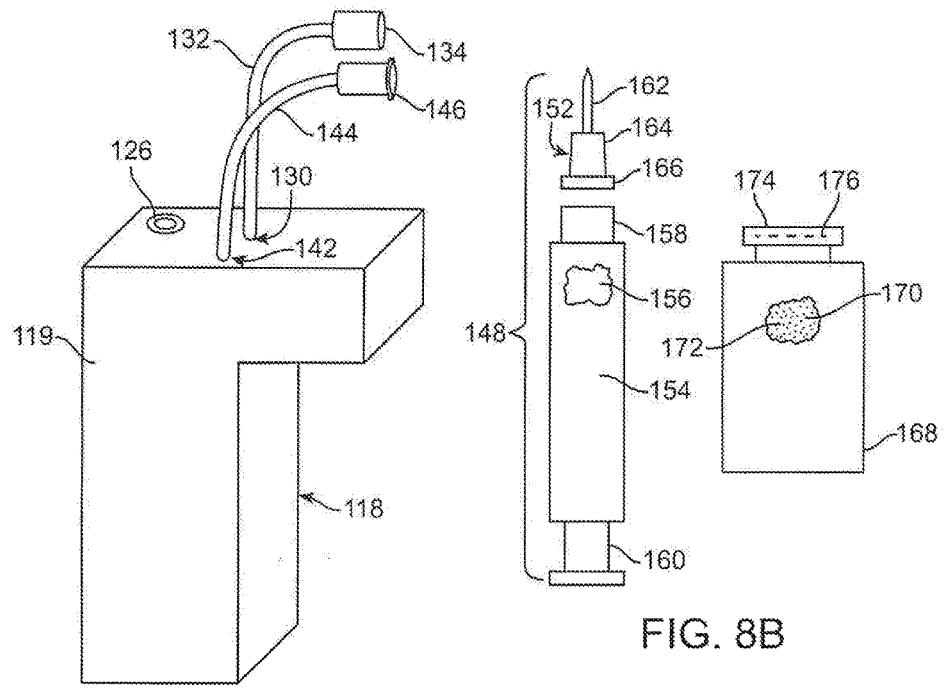
FIG. 8A
FIG. 8B
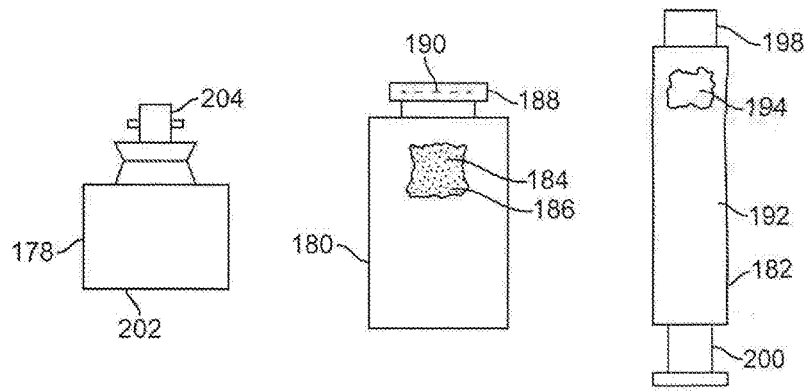
FIG. 8C

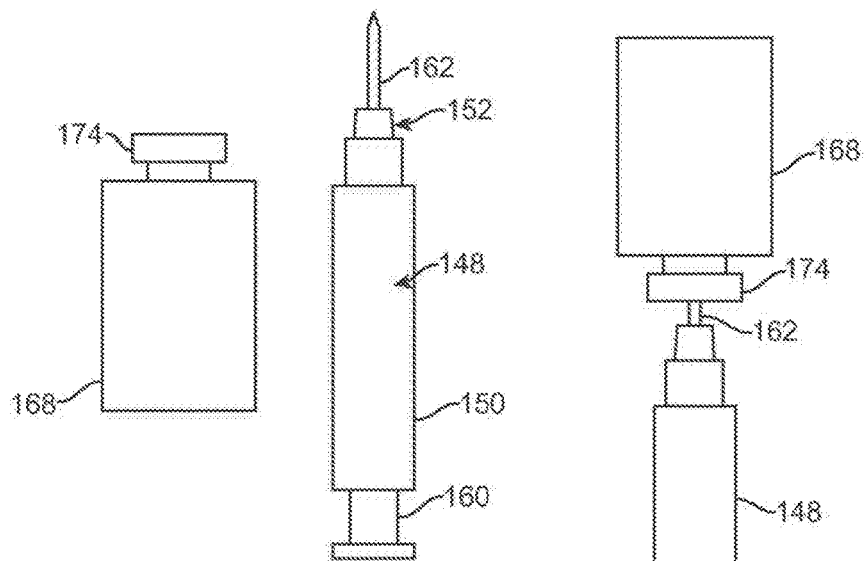
FIG. 8D
FIG. 8E
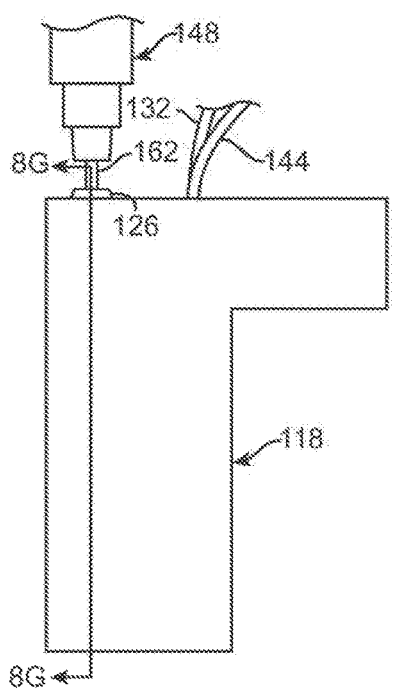
FIG. 8F
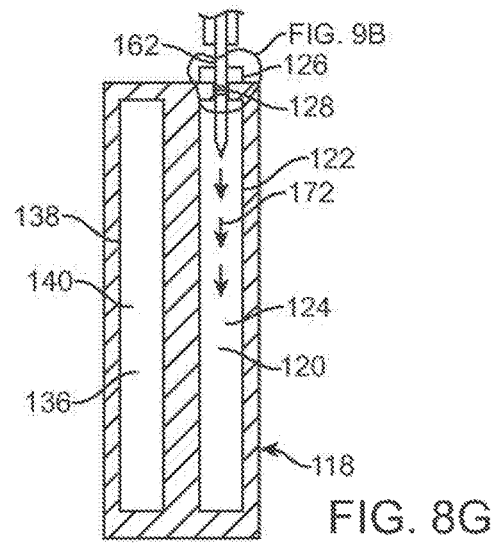
FIG. 8G

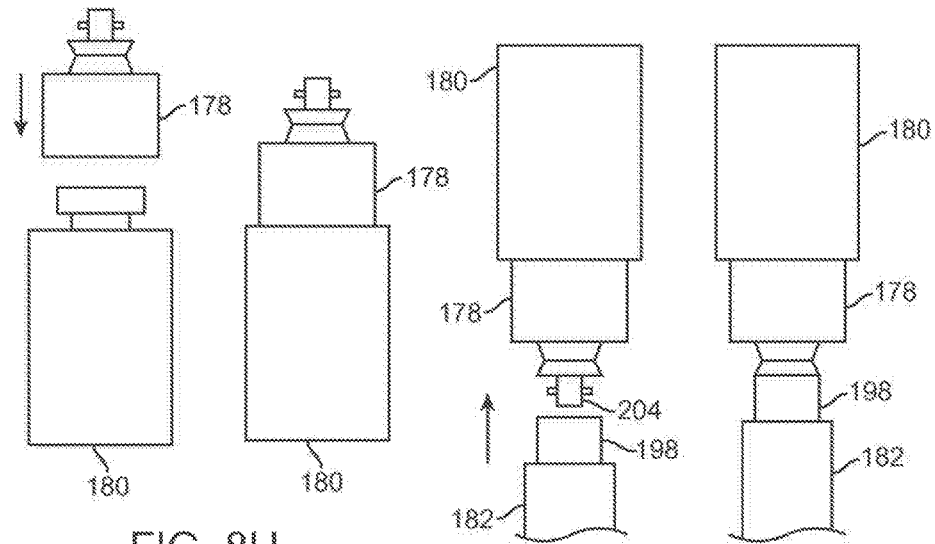
FIG. 8H
FIG. 8I
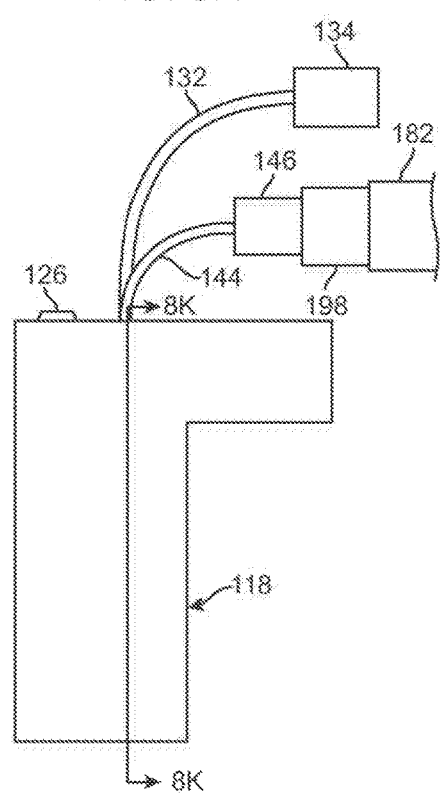
FIG. 8J
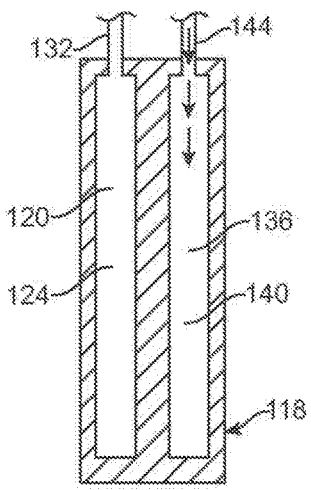
FIG. 8K

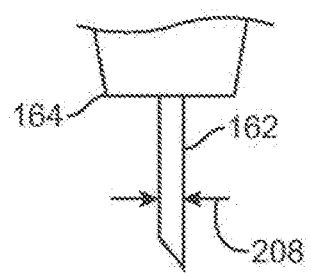
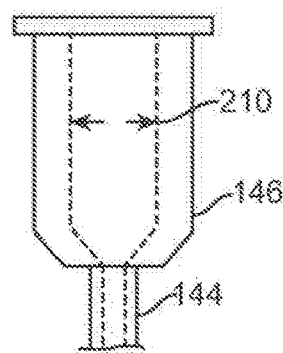
FIG. 9A
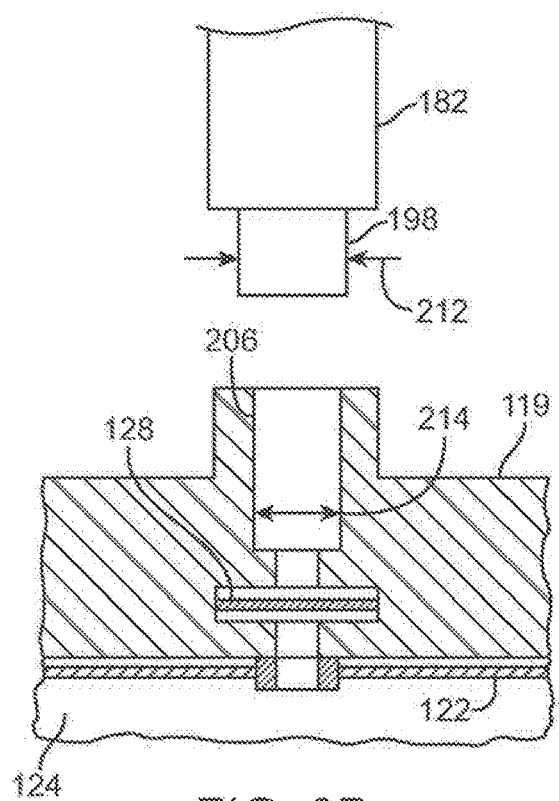
FIG. 9B

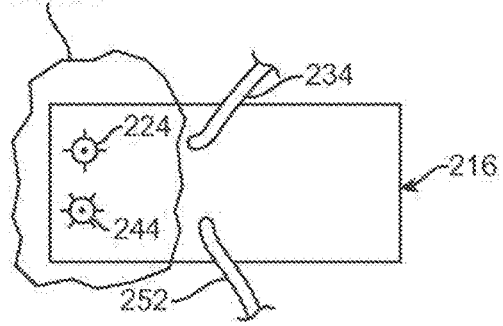
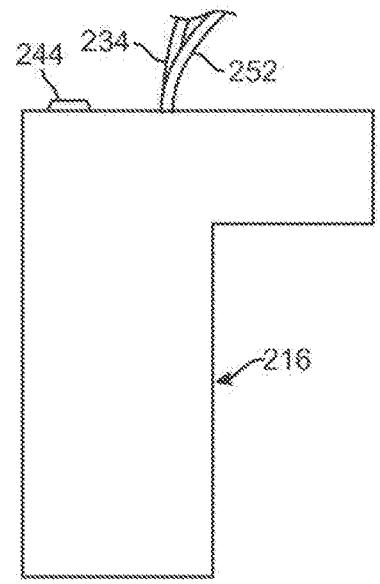
FIG. 10E        FIG. 10F
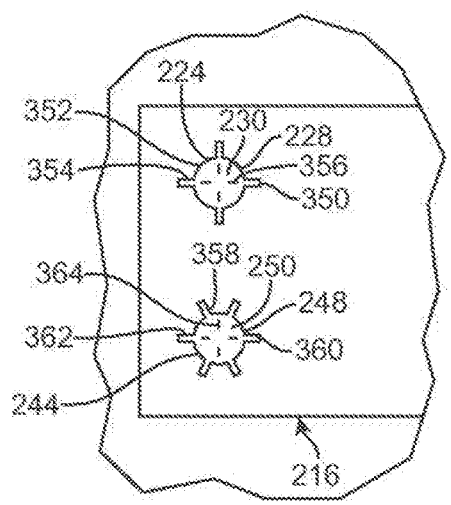
FIG. 10G

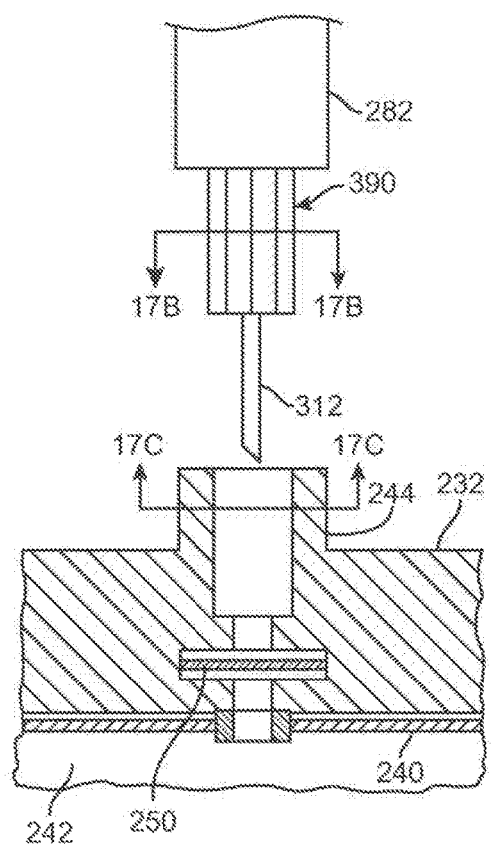
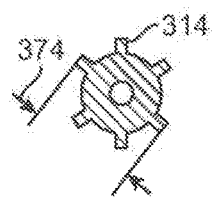
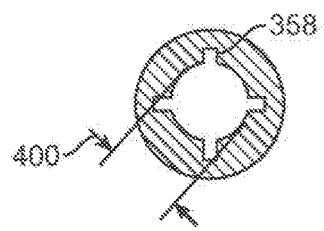
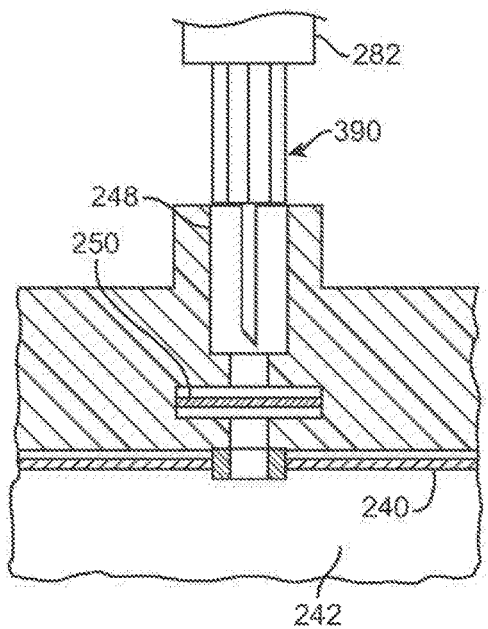
FIG. 17A
FIG. 17B
FIG. 17C
FIG. 17D

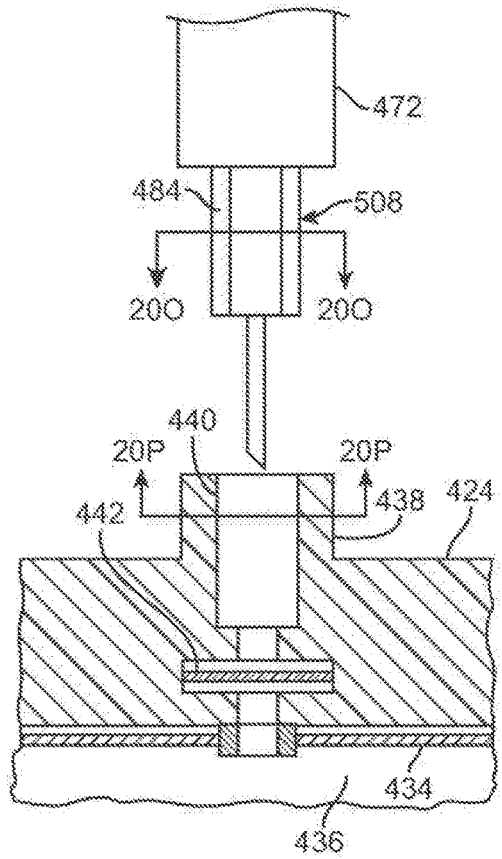
FIG. 20N
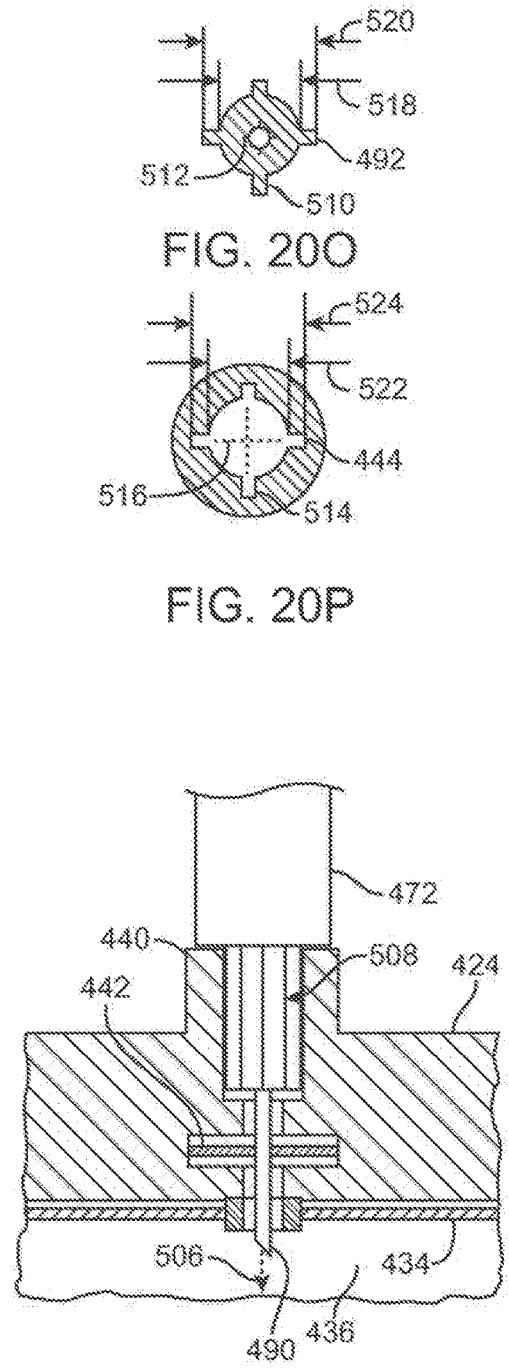
FIG. 20O
FIG. 20P
FIG. 20Q

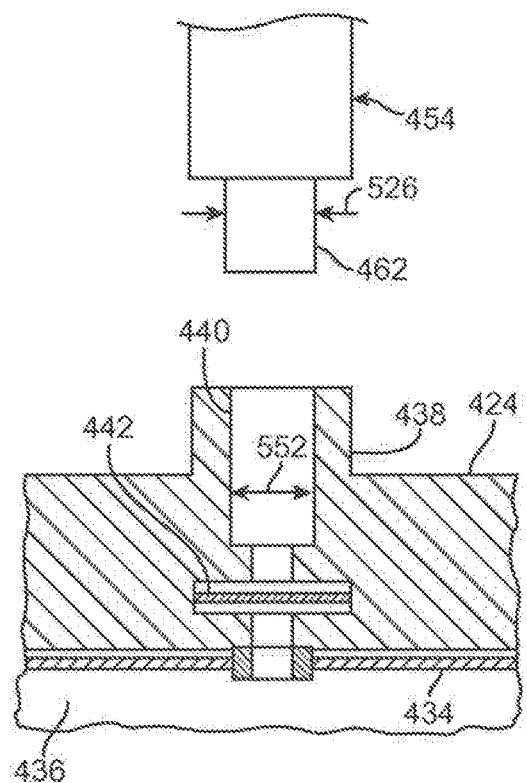
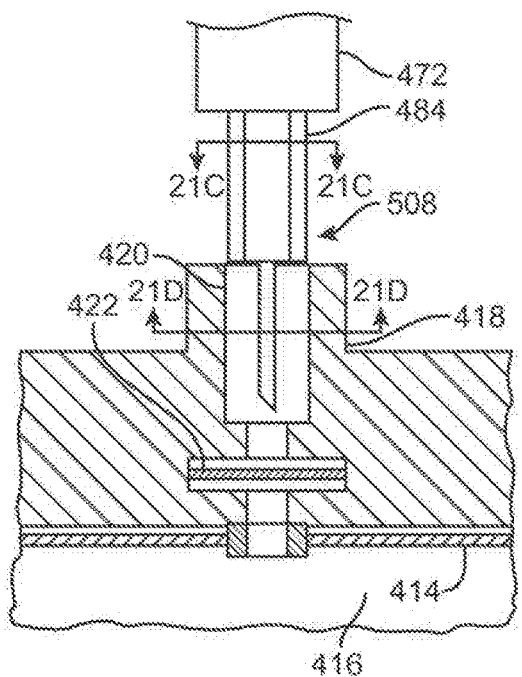
FIG. 21A
FIG. 21B
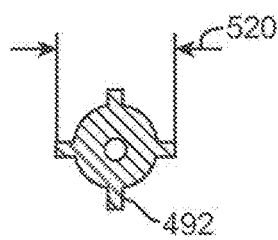
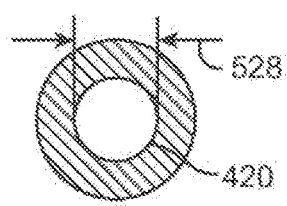
FIG. 21C
FIG. 21D

SYSTEMS INCLUDING VIAL ADAPTER FOR FLUID TRANSFER

RELATED APPLICATIONS

This application is a continuation of Ser. No. 14/936,979 filed Nov. 10, 2015, which in turn is a continuation of application Ser. No. 13/474,032 filed May 17, 2012, now U.S. Pat. No. 9,180,242 issued Nov. 10, 2015, each of which is hereby fully incorporated herein by reference.

BACKGROUND

A refillable pump device which can accurately dispense multiple fluids has applications which span a wide variety of fields. For example, a refillable pump device could be used for the delivery of multiple pharmaceutical agents in the medical device industry, for the delivery of multiple part adhesives in the chemical industry, for the simultaneous delivery of colorants, seasonings, or preservatives during food products manufacturing, or the like. Although these applications do not represent the complete range of potential uses for a refillable pump device which can accurately dispense multiple fluids they are representative of applications for which, e.g., control of a volumetric flow rate of each individual fluid being delivered may be important.

In the context of drug or medicament delivery from multiple reservoirs, the possibility for human error exists as a user refills a multiple fluid pump device. In such a case, for example, a user incorrectly refilling the internal reservoirs of the pump device can result in an improper drug or medicament dosing for the user. In order to minimize the potential for these and other problems, what is needed are both (a) reliable refilling methods and (b) appropriate mechanical interfaces at each appropriate port of the reservoirs of a pump device or cartridge thereof as well as at each appropriate port of the external reservoir.

SUMMARY

Some embodiments of a fluid transfer system may include a first receptacle reservoir having a first receptacle reservoir body, a first receptacle interior volume disposed within the first receptacle reservoir body, and a first receptacle reservoir interface in fluid communication with the first receptacle interior volume. The fluid transfer system may also include a second receptacle reservoir having a second receptacle reservoir body, a second receptacle interior volume disposed within the second receptacle reservoir body, and a second receptacle reservoir interface in fluid communication with the second receptacle interior volume. A first supply reservoir of the fluid transfer system may include a first supply reservoir body, a first supply interior volume disposed within the first supply reservoir body, a first fluid disposed within the first supply interior volume, and a first supply reservoir interface in fluid communication with the first supply interior volume. The first supply reservoir interface may be capable of coupling with the first receptacle reservoir interface in order to create a first fluid communication junction between the first supply interior volume and the first receptacle interior volume. The first supply reservoir interface may also be configured such that it is mechanically incompatible with the second receptacle reservoir interface so as to prevent the creation of a fluid communication junction between the two interfaces. A second supply reservoir of the fluid transfer system may include a second supply reservoir body, a second supply interior volume disposed within the second supply reservoir, a second fluid disposed within the second supply interior volume, and a second supply reservoir interface in fluid communication with the second supply interior volume. The second supply reservoir interface may be capable of coupling with the second receptacle reservoir interface in order to create a second fluid communication junction between the second supply interior volume and the second reservoir interior volume. The second supply reservoir interface may also be configured such that it is mechanically incompatible with the first receptacle reservoir interface so as to prevent the creation of a fluid communication junction between the two interfaces.

Some embodiments of a method for transferring fluids may include creating a first fluid communication junction between a first receptacle reservoir and a first supply reservoir by coupling a first receptacle reservoir interface to a first supply reservoir interface. A first fluid can then be transferred from the first supply reservoir to the first receptacle reservoir. The first supply reservoir interface may be configured such that it is mechanically incompatible with a second receptacle reservoir interface so as to prevent a fluid communication junction between the two interfaces. The method embodiment may also include creating a second fluid communication junction between a second receptacle reservoir and a second supply reservoir by coupling the second receptacle reservoir interface to a second supply reservoir interface. A second fluid can then be transferred from the second supply reservoir to the second receptacle reservoir. The second supply reservoir interface may be configured such that it is mechanically incompatible with the first receptacle reservoir interface so as to prevent the creation of a fluid communication junction between the two interfaces.

Some embodiments of a fluid transfer system may include a first pump reservoir having a first pump reservoir body, a first reservoir interior volume disposed within the first pump reservoir body, an input port, and a first output port. The input port may include a first reservoir septum disposed within the first pump reservoir body in some cases. The first output port is in fluid communication with the first reservoir interior volume. The fluid transfer system may also include a second pump reservoir having a second pump reservoir body, a second reservoir interior volume disposed within the second pump reservoir body, and a second output port. The second output port has a second output port adapter which may be in fluid communication with the second reservoir interior volume. The fluid transfer system may also include a syringe hub assembly having a syringe body, a syringe interior volume disposed within the syringe body, a first fluid contained within the syringe interior volume, and a hub assembly coupled to the syringe body. The hub assembly may include a needle which is capable of penetrating the first reservoir septum, but which is mechanically incompatible with the second output port adapter. The fluid transfer system may also include a diabetic pen reservoir assembly having a diabetic pen reservoir body, a pen interior volume disposed within the diabetic pen reservoir body, a second fluid contained within the pen interior volume, and a diabetic pen reservoir adapter. The diabetic pen reservoir adapter may be coupled to the diabetic pen reservoir body and configured to be mechanically compatible with the second output port adapter and mechanically incompatible with the input port.

Some embodiments of a method for transferring fluids may include creating a first fluid communication junction between a first pump reservoir and a syringe reservoir by piercing a first reservoir septum of a first input port of the first pump reservoir with a needle of a syringe hub assembly. The method includes transferring a first fluid from the syringe reservoir to the first pump reservoir. The needle may be configured such that it is mechanically incompatible with a second adapter of a second output port of a second pump reservoir so as to prevent the creation of a fluid communication junction between the syringe reservoir and the second output port. The method for transferring fluids may also include creating a second fluid communication junction between the second pump reservoir and a diabetic pen reservoir by coupling the second adapter of the second output port to a diabetic pen reservoir adapter. A second fluid can then be transferred from the diabetic pen reservoir to the second pump reservoir. The diabetic pen reservoir adapter may be configured such that it is mechanically incompatible with the first input port so as to prevent the creation of a fluid communication junction between the pen reservoir adapter and the first input port.

Some embodiments of a fluid transfer system may include a first pump reservoir having a first pump reservoir body and a first reservoir interior volume disposed within the first pump reservoir body. The first pump reservoir may include an input port which has a first reservoir septum that seals the first reservoir interior volume. The first pump reservoir may also include a first output port which is in fluid communication with the first reservoir interior volume. The fluid transfer system may also include a second pump reservoir having a second pump reservoir body and a second reservoir interior volume disposed within the second pump reservoir body. The second pump reservoir may also include a second output port which may be in fluid communication with the second reservoir interior volume. The fluid transfer system may also include a syringe hub assembly having a first syringe body and a first syringe interior volume disposed within the syringe body. A first fluid may be contained within the first syringe interior volume. A hub assembly may be coupled to the first syringe body. The hub assembly may include a needle which is capable of piercing the first reservoir septum in order to create a first fluid communication junction between the first syringe interior volume and the first pump interior volume. The needle may also be configured such that it is mechanically incompatible with the second output port adapter so as to prevent a fluid communication junction between the two components. The fluid transfer system may also include a second syringe reservoir which has a second syringe body, a second syringe interior volume which contains a second fluid and is disposed within the syringe body, and a second syringe port in fluid communication with the second syringe interior volume. The second syringe port may be configured such that it is capable of coupling to the second output port adapter so as to form a fluid communication junction. The second syringe port may also be configured such that it is mechanically incompatible with the input port so as to prevent a fluid communication junction between the two components.

Some embodiments of a method for transferring fluids may include creating a first fluid communication junction between a first pump reservoir and a first syringe reservoir by piercing a first reservoir septum of a first input port of the first pump reservoir with a needle of a syringe hub assembly. The method includes transferring a first fluid from the first syringe reservoir to the first pump reservoir. The needle may be configured such that it is mechanically incompatible with a second adapter of a second output port of a second pump reservoir so as to prevent the creation of a fluid communication junction between the first syringe reservoir and the second output port. The method for transferring multiple fluids may also include creating a second fluid communication junction between the second pump reservoir and a second syringe reservoir by coupling the second adapter of the second output port to a second syringe port. A second fluid can then be transferred from the second syringe reservoir to the second pump reservoir. The second syringe port may be configured such that it is mechanically incompatible with the first input port so as to prevent the creation of a fluid communication junction between the second syringe reservoir and the first input port.

Some embodiments of a vial adapter assembly may include a hub assembly having a hub body with a proximal section that is configured to mate with a syringe port and a needle sealingly secured to a distal section of the hub body. The vial adapter assembly may also include a vial adapter which may have a vial adapter body of resilient material and a distal cavity of sufficient inner dimensions to engage a vial reservoir. The distal cavity may also include at least one hooked clip which is disposed toward the distal cavity. The hooked clip may be configured such that after the vial reservoir is engaged by the hooked clip the needle is disposed in an interior volume and in fluid communication with an interior volume of the vial reservoir. The vial adapter assembly may also include an engagement feature which releasably secures the hub body to the vial adapter body such that the needle is disposed within and is in axial alignment of the distal cavity.

Some embodiments of a method for transferring fluids may include coupling a vial adapter assembly to a vial reservoir by inserting a spigot port located on the vial reservoir into a distal cavity of the vial adapter assembly such that a needle contained within the distal cavity punctures a vial septum disposed within the spigot port which creates a fluid communication junction between the vial reservoir and an interior channel of a hub assembly. The vial adapter assembly may be coupled to the vial reservoir by at least one hooked clip which engages the spigot port. The method for transferring fluids may further include attaching a syringe reservoir to the hub assembly and transferring a fluid from the vial reservoir to the syringe reservoir. The fluid transfer method may further include disengaging an engagement feature which releasably secures the hub assembly to the vial adapter assembly with the syringe reservoir remaining coupled to the hub assembly and the vial reservoir remaining secured to the vial adapter assembly.

Some embodiments of a fluid transfer system may include a first vial adapter assembly which may have a first hub assembly and a first vial adapter. The first hub assembly may include a first hub body having a proximal section capable of mating with a syringe port, and a distal section which is sealingly secured to a first needle. The first hub assembly may also include a first key feature that is mechanically compatible with a first keyed port of a first receptacle reservoir, but is mechanically incompatible with a second keyed port of a second receptacle reservoir. The first vial adapter may include a first vial adapter body having a first distal cavity which has an inner transverse dimension configured to couple to a first spigot of a first vial reservoir but not couple to a second spigot port of a second vial reservoir. The first distal cavity may also include at least one first hooked clip capable of engaging with the first spigot port but not the second spigot port. A first engagement feature may releasably secure the first hub body to the first vial adapter body such that the first needle is disposed within and is in axial alignment of the first distal cavity. The fluid transfer system may also include a second vial adapter assembly which may have a second hub assembly and a second vial adapter. The second hub assembly may include a second hub body which has a proximal section capable of mating with a syringe port, and a distal section which is sealingly secured to a second needle. The second hub assembly may also include a second key feature that is mechanically compatible with the second keyed port of the second receptacle reservoir, but is mechanically incompatible with the first keyed port of the first receptacle reservoir. The second vial adapter may include a second vial adapter body having a second distal cavity which has an inner transverse dimension configured to couple to the second spigot of the second vial reservoir but not couple to the first spigot port of the first vial reservoir. The second distal cavity may also include at least one second hooked clip capable of engaging with the second spigot port but not the first spigot port. A second engagement feature may releasably secure the second hub body to the second vial adapter body such that the second needle is disposed within and is in axial alignment of the second distal cavity.

Some embodiments of a method for transferring fluids may include providing a first vial adapter assembly. The first vial adapter assembly may include a first hub having a first needle extending from it and a first key feature which is mechanically compatible with a first keyed port of a first pump reservoir and which is mechanically incompatible with a second keyed port of a second pump reservoir. The first vial adapter assembly may also include a first vial adapter which has a first distal cavity which is configured to couple to a first spigot of a first vial reservoir but mechanically incompatible with a second spigot port of a second vial reservoir. The first vial adapter assembly may also include a first engagement feature which releasably secures the hub to the first vial adapter with the first needle disposed within the first distal cavity. The method for transferring fluids may also include providing a first vial reservoir which has a first vial internal volume that contains a first fluid. The first vial reservoir may also include a first spigot port which is in fluid communication with the first vial internal volume, and a first vial septum which is disposed within and seals the first spigot port. The fluid transfer method may further include providing a second vial adapter assembly. The second vial adapter assembly may include a second hub having a second needle extending from it and a second key feature which is mechanically compatible with the second keyed port of the first pump reservoir and which is mechanically incompatible with the first keyed port of the second pump reservoir. The second vial adapter assembly may also include a second vial adapter which may have a second distal cavity that is configured to couple to the second spigot of the second vial reservoir but mechanically incompatible with the first spigot port of the first vial reservoir. The second vial adapter assembly may also include a second engagement feature which releasably secures the second hub to the second vial adapter with the second needle disposed within the second distal cavity. The fluid transfer method may also include providing a second vial reservoir which may have a second vial internal volume that contains a second fluid. The second vial reservoir may also have a second spigot port which is in fluid communication with the second vial internal volume, and a second vial septum that is disposed within and seals the second spigot port. The fluid transfer method may further include coupling the first vial adapter assembly to the first vial reservoir by inserting the first spigot port into the first distal cavity so that the first tubular needle punctures the first vial septum and the first vial adapter assembly is mechanically captured to the first vial reservoir. The fluid transfer method may also include coupling the first syringe to the first hub and transferring the first fluid from the first vial reservoir to a first syringe reservoir of the first syringe through a lumen of the first tubular needle. The fluid transfer method may also include detaching the first hub from the first vial adapter by disengaging the first engagement feature. The fluid transfer method may also include coupling the second vial adapter assembly to the second vial reservoir by inserting the second spigot port into the second distal cavity so that the second tubular needle punctures the second vial septum and the second vial adapter assembly is mechanically captured to the second vial reservoir. The fluid transfer method may also include coupling a second syringe reservoir to the second hub and then transferring the second fluid from the second vial reservoir to a second syringe reservoir of the second syringe through a lumen of the second needle. The fluid transfer method may also include detaching the second hub from the second vial adapter by disengaging the second engagement feature.

Some embodiments of fluid transfer system may include a first hub assembly and a first keyed port. The first hub assembly may include a first hub body that has a proximal section that is configured to mate with a syringe port. The first hub assembly may also include a first hub key feature which is disposed on a perimeter of the first hub body, and which is configured to couple to a first keyed port of a first receptacle reservoir but which is mechanically incompatible with a second keyed port of a second receptacle reservoir. A first needle including an elongated tubular member of high strength material may be sealingly secured to a distal section of the first hub body. The first keyed port may include a first channel which is in fluid communication with an interior volume of a first receptacle reservoir. The first channel may be configured such that it can accommodate the insertion of the first hub body. A first septum is disposed within and seals the first channel, and is positioned at a depth within the first channel that is substantially equal to or greater than a distance that the first needle extends from the first hub. The first keyed port may also include a first port key feature which is disposed on an inner perimeter of the first channel, and which is configured to couple with the first hub key feature but which is mechanically incompatible with a second hub key feature. Other embodiments of the fluid transfer system may include a second hub assembly and a second keyed port. The second hub assembly may include a second hub body which has a proximal section that is configured to couple with a syringe port. The second hub assembly may also include a second hub key feature which is disposed on a perimeter of the second hub body, and which is configured to couple to the second keyed port of the first receptacle reservoir but which is mechanically incompatible with the first keyed port of the first receptacle reservoir. A second needle including an elongate tubular member of high strength material may be sealingly secured to a distal section of the second hub body. The second keyed port may include a second channel which is in fluid communication with an interior volume of a second receptacle reservoir. The second channel may be configured such that it can accommodate the insertion of the second hub body. A second septum is disposed within and seals the second channel, and is positioned at a depth within the second channel that is substantially equal to or greater than a distance that the second needle extends from the second hub. The second keyed port may also include a second port key feature which is disposed on an inner perimeter of the second channel, and which is configured to couple with the second hub key feature but which is mechanically incompatible with the first hub key feature.

Some embodiments of a method for transferring fluids may include creating a first fluid communication junction between a first receptacle reservoir and a first supply reservoir by coupling a first receptacle keyed interface to a mechanically compatible first supply keyed interface. A first fluid may then be transferred from the first supply reservoir into the first receptacle reservoir through the first fluid communication junction. The first supply keyed interface is configured to be mechanically incompatible with a second receptacle keyed interface so as to prevent a fluid communication junction between the two interfaces. Other embodiments for the method may include creating a second fluid communication junction between a second receptacle reservoir and a second supply reservoir by coupling the second receptacle keyed interface to a mechanically compatible second supply keyed interface. A second fluid can then be transferred from the second supply reservoir into the second receptacle reservoir through the second fluid communication junction. The second supply keyed interface is configured to be mechanically incompatible with the first receptacle keyed interface so as to prevent a fluid communication junction between the two interfaces.

Some embodiments of a fluid transfer system may include a first vial adapter assembly, a first vial reservoir, a first receptacle reservoir, a second vial adapter assembly, a second vial reservoir, and a second receptacle reservoir. The first vial adapter assembly may include a first hub assembly, a first vial adapter, and a first engagement feature. The first vial adapter assembly may include a first hub having a first hub body. The first hub body may include a proximal section which is capable of mating with a syringe port and a distal section which is sealingly secured to a first needle. The first hub assembly may also include a first hub key feature which is disposed on a perimeter of the first hub body and which is mechanically compatible with a first keyed port of a first receptacle reservoir, but which is mechanically incompatible with a second keyed port of a second receptacle reservoir. The first vial adapter assembly may also include a first vial adapter which has a first vial adapter body. The first vial adapter body may incorporate a first distal cavity which has an inner transverse dimension configured to couple to a first spigot port of a first vial reservoir, but not couple to a second spigot port of a second vial reservoir. The first distal cavity may also include a first hooked clip configured to engage a first spigot port but not a second spigot port. The first vial adapter assembly may also include a first engagement feature which releasably secures the first hub body to the first vial adapter body such that the first needle of the first hub assembly is disposed within and is in axial alignment with the first distal cavity of the first vial adapter. The first vial reservoir has a first vial reservoir body which may include a first vial internal volume disposed within it. The first vial reservoir may also include a first spigot port in fluid communication with the first vial internal volume, a first vial septum disposed within the first spigot port, and a first fluid disposed within the first vial internal volume. The first receptacle reservoir may include an interior volume and a first keyed port. The first keyed port may have a first channel which is in fluid communication with the interior volume of the first receptacle reservoir, and a first septum which is disposed within and seals the first channel at a depth which is greater than or equal to a distance which the first needle extends from the first hub body. The first keyed port may also have a first port keyed feature which is disposed on a perimeter of the first channel and which is mechanically compatible with the first hub key feature. The second vial adapter assembly may include a second hub assembly, a second vial adapter, and a second engagement feature. The second vial adapter assembly may include a second hub having a second hub body. The second hub body may include a proximal section which is capable of mating with a syringe port and a distal section which is sealingly secured to a second needle. The second hub assembly may also include a second hub key feature which is disposed on a perimeter of the second hub body and which is mechanically compatible with the second keyed port of the second receptacle reservoir, but which is mechanically incompatible with the first keyed port of the first receptacle reservoir. The second vial adapter assembly may also include a second vial adapter which has a second vial adapter body. The second vial adapter body may incorporate a second distal cavity which has an inner transverse dimension configured to couple to the second spigot port of the second vial reservoir, but not to couple to the first spigot port of the first vial reservoir. The second distal cavity may also include a second hooked clip configured to engage the second spigot port but not the first spigot port. The second vial adapter assembly may also include a second engagement feature which releasably secures the second hub body to the second vial adapter body such that the second needle of the second hub assembly is disposed within and is in axial alignment with the second distal cavity of the second vial adapter. The second vial reservoir has a second vial reservoir body which may include a second vial internal volume disposed within it. The second vial reservoir may also include the second spigot port which is in fluid communication with the second vial internal volume, a second vial septum disposed within the second spigot port, and a second fluid disposed within the second vial internal volume. The second receptacle reservoir may include an interior volume and a second keyed port. The second keyed port may have a second channel which is in fluid communication with the interior volume of the second receptacle reservoir, and a second septum which is disposed within and seals the second channel at a depth which is greater than or equal to a distance which the second needle extends from the second hub body. The second keyed port may also have a second port keyed feature which is disposed on a perimeter of the second channel and which is mechanically compatible with the second hub key feature.

Some embodiments of a fluid transfer system may include a first pump reservoir, a second pump reservoir, a diabetic pen reservoir assembly, and a syringe hub assembly. The first pump reservoir may include a first reservoir body having a first reservoir interior volume which is disposed within the first reservoir body and which is capable of containing fluid. The first pump reservoir may also include a first input port which has a first channel that is in fluid communication with the first reservoir interior volume. The first input port may also include a first septum that is disposed within and seals the first channel. A tubular bayonet needle may be configured to be inserted through the first septum such that an inner lumen of the bayonet needle is in fluid communication with the first reservoir interior volume. The first pump reservoir may also include a first output port which has a first fluid line that is in fluid communication with the first reservoir interior volume, and a first output port adapter which is secured to and in fluid communication with the first fluid line. The second pump reservoir may include a second pump reservoir body having a second reservoir interior volume which is disposed within the second reservoir body and which is capable of containing fluid. The second pump reservoir may also include a second input port which has a second channel which is in fluid communication with the second reservoir interior volume. A second septum is disposed within and seals the second channel, and a second key feature is disposed on a perimeter of the second channel. The second pump reservoir may also include a second output port comprising a second fluid line which is in fluid communication with the second reservoir interior volume, and a second output port adapter which is secured to and in fluid communication with the second fluid line. The diabetic pen reservoir assembly may include a diabetic pen reservoir body which has a pen interior volume disposed within it. A first fluid may be contained within the pen interior volume. The diabetic pen reservoir assembly may also include a pen port which is in fluid communication with the pen interior volume. The pen port may be configured to couple to the bayonet needle in order to create a second fluid communication junction between the pen interior volume and the first interior volume. The pen port is mechanically incompatible with the first channel of the first input port so as to prevent a fluid communication junction between the two components. The syringe hub assembly may include a syringe and a hub assembly. The syringe may include a syringe which has a syringe body, a syringe interior volume disposed within the syringe body, a second fluid contained within the syringe interior volume, and a syringe port. The hub assembly may include a hub body having a proximal section secured to the syringe port, and a distal section of the hub body which is sealingly secured to a needle. The hub assembly may also include a hub key feature which is disposed on a perimeter of the hub body, and which is mechanically compatible with the second input port so as to allow for the coupling of the hub assembly to the second input port and which is mechanically incompatible with the first input port. The needle is configured to pierce the second reservoir septum in order to create a second fluid communication junction between the syringe interior volume and the second interior volume, but is configured to be mechanically incompatible with the second output port adapter so as to prevent the creation of a fluid communication junction between the two components.

Some embodiments of a method for transferring fluids may include creating a first fluid communication junction between a first pump reservoir and a diabetic pen reservoir by coupling a diabetic pen port of the diabetic pen reservoir to a bayonet needle adapter. The bayonet needle adapter is secured to the first pump reservoir by a bayonet needle which may be configured to be disposed through a first reservoir septum of a first port of the first pump reservoir. A first fluid may then be transferred from the diabetic pen reservoir to the first pump reservoir through the first fluid communication junction. The diabetic pen port is configured to be mechanically incompatible with a second keyed input port so as to prevent the creation of a fluid communication junction between the two components. The method for transferring fluids may further include inserting a keyed hub assembly coupled to a syringe reservoir into the second keyed input port of a second pump reservoir such that a needle of the keyed hub assembly penetrates a second reservoir septum thereby creating a second fluid communication junction between the second pump reservoir and the syringe reservoir. The keyed hub assembly is mechanically incompatible with the first input port so as to prevent the creation of a fluid communication junction between the two components.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

The drawings illustrate embodiments of the technology and are not limiting. For clarity and ease of illustration, the drawings may not be made to scale and, in some instances, various aspects may be shown exaggerated or enlarged to facilitate an understanding of particular embodiments.

FIG. 3A is a view in transverse section of the dual reservoir cartridge embodiment of FIG. 3 showing a first input port in fluid communication with a first pump reservoir and a second input port in fluid communication with a second pump reservoir.

FIG. 3B is a view in transverse section of the dual reservoir cartridge embodiment of FIG. 3 showing a first output port in fluid communication with the first pump reservoir and a second output port in fluid communication with the second pump reservoir.

FIG. 5A shows the dual reservoir cartridge embodiment of FIG. 4.

FIG. 5B is a view in transverse section of the dual reservoir cartridge embodiment of FIG. 5A showing a first input port in fluid communication with a first pump reservoir.

FIG. 5C is a view in transverse section of the dual reservoir cartridge embodiment of FIG. 5A showing a first output port in fluid communication with the first pump reservoir and a second output port in fluid communication with a second pump reservoir.

FIG. 6E shows the vial reservoir embodiment of FIG. 6D and a syringe hub assembly embodiment.

FIG. 6F shows a needle of the syringe hub assembly embodiment of FIG. 6E inserted into the spigot port of the vial reservoir embodiment of FIG. 6D and a plunger of the syringe reservoir embodiment being activated.

FIG. 6G shows the needle of the syringe hub assembly embodiment of FIG. 6F inserted into an input port of the dual reservoir cartridge embodiment of FIG. 6A.

FIG. 6H is a view in transverse section of the dual reservoir cartridge embodiment of FIG. 6G showing a first fluid being transferred from the syringe reservoir embodiment to a first pump reservoir of the dual reservoir cartridge of FIG. 6A.

FIG. 6I shows the diabetic pen reservoir embodiment and female luer adapter embodiment both of FIG. 6B.

FIG. 6J shows the diabetic pen reservoir embodiment and female luer adapter embodiment of FIG. 6I coupled to form a pen reservoir assembly embodiment.

FIG. 6K shows the pen reservoir assembly embodiment of FIG. 6J coupled to a male luer adapter of a second output port of the dual reservoir cartridge of FIG. 6A.

FIG. 6L is a view in transverse section of the multiple reservoir cartridge embodiment of FIG. 6K showing a second fluid being transferred from a diabetic pen reservoir to a second pump reservoir.

FIG. 8A is a perspective view of a dual reservoir cartridge embodiment with a single input port and multiple output ports.

FIG. 8B shows embodiments of a first syringe reservoir, a hub assembly, and a first vial reservoir.

FIG. 8C shows embodiments of a vial adapter, a second vial reservoir, and a second syringe reservoir.

FIG. 8D depicts the first vial reservoir embodiment of FIG. 8B and embodiments of the first syringe reservoir and hub assembly of FIG. 8B in a coupled state.

FIG. 8E shows a needle of the first syringe hub assembly embodiment of FIG. 8B inserted into a first spigot port of the vial reservoir embodiment of FIG. 8B and a plunger of the first syringe hub assembly being activated.

FIG. 8F shows the needle of the first syringe hub assembly embodiment of FIG. 8D inserted into an input port of the dual reservoir cartridge embodiment of FIG. 8A.

FIG. 8G is a view in transverse section of the dual reservoir cartridge embodiment of FIG. 8F showing a first fluid being transferred from the first syringe hub assembly embodiment of FIG. 8D to a first pump reservoir of the dual reservoir cartridge embodiment of FIG. 8A.

FIG. 8H shows the vial adapter embodiment and second vial reservoir embodiment of FIG. 8C being coupled together in order to form the vial adapter reservoir assembly embodiment.

FIG. 8I depicts the second syringe reservoir embodiment of FIG. 8C being coupled to the vial adapter reservoir assembly embodiment of FIG. 8H.

FIG. 8J depicts the second syringe reservoir embodiment of FIG. 8I coupled to a female luer adapter of the second output port of the dual reservoir cartridge embodiment of FIG. 8A.

FIG. 8K is a view in transverse section of the dual reservoir cartridge embodiment of FIG. 8J showing a second fluid being transferred from the second syringe reservoir embodiment to a second pump reservoir of the dual reservoir cartridge.

FIG. 9A illustrates an embodiment of the mechanical incompatibility between the syringe hub assembly embodiment of FIG. 8D and the male luer adapter of the first output port of the dual reservoir cartridge embodiment of FIG. 8A.

FIG. 9B illustrates an embodiment of the mechanical incompatibility between the second syringe reservoir embodiment of FIG. 8C and the input port of the dual reservoir cartridge embodiment shown in FIG. 8A.

FIG. 10E depicts a top view of the dual reservoir cartridge embodiment of FIG. 10A.

FIG. 10F is a side view of the dual reservoir cartridge embodiment of FIG. 10A.

FIG. 10G is an enlarged view of the multiple reservoir cartridge of FIG. 10E showing a first keyed input port and a second keyed input port.

FIG. 17A shows the second keyed port embodiment of the dual reservoir cartridge of FIG. 14C and the coupled first syringe reservoir embodiment and first hub assembly embodiment of FIG. 13D.

FIG. 17B is a view in transverse section of the first hub assembly embodiment of FIG. 17A.

FIG. 17C is a view in transverse section of the second keyed port embodiment of FIG. 17A.

FIG. 17D illustrates an embodiment of the mechanical incompatibility between the first hub assembly embodiment of FIG. 17A and the second keyed port embodiment of FIG. 17A.

FIG. 20N shows the syringe hub assembly embodiment of FIG. 20I and a second keyed input port embodiment of the dual reservoir cartridge of FIG. 20M.

FIG. 20O is a view in transverse section of the syringe hub assembly embodiment of FIG. 20N.

FIG. 20P is a view in transverse section of the second keyed input port embodiment of FIG. 20N.

FIG. 20Q shows the syringe hub assembly embodiment of FIG. 20N inserted into the second keyed input port embodiment of FIG. 20N.

FIG. 21A illustrates an embodiment of the mechanical incompatibility between the diabetic pen reservoir embodiment of FIG. 20B and the second keyed input port embodiment of the dual reservoir cartridge of FIG. 20M.

FIG. 21B illustrates an embodiment of the mechanical incompatibility between the coupled syringe reservoir and hub assembly embodiment of FIG. 20I and a first input port embodiment of the dual reservoir cartridge FIG. 20M.

FIG. 21C is a view in transverse section of the hub assembly embodiment of FIG. 21B.

FIG. 21D is a view in transverse section of the first input port embodiment of FIG. 21B.

DETAILED DESCRIPTION

Figure 1:
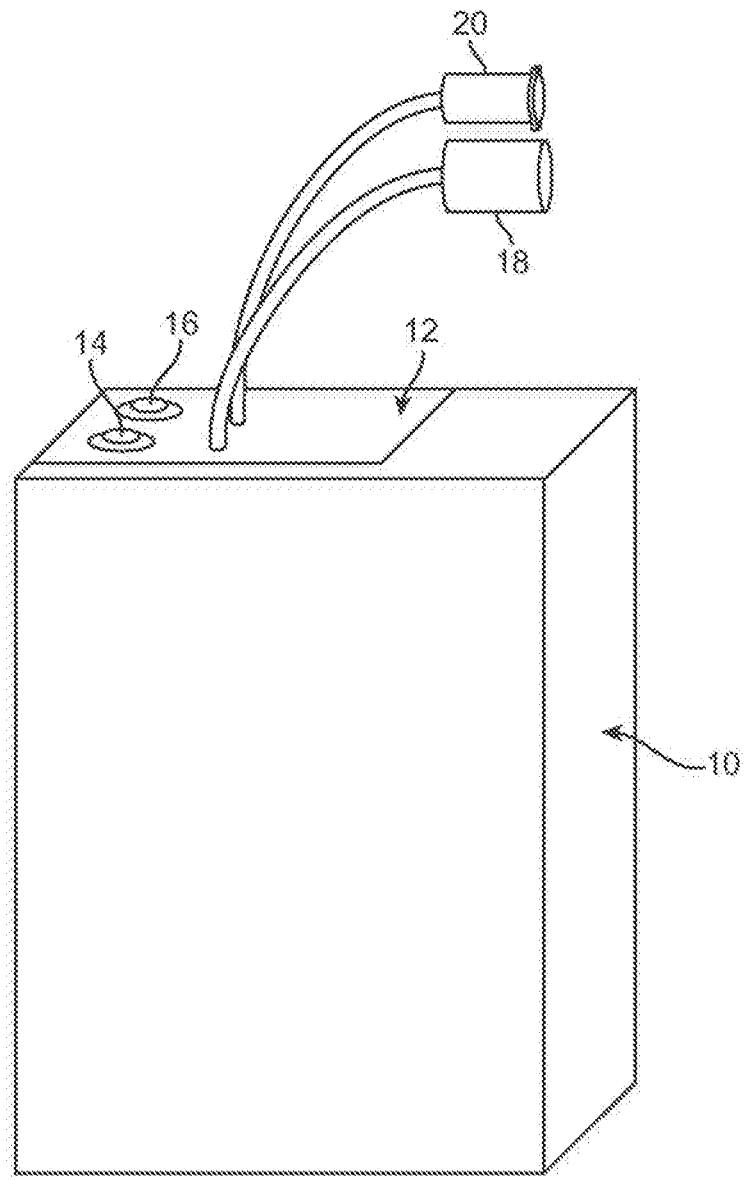
FIG. 1 is a perspective view of an embodiment of a pump device.

As discussed above, a refillable pump device which can accurately dispense multiple fluids has applications which span a wide variety of fields. The ability of the refillable pump device to dispense multiple fluids (including liquids and/or gasses) may require multiple internal reservoirs within the pump device, each with distinguishable input and output ports in some cases. The input port for each internal reservoir may serve as an access site via which a user can refill the given internal reservoir. In turn, the output port for each internal reservoir may serve as a means by which a liquid or gas can exit the pump device and be delivered to a target area. Alternatively, either output port may be used in order to refill the respective internal reservoir in fluid communication with respectively therewith.

In the case where the refillable pump device is used as a medical device for the delivery of multiple agents or medicaments, including, e.g., multiple pharmaceutical or bioactive agents wherein different volumetric doses of the different agents may be delivered to a patient or caregiver, then the proper refilling of each internal reservoir of the pump device by the user may be particularly important.

When a pump device is activated, the volumetric flow rate of a fluid from each internal reservoir may be calibrated to deliver the appropriate distinguishable doses for each agent over a desired temporal period; e.g., the period during which the pump device is activated. For diabetic indications, the patient or caregiver is typically the user who refills the pump device with insulin or other suitable medications which may include Symlin®, Byetta®, Bydureon®, Victoza®, Glucagon®, saline, antibiotics, or any other suitable medications which may be delivered subdermally or by other suitable delivery methods. The patient or caregiver can refill the respective internal reservoirs of the pump device from a variety of different external reservoir configurations which can include drug vials, insulin pen vials, and insulin pen assemblies.

For a case where a pump device includes a disposable cartridge, it may be desirable to isolate agent reservoirs and agent ports in the cartridge which can detach from a body of the pump device. The ability of the user (e.g., the patient or caregiver) to detach the cartridge from the body of the pump device may allow, for example, cartridge replacement after a specified number of uses or after the agent has been partially or completely dispensed therefrom. The pump device body may contain features such as a fluid pumping mechanism, feedback control circuitry, and patient or caregiver user interface through which the pump device may be controlled. The accompanying cartridge may contain single or multiple agent reservoirs and a single or multiple input and output ports. In the case of a cartridge having multiple reservoirs, multiple input ports may be used in order to refill the multiple internal reservoirs, whereas the multiple output ports may be used to deliver multiple agents to the patient or caregiver. For some method embodiments, it may be desirable to refill one or more of the multiple internal reservoirs using one or more of the multiple output ports.

Transferring fluids from supply reservoirs such as, e.g., syringes, vials, and insulin pens to receptacle reservoirs such as, e.g., the internal reservoirs of a pump cartridge may be accomplished any number of methods. For instance, the fluid could be transferred from a supply reservoir to a receptacle reservoir by decreasing the fluid pressure within an interior volume of the receptacle reservoir with a pump device. The fluid could also be transferred from a supply reservoir into a receptacle reservoir by increasing the fluid pressure within an interior volume of the supply reservoir with a pump device. The fluid could also be transferred from a supply reservoir to a receptacle reservoir by decreasing an internal volume of the supply reservoir with a moveable plunger that is contained within the internal volume of the supply reservoir. The fluid also could be transferred from a supply reservoir to a receptacle reservoir by increasing the internal volume of the receptacle reservoir with a moveable plunger contained within the internal volume of the receptacle reservoir.

FIGS. 1-3B illustrate an embodiment of a pump system including a multi-reservoir cartridge 12 having multiple input and output ports which can be inserted into the pump device 10 in order to deliver multiple pharmaceutical agents to a patient or caregiver. For some embodiments, it may be possible for the pump device to simultaneously deliver different doses of the different agents to the patient or caregiver. In some cases, the patient or caregiver can refill the cartridge receptacle reservoirs with the different agents from multiple supply reservoirs. It may be desirable in some cases for the various ports of the supply reservoirs and receptacle reservoirs be configured such that the possibility of patient or caregiver filling a given receptacle reservoir with an agent from the wrong supply reservoir is mechanically prevented.

Figure 2:
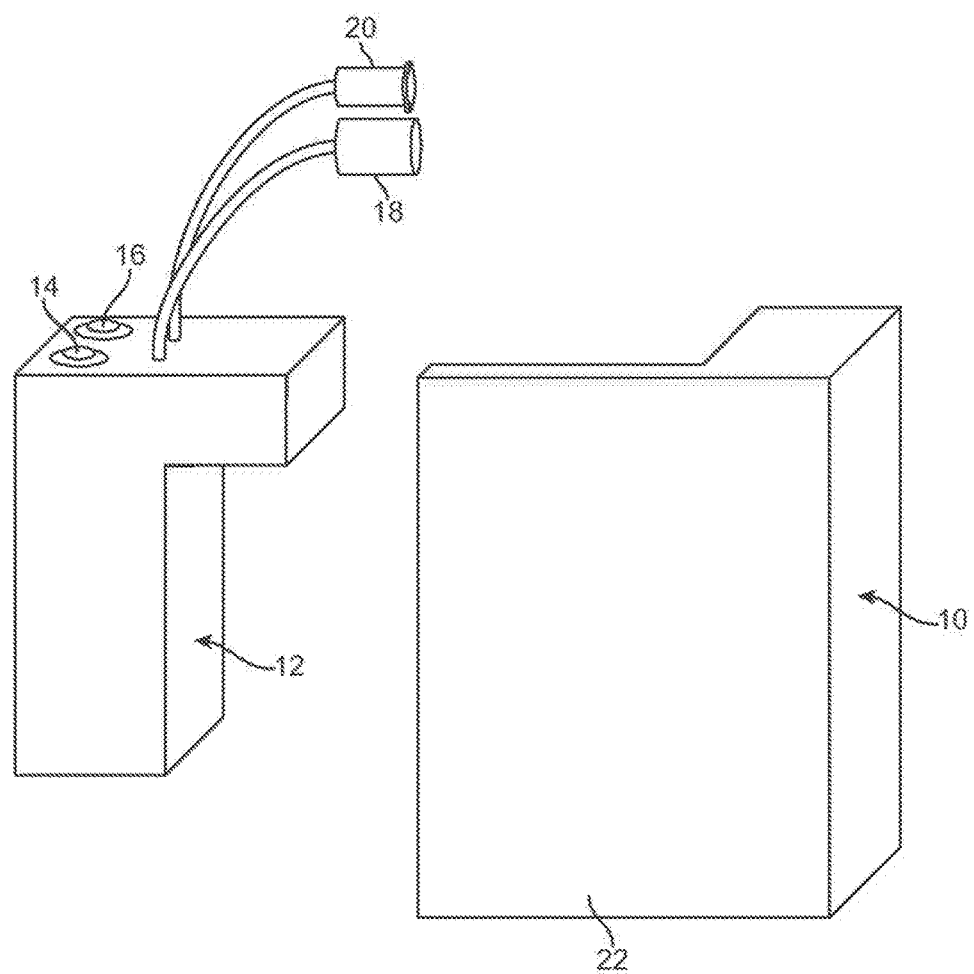
FIG. 2 shows the pump device embodiment of FIG. 1 with a dual reservoir cartridge embodiment removed from the pump device.
Figure 3:
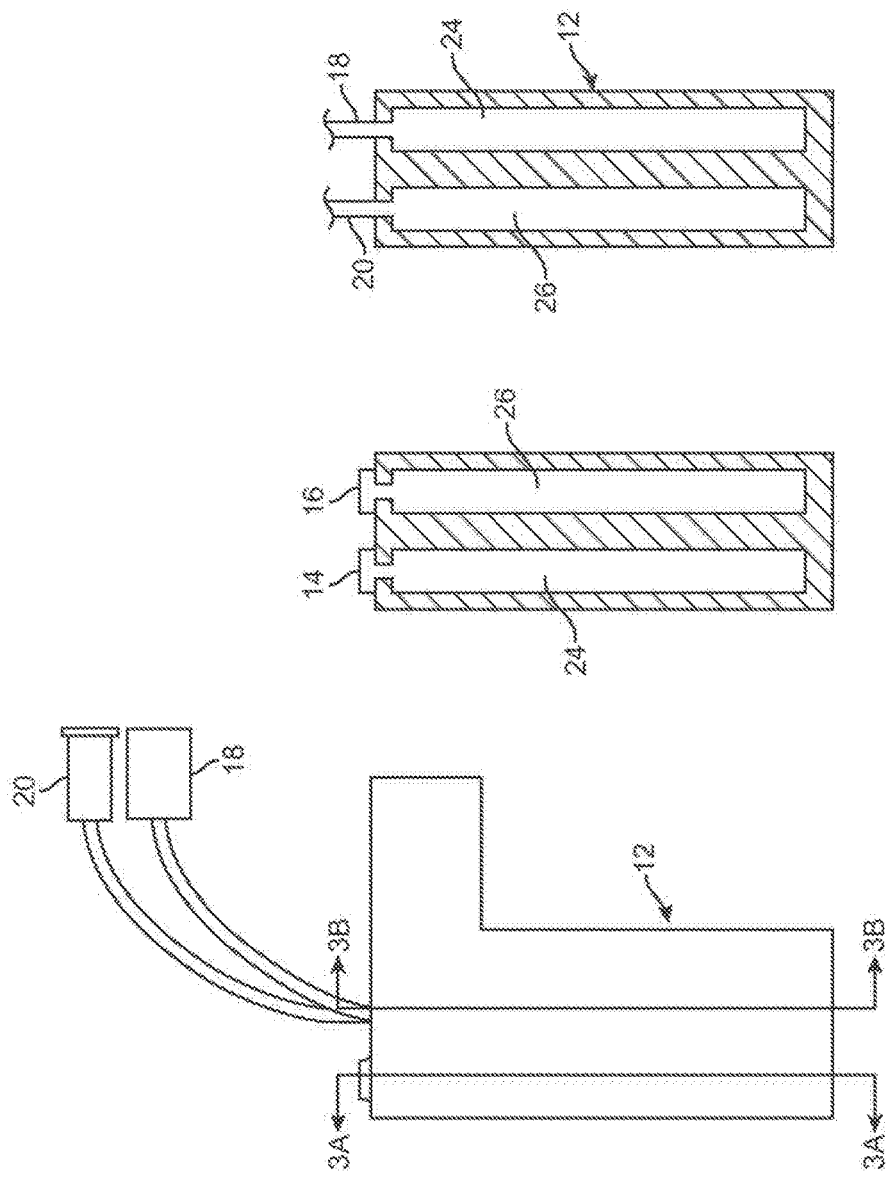
FIG. 3 shows the dual reservoir cartridge embodiment of FIG. 2.

FIG. 1 is a perspective view of a pump device embodiment 10 with a multiple reservoir cartridge embodiment 12 having multiple input and output ports. The multiple reservoir cartridge incorporates embodiments of a first input port 14, a second input port 16, a first output port 18, and a second output port 20. FIG. 2 shows the pump device 10 of FIG. 1 with the multiple reservoir cartridge 12 separated from the pump device body 22. FIG. 3 is a frontal view of the multiple reservoir cartridge 12 of FIG. 2. FIG. 3A is a transverse sectional view of the multiple reservoir cartridge 12 of FIG. 3 showing the first input port 14 which is in fluid communication with a first pump reservoir 24, and the second input port 16 which is in fluid communication with a second pump reservoir 26. FIG. 3B is a transverse sectional view of the multiple reservoir cartridge 12 of FIG. 3 showing the first output port 18 which is in fluid communication with the first pump reservoir 24, and the second output port 20 which is in fluid communication with the second pump reservoir 26.

Figure 4:
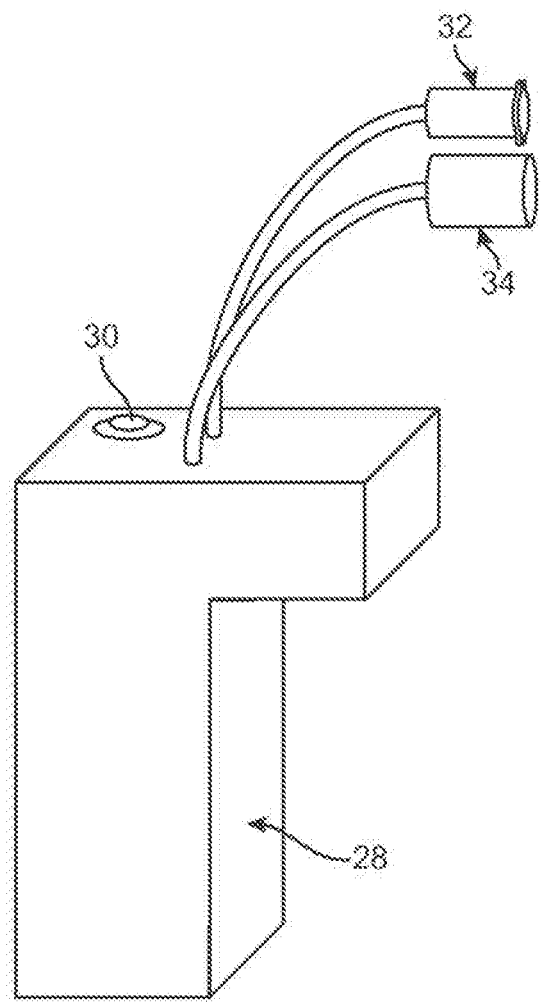
FIG. 4 is a perspective view of an embodiment of a dual reservoir cartridge.

FIG. 4 is a perspective view of a multiple reservoir cartridge 28 embodiment with a single input port and multiple output ports. The multiple reservoir cartridge 28 incorporates embodiments of an input port 30, a first output port 32, and a second output port 34. FIG. 5A is a frontal view of the multiple reservoir cartridge 28 of FIG. 4. FIG. 5B is a transverse sectional view of the multiple reservoir cartridge 28 of FIG. 5A showing the input port 30 which is in fluid communication with a second pump reservoir 38. FIG. 5C is a transverse sectional view of the multiple reservoir cartridge embodiment 28 of FIG. 5A showing the first output port 32 which is in fluid communication with a first pump reservoir 36, as well as the second output reservoir 34 which is in fluid communication with the second pump reservoir 38.

The multiple reservoir cartridges are distinguished by the configuration of each fluid interface port which is connected to each pump reservoir of the cartridge embodiment. A user may refill the pump reservoirs from multiple supply reservoirs with each fluid being delivered to its intended respective pump reservoir. Thus, the various fluid interface ports of the supply reservoirs and pump reservoirs may be mechanically configured such that the possibility of a user filling a given pump reservoir with an agent from the wrong supply reservoir is prevented. FIGS. 6A-7B illustrate such a fluid transfer system wherein multiple fluids may be transferred selectively from multiple supply reservoirs into the respective pump reservoirs of the multiple reservoir cartridge embodiment 28.

Figure 6A:
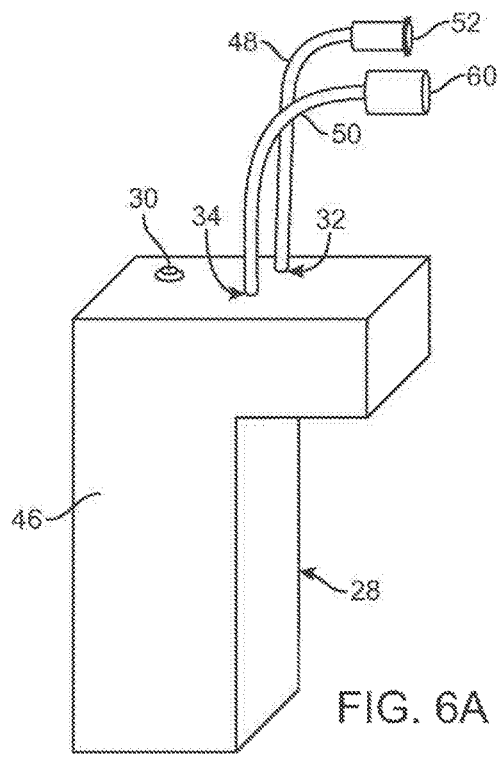
FIG. 6A is a perspective view of the dual reservoir cartridge embodiment.

FIGS. 6A and 6H show the multiple reservoir cartridge 28 which may include a first pump reservoir 36 having a first pump reservoir body 40, a first reservoir interior volume 42 disposed within the first pump reservoir body 40, an input port 30 and a first output port 32. The first pump reservoir body 40 may be fabricated from a thin flexible material. The input port 30 may include a reservoir septum 44 which is disposed within a multiple reservoir cartridge body 46. The reservoir septum 44 may be configured to seal the first reservoir interior volume 42. The first output port 32 is in fluid communication with the first reservoir interior volume 42. The first output port 32 includes a first fluid line 48 which may be a flexible tube with an inner fluid lumen which connects the first reservoir interior volume 42 to a first output port adapter 52.

The fluid transfer system may also include a second pump reservoir 38 of the multiple reservoir cartridge 28, as illustrated in FIGS. 6H and 6L. The second pump reservoir 38 may include a second pump reservoir body 54, a second reservoir interior volume 56 disposed within a second pump reservoir body 54, and a second output port 34 (FIG. 6A). The second pump reservoir body 54 may be fabricated from a thin flexible material. The second output port 34 may include a second output port adapter 60 which is in fluid communication with the second reservoir interior volume 56. The second output port 34 may also include a second fluid line 50 which may be a flexible tube with an inner fluid lumen which connects the second reservoir interior volume 56 to the second output port adapter 60.

Figure 6B:
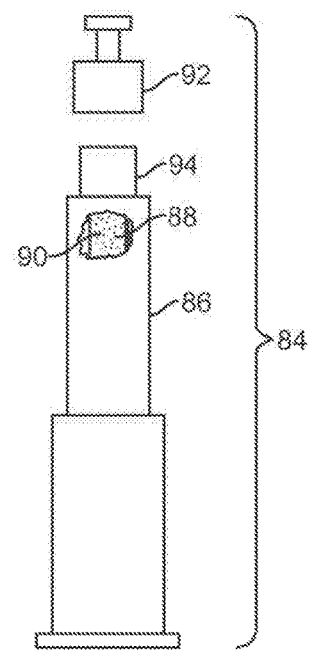
FIG. 6B shows a diabetic pen reservoir embodiment and a female luer adapter embodiment capable of mating with a port of the diabetic pen adapter.
Figure 6C:
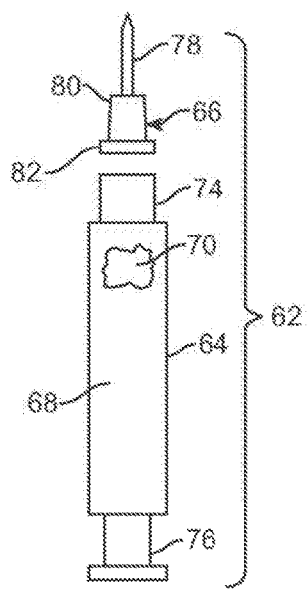
FIG. 6C shows a syringe reservoir embodiment and a hub assembly embodiment capable of mating with a syringe port of the syringe reservoir.

The fluid transfer system may also include a syringe hub assembly 62 which is shown in FIGS. 6C and 6E. FIG. 6C illustrates a syringe reservoir 64 and a hub assembly 66 in a decoupled state. FIG. 6E shows the syringe reservoir 64 coupled or releasably secured to the hub assembly 66 forming the syringe hub assembly 62. The syringe hub assembly 62 may include a syringe body 68, a syringe interior volume 70 disposed within the syringe body 68, a first fluid 72 contained within the syringe interior volume 70, and the hub assembly 66 which may be coupled to the syringe body 68. As shown in FIG. 6C, the syringe reservoir 64 has a syringe port 74 which may be in fluid communication with the syringe interior volume 70. The syringe reservoir 64 also has a plunger 76, which, when manipulated, can vary the volume of the syringe interior volume 70 and thereby draw a fluid into or out of the syringe interior volume 70. As also shown in FIG. 6C, the hub assembly 66 includes a tubular needle 78 sealingly secured to a hub distal section 80, and a hub proximal section 82 which is capable of coupling to the syringe port 74. The needle 78 of the hub assembly 66 shown in FIG. 6E is capable of penetrating the reservoir septum 44 of the first pump reservoir 36 but is mechanically incompatible with the second output port adapter 60 of the second pump reservoir 38.

The fluid transfer system may also include a diabetic pen reservoir assembly 84 as shown in FIGS. 6B, 6I, and 6J. The diabetic pen reservoir assembly 84 shown in FIG. 6B may include a diabetic pen reservoir body 86, a pen interior volume 88 disposed within the diabetic pen reservoir body 86, a second fluid 90 contained within the pen interior volume 88, and a diabetic pen reservoir adapter 92. The diabetic pen reservoir body 86 may include a pen port 94 which is in fluid communication with the pen interior volume 88. The pen port 94 may be capable of coupling with the diabetic pen reservoir adapter 92. FIGS. 6B and 6I show the diabetic pen reservoir adapter 92 and diabetic pen reservoir body 86 in a decoupled state, while FIG. 6J illustrates the diabetic pen reservoir adapter 92 as it is coupled to the diabetic pen reservoir body 86. The diabetic pen reservoir adapter 92 is configured to be mechanically compatible with the second output port adapter 60 and mechanically incompatible with the input port 30 of the first pump reservoir 36. For some embodiments, the second output port adapter 60 may be a male luer adapter and the diabetic pen reservoir adapter 92 may be a female luer adapter as shown in FIGS. 6A and 6B, respectively. Additionally, the input port 30 may include a channel 96 (not shown) disposed within the multiple reservoir cartridge body 46. In this case, the channel 96 transverse diameter may be too small to accept the diabetic pen reservoir adapter 92, thus providing mechanical incompatibility and preventing the creation of a fluid communication junction between the diabetic pen reservoir assembly 84 and the first pump reservoir 36.

Figure 6D:
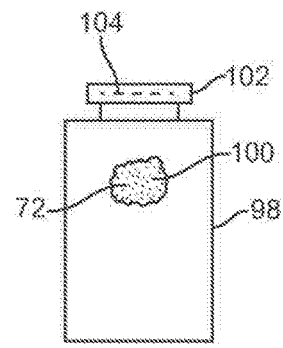
FIG. 6D shows a vial reservoir embodiment with a spigot port.

Prior to being transferred into the first pump reservoir 36, the first fluid 72 may be transferred from a vial reservoir 98 to the syringe reservoir 64 of the syringe hub assembly 62. FIG. 6D shows the vial reservoir 98. The vial reservoir 98 has a vial interior volume 100 which contains the first fluid 72. A spigot port 102 disposed on the exterior of the vial reservoir 98 contains a vial septum 104 which seals the vial interior volume 100. FIG. 6E shows the syringe hub assembly 62 of FIG. 6C and the vial reservoir 98 of FIG. 6D. FIG. 6F depicts the needle 78 of the syringe hub assembly 62 penetrating the vial septum 104 disposed within the spigot port 102 of the vial reservoir 98 thereby creating a fluid communication junction between the vial reservoir 98 and the syringe reservoir 64. FIG. 6F also depicts the plunger 76 being activated in order to transfer the first fluid 72 from the vial reservoir 98 to the syringe reservoir 64. After the first fluid 72 has been transferred from the vial reservoir 98 to the syringe hub assembly 62, it may then be transferred into the first pump reservoir 36. Similarly, the second fluid 90 may be transferred from the diabetic pen reservoir assembly 84 to the second pump reservoir 38. The fluid transfer system illustrated in FIGS. 6A-6F may be used to achieve these fluid transfers.

Some embodiments of a method for transferring fluids using the fluid transfer system are shown in FIGS. 6H-6L. The method may include creating a first fluid communication junction between the first pump reservoir 36 and the syringe reservoir 64 by piercing the reservoir septum 44 of the first input port 30 with the needle 78 of the syringe hub assembly 62 as is shown in FIG. 6G. FIG. 6G shows the needle 78 of the syringe hub assembly 62 inserted into the input port 30 of the multiple reservoir cartridge 28. FIG. 6H is a sectional view of FIG. 6G showing the needle 78 having penetrated the reservoir septum 44. The first fluid 72 is shown being transferred from the syringe reservoir 64 to the first pump reservoir 36 through the needle 30 which is in fluid communication with the first reservoir interior volume 42. The first fluid 72 may be transferred by depressing the plunger 76 of the syringe reservoir 64. The needle 78 may be configured such that it is mechanically incompatible with the second output port adapter 60 of the second output port 34 of the second pump reservoir 38 so as to mechanically prevent coupling between the syringe reservoir 64 and the second output port 34 and the creation of a fluid communication junction between the syringe reservoir 64 and the second output port 34.

The method may also include creating a second fluid communication junction between the second pump reservoir 38 and the diabetic pen reservoir assembly 84 by coupling the second output port adapter 60 of the second output port 34 to the diabetic pen reservoir adapter 92. FIG. 6K depicts the diabetic pen reservoir assembly 84 coupled to the second output port adapter 60. FIG. 6L is a sectional view of FIG. 6K showing the second fluid 90 being transferred from the diabetic pen reservoir assembly 84 to the second reservoir interior volume 56 of the second pump reservoir 38. The diabetic pen reservoir adapter 92 is configured such that it is mechanically incompatible with the input port 30 so as to prevent the creation of a fluid communication junction between the diabetic pen reservoir adapter 92 and the input port 30.

FIGS. 6H-6L depict the successful transfer of the first fluid 72 from the syringe reservoir 64 to the first pump reservoir 36, and the transfer of the second fluid 90 from the diabetic pen reservoir assembly 84 to the second pump reservoir 38. The method embodiment discussed may be performed by a patient or caregiver filling the multiple reservoir cartridge 28 of a pump device 10 with multiple pharmaceutical agents. In some cases it may be important that during the refilling procedure each agent is delivered to its appropriate respective receptacle due to the fact that the pump device 10 may deliver different agent doses from each receptacle. The existence of mechanical incompatibilities between the various interface ports in the method discussed may be used to prevent the user from transferring the wrong agent to the wrong receptacle reservoir.

Figure 7A:
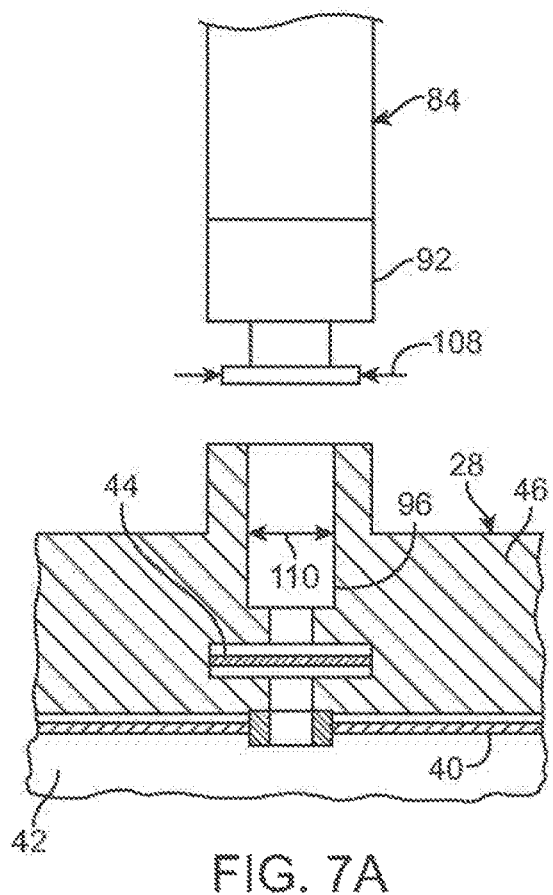
FIG. 7A illustrates an embodiment of mechanical incompatibility between the pen reservoir assembly embodiment of FIG. 6J and the input port of the dual reservoir cartridge embodiment of FIG. 6A.

In some cases the second output port adapter 60 of the fluid transfer system may be a male luer adapter and the diabetic pen reservoir adapter 92 may be a female luer adapter as shown in FIGS. 6A and 6B, respectively. Additionally, the reservoir septum 44 may be disposed within a channel 96 of the multiple reservoir cartridge body 46. In this case, if the user incorrectly attempts to transfer the second fluid 90 from the diabetic pen reservoir assembly 84 to the first pump reservoir 36, this would necessitate the attempted creation of a fluid communication junction between the diabetic pen reservoir adapter 92 and the input port 30 of the multiple reservoir cartridge 28. FIG. 7A illustrates how the mechanical incompatibility between the diabetic pen reservoir adapter 92 of the diabetic pen reservoir assembly 84 and the input port 30 (shown in the section view of FIG. 6H) prevents the creation of a fluid communication junction between the diabetic pen reservoir assembly 84 and the first pump reservoir 36.

In order to establish a fluid communication junction between the diabetic pen reservoir assembly 84 and the first pump reservoir 36, the septum 44, which seals the first reservoir interior volume 42, needs to be penetrated or otherwise interrupted. As discussed above, this may be carried out by a sharpened tubular member such as the needle 78 which is configured to reach the septum 44 and has a sharpened end which is configured to penetrate the septum 44. As shown in FIG. 7A, the outer transverse diameter 108 of the diabetic pen reservoir adapter 92 is too large to insert into the interior transverse diameter 110 of the channel 96 of the input port 30. In addition, the end of the diabetic pen reservoir adapter 92 is blunted and is not configured to penetrate the septum 44 even if the diabetic pen reservoir adapter 92 was small enough to pass through the channel 96 and reach the septum 44. For some embodiments, the septum 44 and any other such septum embodiments discussed herein may be made from or may include a layer of resilient material that resists penetration by a blunt object. For some embodiments, the septum may be made from or may include a layer of any suitable elastomeric material, including rubber or suitable polymers. Thus, the creation of a viable fluid communication junction between the two embodiments is prevented by their mechanical incompatibility.

Figure 7B:
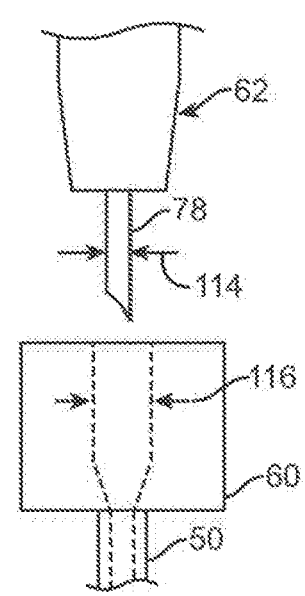
FIG. 7B illustrates an embodiment of the mechanical incompatibility between the syringe hub assembly embodiment of FIG. 6E and a male luer adapter of the first input port of the dual reservoir cartridge embodiment of FIG. 6A.

If a user attempts to transfer the first fluid from the syringe reservoir 64 to the second pump reservoir 38, this would necessitate the attempted creation of a fluid communication junction between the needle 78 of the syringe hub assembly 62 and the second output port adapter 60 of the second output port 34. FIG. 7B illustrates how the mechanical incompatibility between the needle 78 and the second output port adapter 60 mechanically prevents the creation of a fluid communication junction between the syringe reservoir 64 and the second pump reservoir 38. As shown in FIG. 7B, the outer transverse diameter 114 of the needle 78 is too small to form a fluid seal with the inner transverse diameter 116 of the second output port adapter 60. Thus, the creation of a viable fluid communication junction between the components is prevented by their mechanical incompatibility. If the needle 78 were inserted into the second output port adapter 60, any fluid dispensed from the needle 78 will leak from the gap between the outer transverse diameter 114 of the needle 78 and the inner transverse diameter 116 of the second output port adapter 60. Thus, no pressure differential would be created between the syringe reservoir 64 and the second pump reservoir 38 and therefore no fluid would be transferred into the second pump reservoir 38.

The components of an embodiment of a fluid transfer system are shown in FIG. 8A-8 K. The fluid transfer system may include a multiple reservoir cartridge 118 having a first pump reservoir 120 with a first pump reservoir body 122 and a first reservoir interior volume 124 disposed within the first pump reservoir body 122. The first pump reservoir body 122 may be fabricated from a thin flexible material. The multiple reservoir cartridge may also have a multiple reservoir cartridge body 119. The first pump reservoir 120 may include an input port 126 which has a reservoir septum 128 that seals the first reservoir interior volume 124. The first pump reservoir 120 may also include a first output port 130 which is in fluid communication with the first reservoir interior volume 124. The first output port 130 may include a first fluid line 132 (which may be, e.g., a flexible tube) which has an inner lumen and which connects the first reservoir interior volume to a first output port adapter 134.

The multiple reservoir cartridge 118 of FIG. 8A may also include a second pump reservoir 136 which may have a second pump reservoir body 138 and a second reservoir interior volume 140 disposed within the second pump reservoir body 138. The second pump reservoir body 138 as shown in FIG. 8G may be fabricated from a thin flexible material. The second pump reservoir 136 may also include a second output port 142 which may be in fluid communication with the second reservoir interior volume 140. The second output port 142 may include a second fluid line 144 which may be a flexible tube which has an inner lumen and which connects the second reservoir interior volume 140 to a second output port adapter 146.

The fluid transfer system may also include a syringe hub assembly 148 as shown in FIG. 8D. The syringe hub assembly 148 includes a first syringe reservoir 150 and a hub assembly 152, both of which are shown in FIG. 8B. The first syringe reservoir 150 shown in FIG. 8B may include a first syringe body 154 and a first syringe interior volume 156 disposed within the first syringe body 154. The first syringe body 154 may also include a first syringe port 158 which is capable of coupling with the hub assembly 152. The first syringe reservoir 150 may also have a first plunger 160 which may form a slidable fluid tight seal against an inner surface of a bore of the interior volume and when manipulated can vary the volume of the first syringe interior volume 156 and thereby transfer a fluid into or out of the first syringe interior volume 156. The hub assembly 152 includes a tubular needle 162 having an inner lumen, the tubular needle being sealingly secured to a hub distal section 164 and a hub proximal section 166 which is capable of coupling to the first syringe port 158. The needle 162 of the hub assembly 152 shown in FIG. 8B is capable of penetrating the reservoir septum 128 of the first pump reservoir 120, but is mechanically incompatible with the second output port adapter 146 of the second pump reservoir 136. FIG. 8D shows the hub assembly 152 coupled to the first syringe reservoir 150, thus forming the syringe hub assembly 148. The hub assembly 152 is coupled or releasably secured to the first syringe reservoir 150.

A first vial reservoir 168 is shown in FIG. 8B. The first vial reservoir 168 has a first vial interior volume 170. A first spigot port 174 disposed on the exterior of the first vial reservoir contains a first vial septum 176 which seals the first vial interior volume 170. The first vial interior volume 170 contains a first fluid 172.

FIG. 8C includes three more components of the fluid transfer system, a vial adapter 178, a second vial reservoir 180, and a second syringe reservoir 182. The second vial reservoir 180 shown in FIG. 8C has a second vial interior volume 184 which contains a second fluid 186. A second spigot port 188 disposed on the exterior of the second vial reservoir 180 contains a second vial septum 190 which seals the second vial interior volume 184. The second syringe reservoir 182 may include a second syringe body 192 and a second syringe interior volume 194 disposed within the second syringe body 192. The second syringe body 192 may also include a second syringe port 198 which is configured for coupling with the vial adapter 178. The second syringe port 198 is contiguously formed into the second syringe body 192. The second syringe reservoir 182 may also have a second plunger 200 which forms a fluid tight slidable seal against an inner bore of the interior volume and when manipulated can vary the volume of the second syringe interior volume 194 and thereby draw a fluid into or out of the second syringe interior volume 194.

The vial adapter 178 shown in FIG. 8C has a proximal section 202 that is capable of coupling to the second vial reservoir 180 and forming a fluid communication junction with the second vial interior volume 184. The vial adapter 178 also has a distal section 204 that is capable of coupling to the second syringe port 198. The second syringe port 198 is configured such that it is capable of coupling to the second output port adapter 146 so as to form a fluid communication junction. The second syringe port 198 is also configured such that it is mechanically incompatible with the input port 126 so as to prevent a fluid communication junction between the two components.

Prior to being transferred into the first pump reservoir 120, the first fluid 172 may be transferred from the first vial reservoir 168 to the first syringe reservoir 150 of the syringe hub assembly 148. FIG. 8E shows the needle 162 of the syringe hub assembly 148 having penetrated the first vial septum 176 (shown in FIG. 8B) of the first vial reservoir 168. Also shown in FIG. 8E is the first plunger 160 being drawn back, thereby transferring the first fluid 172 from the first vial reservoir 168 to the first syringe reservoir 148. In a similar manner, before the second fluid 186 is transferred into the second pump reservoir 136, the second fluid 186 may be transferred from the second vial reservoir 180 to the second syringe reservoir 182. FIG. 8H depicts the coupling of the vial adapter 178 and the second vial reservoir 180. FIG. 8I shows the second syringe port 198 of the second syringe reservoir 182 being coupled to the distal section 204 vial adapter 178. After the vial adapter 178 has been coupled to the second syringe reservoir 182, the second fluid 186 may be transferred from the second vial reservoir 180 to the second syringe reservoir 182.

Some embodiments of a method for transferring fluids using the fluid transfer system are shown in FIGS. 8F, 8G, 8J, and 8K. Some method embodiments may include creating a first fluid communication junction between the first pump reservoir 120 and the first syringe reservoir 150 by a piercing the reservoir septum 128 of the input port 126 of the first pump reservoir 120 with the needle 162 of the syringe hub assembly 148 as is illustrated in FIG. 8F. FIG. 8G is a sectional view of FIG. 8F showing the needle 162 having penetrated the reservoir septum 128. FIG. 8G also depicts the transferring of the first fluid 172 from the first syringe reservoir 150 to the first pump reservoir 120. The needle 162 may be configured such that it is mechanically incompatible with the second output port adapter 146 of the second pump reservoir 136 so as to prevent the creation of a fluid communication junction between the first syringe reservoir 150 and the second output port 142.

The method may also include creating a second fluid communication junction between the second pump reservoir 136 and the second syringe reservoir 182 by coupling the second output port adapter 134 of the second pump reservoir 136 to the second syringe port 198 of the second syringe reservoir 182 as is shown in FIG. 8J. FIG. 8K is a sectional view of FIG. 8J showing the second fluid 186 being transferred from the second syringe reservoir 182 to the second pump reservoir 136. The second syringe port 198 is configured such that it is mechanically incompatible with the input port 126 so as to prevent the creation of a fluid communication junction between the second syringe reservoir 182 and the first pump reservoir 120 if such a fluid communication junction is attempted by a user.

With regard to the method shown in FIGS. 8E-8K, there may be mechanical compatibilities and mechanical incompatibilities configured into the various port interfaces which are used to transfer the fluids between the respective supply and receptacle reservoirs. The purpose of the mechanical incompatibilities is to prevent the user from transferring the first fluid 172 from the first syringe reservoir 150 to the second pump reservoir 136, and/or from transferring the second fluid 186 from the second syringe reservoir 182 to the first pump reservoir 120. These mechanical compatibilities and incompatibilities may be incorporated into structures such as second output port adapter 146 and the hub assembly 152, as well as into the second syringe port 198 and the input port 126.

In some cases, the second output port adapter 146 of the fluid transfer system may be configured as a female luer adapter as shown in FIG. 8A and the second syringe port 198 may be configured as a male luer adapter as shown in FIG. 8C. Additionally, the reservoir septum 128 may be disposed within a channel 206 of the multiple reservoir cartridge body 119. If a user incorrectly attempts to transfer the first fluid 172 from the first syringe reservoir 150 to the second pump reservoir 136, this would necessitate the attempted creation of a fluid communication junction between the needle 162 of the hub assembly 152 and the second output port adapter 146 of the second output port 142.

FIG. 9A illustrates how the mechanical incompatibility between needle 162 and the second output port adapter 146 prevents the creation of a viable fluid communication junction between the first syringe reservoir 150 and the second pump reservoir 136. As shown in FIG. 9A, an exterior transverse diameter 208 of the needle 162 is too small to form a fluid seal with an interior transverse diameter 210 of the second output port adapter 146. Thus, the creation of a viable fluid communication junction between the two embodiments is prevented by their mechanical incompatibility. In some cases, if the needle 162 is inserted into the second output port adapter 146, any fluid dispensed from the needle 162 will leak from the gap between the exterior transverse diameter 208 of the needle 162 and the interior transverse diameter 210 of the second output port adapter 146.

If the user attempts to transfer the second fluid 186 from the second syringe reservoir 182 to the first pump reservoir 120, this would necessitate the attempted creation of a fluid communication junction between the second syringe port 198 of the second syringe reservoir 182 and the channel 206 of the input port 126. FIG. 9B illustrates how the mechanical incompatibility between the second syringe port 198 and the input port 126 (shown in section view see FIG. 8) prevents the creation of a fluid communication junction between the second syringe reservoir 182 and the first pump reservoir 120.

In order to create a fluid communication junction between the second syringe reservoir 182 and the first pump reservoir 120, the reservoir septum 128, which seals the first reservoir interior volume 124, needs to be penetrated or otherwise interrupted. As discussed above, this may be carried out by a sharpened tubular member such as the needle 162 which is configured to reach the reservoir septum 128 and which has a sharpened distal end configured to penetrate the reservoir septum 128. As shown in FIG. 9B, the exterior transverse diameter 212 of the second syringe port 198 is too large to insert into the interior transverse diameter 214 of the channel 206. In addition, the second syringe port 198 is blunted and is not configured to penetrate the reservoir septum 128 even if the second syringe port 198 was small enough to pass through the channel 206 and reach the reservoir septum 128. The creation of a viable fluid communication junction between the two embodiments is thereby prevented by their mechanical incompatibility.

Figure 10A:
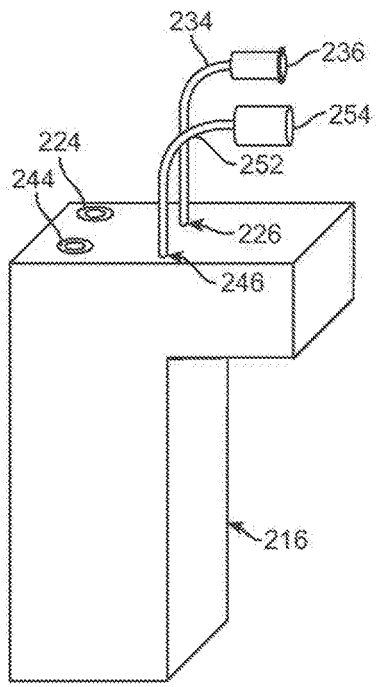
FIG. 10A is a perspective view of a dual reservoir cartridge embodiment with multiple keyed inputs and multiple outputs.

FIGS. 10A-10D depict the components of a fluid transfer system embodiment. FIG. 10A shows a multiple reservoir cartridge embodiment 216. The multiple reservoir cartridge 216 may include a first pump reservoir 218 (as shown in FIG. 14C) having a first pump reservoir body 220 which may have a first reservoir interior volume 222 disposed within it. The first pump reservoir body 220 may be fabricated from a thin flexible material. The first pump reservoir 218 may also include a first keyed port 224 and a first output port 226. The first keyed 224 port may include a first channel 228 which is in fluid communication with the first reservoir interior volume 222. The first channel 228 may incorporate a first reservoir septum 230 which is disposed within a multiple reservoir cartridge body 232 and which seals the first channel 228. The first output port 226 may include a first fluid line 234 that may be a flexible tube. The first fluid line 234 is in fluid communication with the first reservoir interior volume 222 and is attached to a first output port adapter 236.

The multiple reservoir cartridge 216 of FIG. 10A may also include a second pump reservoir 238 (as shown in FIG. 14C) having a second pump reservoir body 240 which may have a second reservoir interior volume 242 disposed within it. The second pump reservoir body 240 may be fabricated from a thin flexible material. The second pump reservoir 238 may also include a second keyed port 244 and a second output port 246. The second keyed port 244 may include a second channel 248 which is in fluid communication with the second reservoir interior volume 242. The second channel 248 may incorporate a second reservoir septum 250 which is disposed within the multiple reservoir cartridge body 232 and which seals the second channel 248. The second output port 246 may include a second fluid line 252 that may be a flexible tube having an inner lumen or conduit extending therein. The second fluid line 252 is in fluid communication with the second reservoir interior volume 242 and is attached to a second output port adapter 254.

Figure 10B:
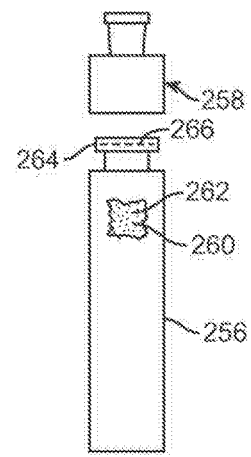
FIG. 10B shows embodiments of a first vial reservoir and a first vial adapter assembly.
Figure 10C:
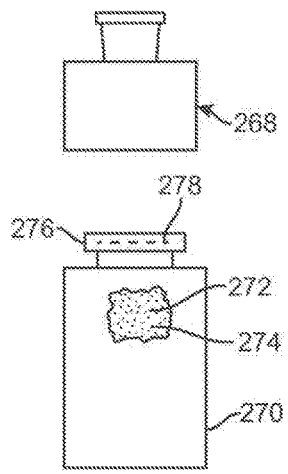
FIG. 10C shows embodiments of a second vial reservoir and a second vial adapter assembly.

The fluid transfer system may also include a first vial reservoir 256 and a first vial adapter assembly 258. Both components are shown in FIG. 10B. The first vial reservoir 256 has a first vial interior volume 260 which contains a first fluid 262. A first spigot port 264 disposed on the exterior of the first vial reservoir 256 contains a first vial septum 266 which seals the first vial interior volume 260 from the surrounding environment. FIG. 10C shows a second vial adaptor assembly 268 and a second vial reservoir 270. The second vial reservoir 270 shown in FIG. 10C has a second vial interior volume 272 which contains a second fluid 274. A second spigot port 276 disposed on the exterior of the second vial reservoir 270 contains a second vial septum 278 which seals the second vial interior volume 272.

Figure 10D:
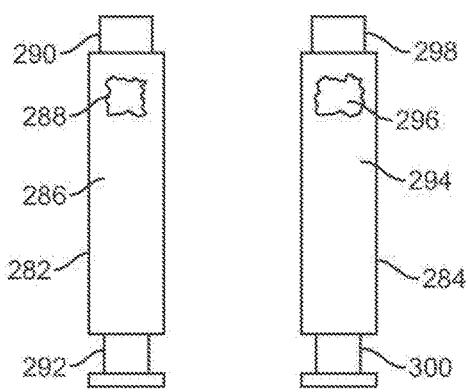
FIG. 10D shows embodiments of a first syringe reservoir and a second syringe reservoir.

The fluid transfer system may also include a first syringe reservoir 282 and a second syringe reservoir 284, both of which are shown in FIG. 10D. The first syringe reservoir 282 shown in FIG. 10D may include a first syringe body 286 and a first syringe interior volume 288 disposed within the first syringe body 286. The first syringe body 286 may also include a first syringe port 290. The first syringe reservoir 282 may also have a first plunger 292 which may be slidingly sealed to an inner bore of the interior volume and when manipulated can vary the volume of the first syringe interior volume 288 and thereby draw a fluid into or out of the first syringe interior volume 288. The second syringe reservoir 284 is also shown in FIG. 10D and may include a second syringe body 294 and a second syringe interior volume 296 disposed within the second syringe body 294. The second syringe body 294 may also include a second syringe port 298. The second syringe reservoir 284 may also have a second plunger 300 which may be slidingly sealed against an inner bore of the interior volume 296 and when manipulated can vary the volume of the second syringe interior volume 296 and thereby draw a fluid into or out of the second syringe interior volume 296. FIGS. 10E-10G show the multiple reservoir cartridge 216 of FIG. 10A. FIG. 10G depicts an enlarged view of the multiple reservoir cartridge 216 which shows the first keyed port 224 and the second keyed port 244.

Figure 11A:
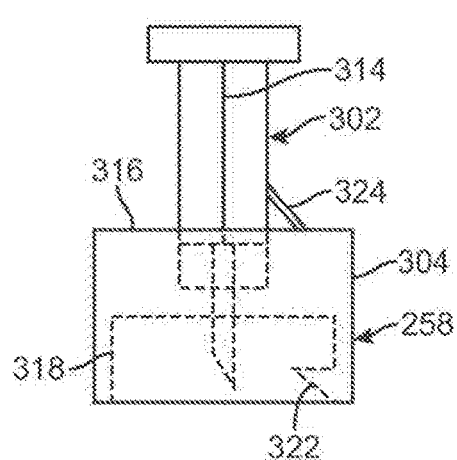
FIGS. 11A and 11B depict a first vial adapter assembly embodiment.
Figure 11B:
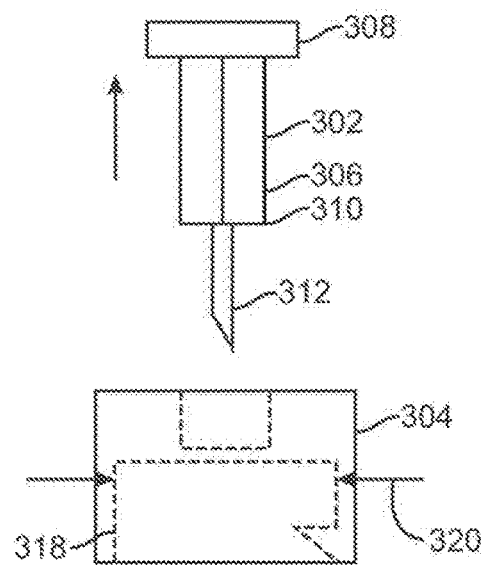

FIG. 11A shows the first vial adapter assembly 258 which may include a first hub assembly 302 and a first vial adapter 304. The first hub assembly 302 may include a first hub body 306 having a proximal section 308 which is capable of mating with a syringe port, and a distal section 310 which is sealingly secured to a first tubular needle 312 as shown in FIG. 11B. The first needle 312 may be fabricated from stainless steel or any other suitable metal, and the first needle 312 can vary in gauge size from about 16 gauge to about 30 gauge. The first hub assembly 302 may also include a first hub key feature 314 that is mechanically compatible with the first keyed port 224, but is mechanically incompatible with the second keyed port 244. The first hub body 306 and first hub key feature 314 may be fabricated from any suitable polymer.

The first vial adapter 304 may include a first vial adapter body 316 having a first distal cavity 318 which may be fabricated such that it has a substantially cylindrical configuration and which has an interior transverse dimension 320 as shown in FIG. 11B configured to couple to the first spigot port 264 of the first vial reservoir 256 but not couple to the second spigot port 276 of the second vial reservoir 270. The first vial adapter body 316 may be fabricated from any suitable polymer or other material. The first distal cavity 318 may also include at least one first hooked clip 322 capable of engaging with the first spigot port 264 but not the second spigot port 276. FIG. 11A also shows a first engagement feature 324 which may releasably secure the first hub body 306 to the first vial adapter body 316 such that the first needle 312 is disposed within and is in axial alignment of the first distal cavity 318. FIG. 11B shows the first hub assembly 302 separated from the first vial adapter 304 after the first engagement feature 324 has been disengaged. The first engagement feature 324 is shown in FIG. 11A as a break away rib; however, the first engagement feature 324 could also be configured as a threaded section on the first hub body 306 and a corresponding threaded section on the first vial adapter body 316 which would allow for the coupling of the two components.

Figure 11C:
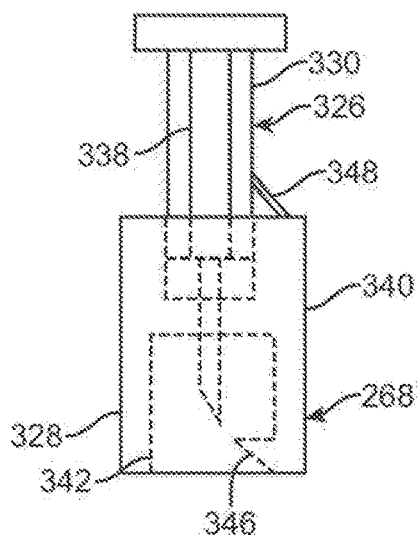
FIGS. 11C and 11D depict a second vial adapter assembly embodiment.
Figure 11D:
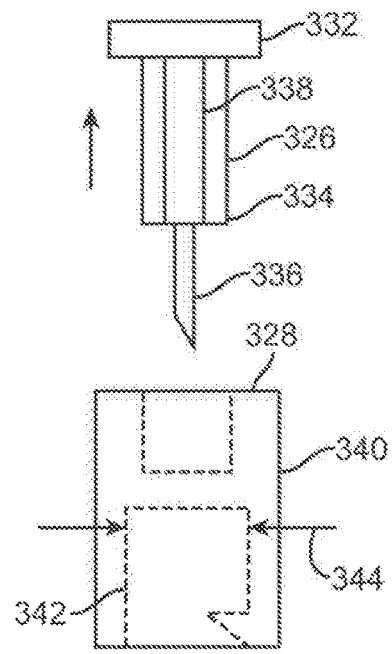

FIG. 11C shows the second vial adapter assembly 268 which may have a second hub assembly 326 and a second vial adapter 328. The second hub assembly 326 may include a second hub body 330 which has a proximal section 332 configured for mating with a syringe port, and a distal section 334 which is sealingly secured to a second tubular needle 336 as shown in FIG. 11D. The second needle 336 may be fabricated from stainless steel or any other suitable metal, and the second needle 336 can vary in gauge size from about 16 gauge to about 30 gauge. The second hub assembly 326 may also include a second hub key feature 338 that is mechanically compatible with the second keyed port 244, but is mechanically incompatible with the first keyed port 224. The second hub body 330 and second hub key feature 338 may be fabricated from any suitable polymer.

The second vial adapter 328 may include a second vial adapter body 340 having a second distal cavity 342 which may be fabricated such that it has a substantially cylindrical configuration and which has an interior transverse dimension 344 as shown in FIG. 11D configured to couple to the second spigot port 276 of the second vial reservoir 270 but not couple to the first spigot port 264 of the first vial reservoir 256. The second vial adapter body may be fabricated from any suitable polymer. The second distal cavity 342 may also include at least one second hooked clip 346 which is configured for engaging with and mechanically capturing the second spigot port 276 but not the first spigot port 264. FIG. 11C also shows a second engagement feature 348 which may releasably secure the second hub body 330 to the second vial adapter body 340 such that the second needle 336 is disposed within and is in axial alignment of the second distal cavity 342. The second engagement feature 348 may be configured as a breakable link or connection that may be configured to be separated by firmly applied manual force but not casual or incidental manual force, other similar engagement features discussed herein may be similarly configured. FIG. 11D shows the second hub assembly 326 separated from the second vial adapter 328 after the second engagement feature 348 has been disengaged. The second engagement feature 348 is shown in FIG. 11C as a break away rib; however, the second engagement feature 348 could also be configured as a threaded section on the second hub body 330 and a corresponding threaded section on the first vial adapter body 340 which would allow for the coupling of the two components.

The first keyed port 224 shown in FIG. 10G may include the first channel conduit 228 which is in fluid communication with the first reservoir interior volume 222 of the first pump reservoir 218. The reservoir interior volume 222 and any other similarly used reservoir interior volume discussed herein may be configured as an enclosed or substantially enclosed volume surrounded by an inner surface that is sealed and configured to confine a fluid such as a liquid medicament therein. The first channel 228 may be configured as a female receptacle such that it can accommodate the insertion of the first hub body 306. The first reservoir septum 230 may be disposed within and seals the first channel 228, and may be positioned at a depth 394 (see FIG. 15A) within the first channel 228 that is substantially equal to or greater than a distance 376 (see FIG. 12A) that the first needle 312 extends from the first hub body 306. The first keyed port 224 may also include a first port key feature 350 which is disposed on an inner perimeter 352 of the first channel 228, and which is configured to couple with the first hub key feature 314 but which is mechanically incompatible with the second hub key feature 338. The first port key feature 350 may include a first circular array of oblong slots 354 running parallel to a first channel central axis 356 and positioned around the perimeter 352 of the first channel 228.

The second keyed port 244 shown in FIG. 10G may include the second channel 248 which is in fluid communication with the second reservoir interior volume 242 of the second pump reservoir 238. The second channel 248 may be configured as a female receptacle such that it can accommodate the insertion of the second hub body 330. The second reservoir septum 250 is disposed within and seals the second channel 248 from an outside environment, and is positioned at a depth 398 (see FIG. 16A) within the second channel 248 that is substantially equal to or greater than a distance 388 (see FIG. 12C) that the second needle 336 extends from the second hub body 330. The second keyed port 244 may also include a second port key feature 358 which is disposed on an inner perimeter 360 of the second channel 248, and which is configured to couple with the second hub key feature 338 but which is mechanically incompatible with insertion of the first hub key feature 314. The second port key feature 358 may include a second circular array of oblong slots 362 running parallel to a second channel central axis 364 and positioned around the perimeter 360 of the second channel 248.

Figure 12A:
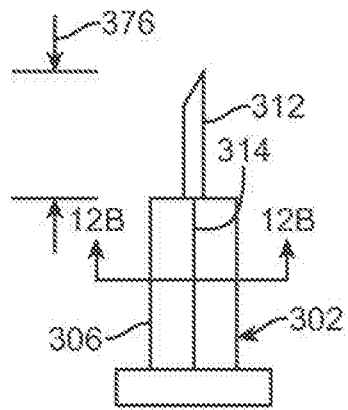
FIG. 12A depicts a first hub assembly embodiment.
Figure 12B:
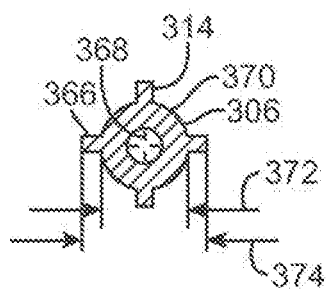
FIG. 12B is a transverse sectional view of the first hub assembly embodiment of FIG. 12A.

FIGS. 12A and 12B show the first hub assembly 302 with the first hub key feature 314. The first hub key feature 314 may include a first circular array of oblong bosses 366 running parallel to a first hub central axis 368 and positioned around the perimeter 370 of the first hub body 306. FIGS. 12A and 12B also show multiple dimensions of various device components including a first hub body diameter 372, a first hub key feature diameter 374, and the distance that the first needle extends from the first hub body 376. The first circular array of bosses 366 which include the first hub key feature 314 may be axially positioned such that they are substantially in axial alignment with the first circular array of slots 354 of the first port key feature 350 shown in FIG. 10G. The axial alignment of the first circular array of bosses 366 and the first circular array of slots 354 allows for the insertion of the first hub assembly 302 into the first keyed port 224 with the bosses 366 sliding within respective slots 354.

Figure 12C:
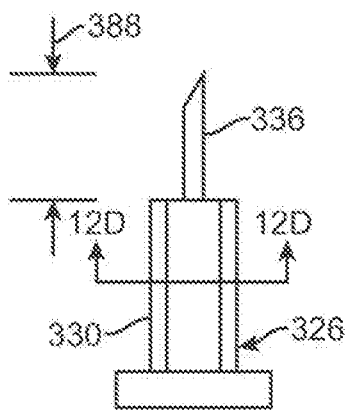
FIG. 12C depicts a second hub assembly embodiment.
Figure 12D:
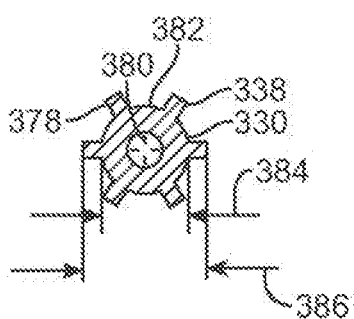
FIG. 12D is a view in transverse section of the second hub assembly embodiment of FIG. 12C.

FIGS. 12C and 12D show the second hub assembly 326 with the second hub key feature 338. The second hub key feature 338 may include a second circular array of oblong bosses 378 running parallel to a second hub central axis 380 and positioned around the perimeter 382 of the second hub body 330. FIGS. 12C and 12D also show multiple dimensions including a second hub body diameter 384, a second hub key feature diameter 386, and a distance that the second needle extends from the second hub body 388. The second circular array of bosses 378 which constitute the second hub key feature 338 are axially positioned such that they are substantially in axial alignment with the second circular array of slots 362 of the second port key feature 358 shown in FIG. 10G. The axial alignment of the second circular array of bosses 378 and the second circular array of slots 362 are configured to allow for the insertion of the second hub assembly 326 into the second keyed port 244 with the bosses 378 sliding within respective slots 362. If there is no corresponding slot 362 for each boss 378, with a matched or paired circumferential spacing, a front edge of the impaired boss 378 will impinge upon the top surface of the keyed port 244 thereby creating mechanical incompatibility and preventing insertion of the hub assembly 326.

Figure 13A:
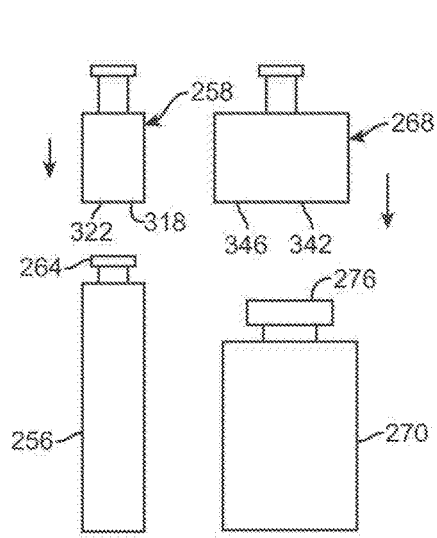
FIG. 13A-13B depict respective coupling embodiments of the first vial adapter assembly embodiment of FIG. 10B to the first vial reservoir embodiment of FIG. 10B and the second vial adapter assembly embodiment of FIG. 10C to the second vial reservoir embodiment of FIG. 10C.

The fluid transfer system embodiments discussed above may be used in order to safely transfer fluids from an appropriate supply reservoir to an appropriate receptacle reservoir. FIG. 13A shows the coupling the first vial adapter assembly 258 to the first vial reservoir 256 (both of FIG. 10B) by the insertion of the first spigot port 264 into the first distal cavity 318 such that the first needle 312 punctures the first vial septum 266 and the first vial adapter assembly 258 may be mechanically captured to the first vial reservoir 256 by the first hooked clip 322. FIG. 13A also shows the coupling the second vial adapter assembly 268 to the second vial reservoir 270 (both of FIG. 10C) by the insertion of the second spigot port 276 into the second distal cavity 342 such that the second tubular needle 336 punctures the second vial septum 278 and the second vial adapter assembly 268 is mechanically captured to the second vial reservoir 270 by the second hooked clip 346 with an inner lumen of the tubular needle 336 in fluid communication with an interior volume of the second vial reservoir 270.

Figure 13B:
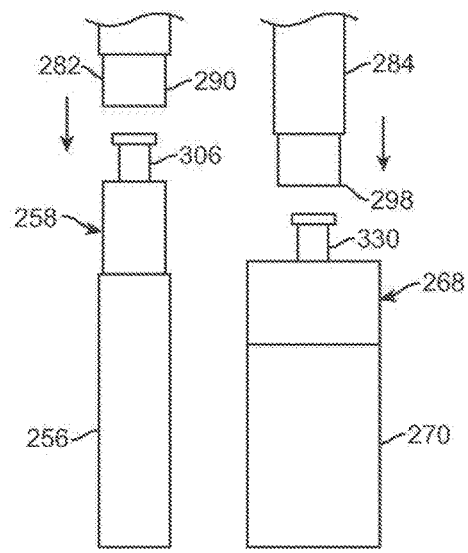
Figure 13C:
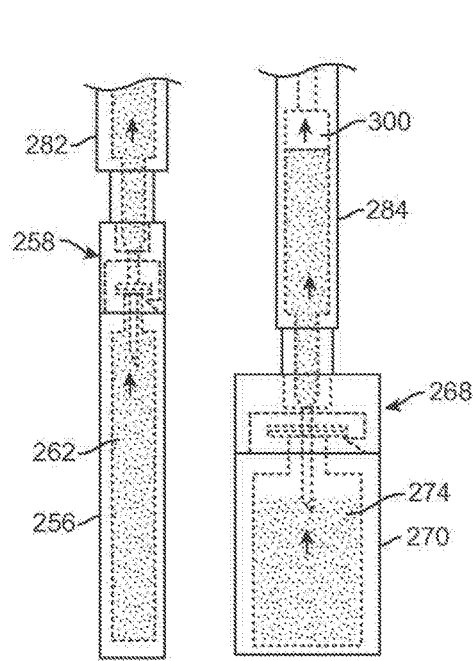
FIG. 13C depicts a coupling embodiment of the first syringe reservoir embodiment of FIG. 10D to the first vial adapter assembly embodiment of FIG. 13B as well as a coupling embodiment of the second syringe reservoir embodiment of FIG. 10D to the second vial adapter assembly embodiment of FIG. 13B.
Figure 13D:
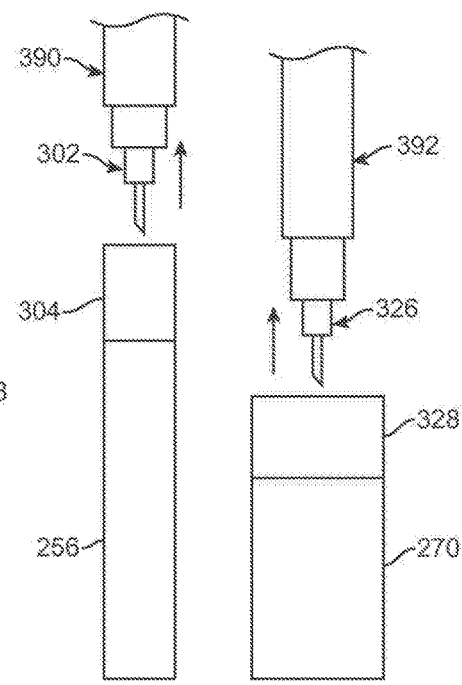
FIG. 13D depicts a first hub assembly embodiment being uncoupled from the first vial adapter body embodiment of FIG. 13C as well as a second hub assembly embodiment being uncoupled from the second vial adapter body embodiment of FIG. 13C.

FIG. 13B depicts the coupling of the first syringe reservoir 282 of FIG. 10D to the first vial adapter assembly 258 by coupling the first syringe port 290 to the first hub body 306. FIG. 13B also depicts the coupling of the second syringe reservoir 284 of FIG. 10D to the second vial adapter assembly 268 by coupling the second syringe port 298 to the second hub body 330. FIG. 13C depicts the first fluid 262 being transferred from the first vial reservoir 256 to the first syringe reservoir 282 through the first vial adapter assembly 258. FIG. 13C also shows the second fluid 274 being transferred from the second vial reservoir 270 to the second syringe reservoir 284 through the second vial adapter assembly 268. FIG. 13D depicts the detachment of the first hub assembly 302 from the first vial adapter 304 after the disengagement of the first engagement feature 324, thus creating the first syringe hub assembly 390, with the first hub assembly 302 releasably secured to the first syringe reservoir 282. FIG. 13D also depicts the detachment of the second hub assembly 326 from the second vial adapter 328 after the disengagement of the second engagement feature 348, thus creating the second syringe hub assembly 392, with the second hub assembly 326 releasably secured to the second syringe reservoir 284.

Figure 14A:
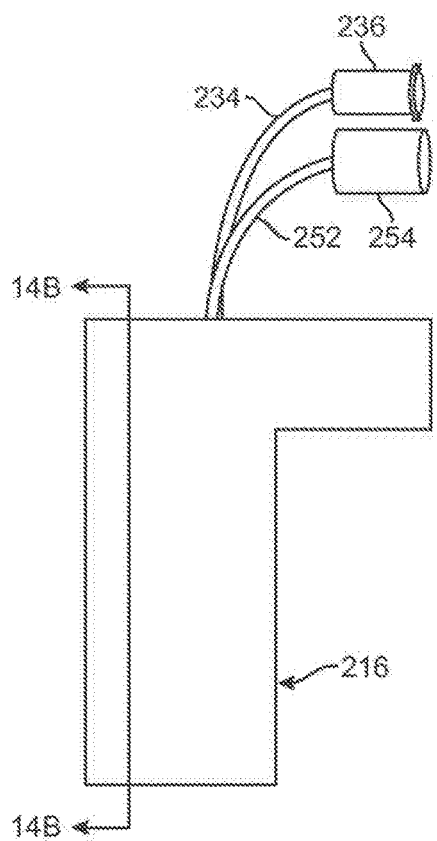
FIG. 14A depicts the dual reservoir cartridge embodiment of FIG. 10A.
Figure 14B:
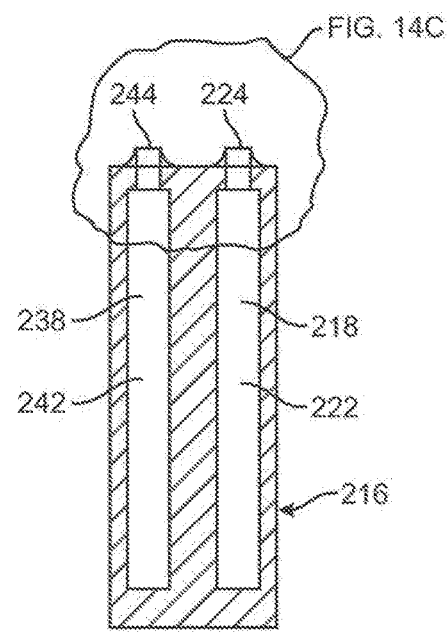
FIG. 14B is a view in transverse section of the dual reservoir cartridge embodiment shown in FIG. 14A.
Figure 14C:
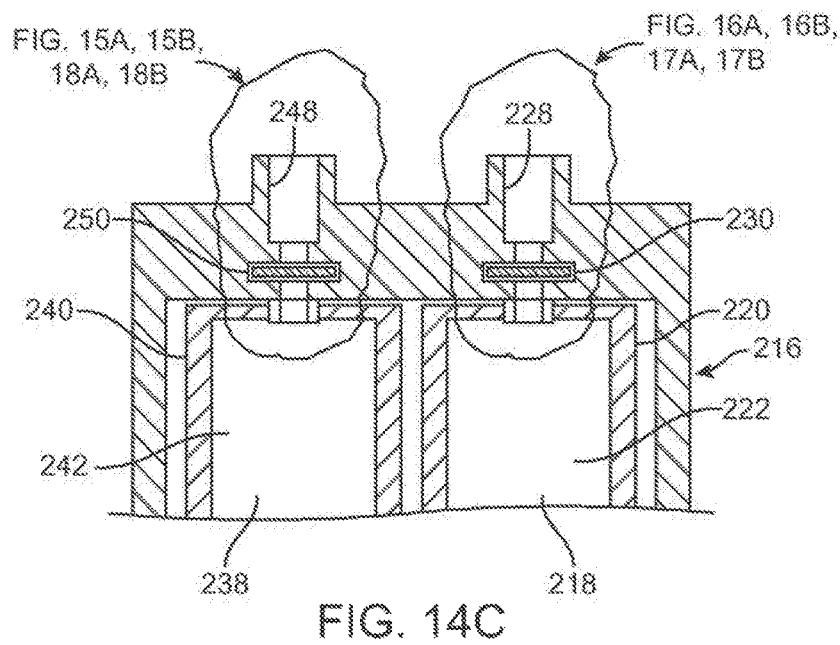
FIG. 14C is an enlarged view of the dual reservoir cartridge embodiment shown in FIG. 14B.
Figure 15A:
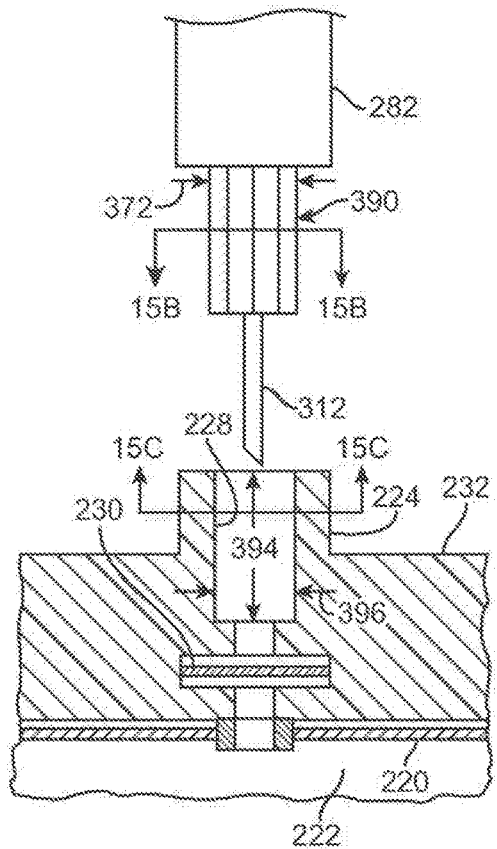
FIG. 15A shows a first keyed port embodiment of the dual reservoir cartridge of FIG. 14C and the coupled first syringe reservoir embodiment and first hub assembly embodiment of FIG. 13D.
Figure 15B:
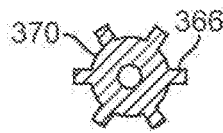
FIG. 15B is a view in transverse section of the first hub assembly embodiment of FIG. 15A.
Figure 15C:
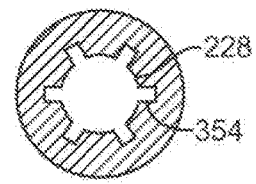
FIG. 15C is a view in transverse section of the first keyed port embodiment of FIG. 15A.
Figure 15D:
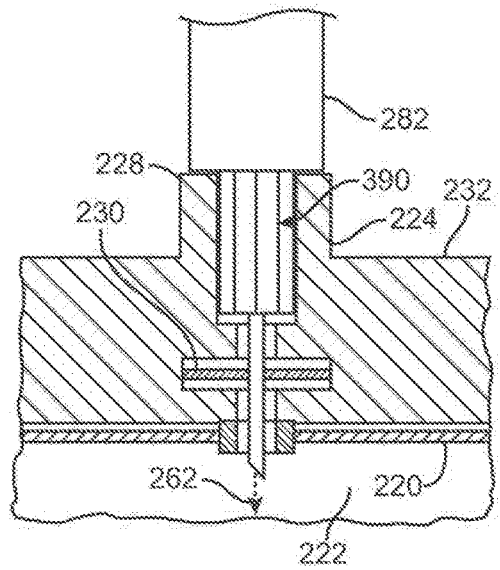
FIG. 15D shows a first fluid communication junction embodiment created by inserting the first hub assembly embodiment of FIG. 15A into the first keyed port embodiment of FIG. 15A.

FIGS. 14A-14C show the multiple reservoir cartridge 216 of FIG. 10A. FIG. 14A is a perspective view of the multiple reservoir cartridge 216, while FIG. 14B is a sectional view of the multiple reservoir cartridge 216. FIG. 14C is an enlarged detail view of FIG. 14B; the purpose of FIG. 14C is to illustrate the enlarged sectional views of the first keyed port 224 and the second keyed port 244. FIG. 15A shows the first syringe hub assembly 390 and the first keyed port 224. FIG. 15B is a transverse cross sectional view of the first hub body 306, and FIG. 15C is a transverse cross sectional view of the first keyed port 224. The first syringe hub assembly 390 may be inserted into the first keyed port 224 as shown in FIG. 15D. The axial alignment and common circumferential spacing of the first circular array of bosses 366 and the first circular array of slots 354 allows for the insertion of the first hub assembly 302 into the first keyed port 224 with each boss 366 sliding within a respective slot 354. Also a first channel diameter 396 may be configured to allow for the insertion of the first hub body 306 having first hub body diameter 372. As shown in FIG. 15D, the first tubular needle 312 has penetrated the first reservoir septum 230 thus creating a first fluid communication junction between the first syringe reservoir 282 and the first reservoir interior volume 222 through an inner lumen of the tubular needle 312. FIG. 15D also shows the first fluid 262 being transferred from the first syringe reservoir 282 to the first reservoir interior volume 222.

Figure 16A:
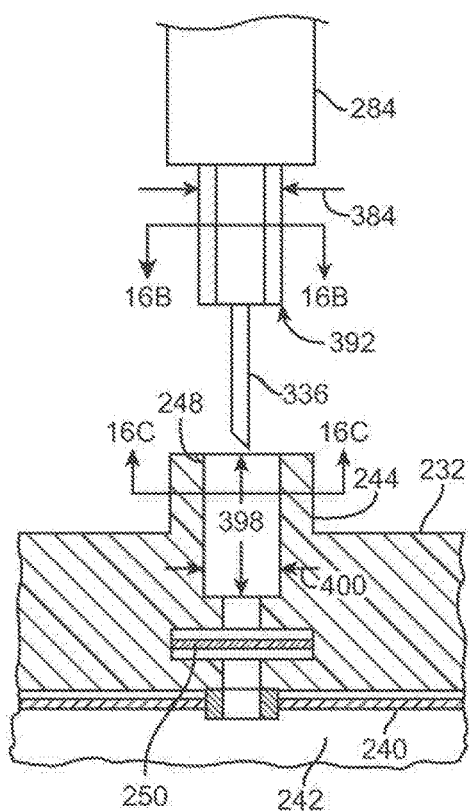
FIG. 16A shows a second keyed port embodiment of the dual reservoir cartridge of FIG. 14C and the coupled second syringe reservoir embodiment and the second hub assembly embodiment of FIG. 13D.
Figure 16B:
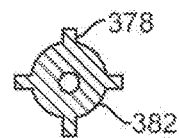
FIG. 16B is a view in transverse section of the second hub assembly embodiment of FIG. 16A.
Figure 16C:
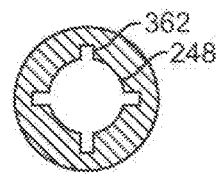
FIG. 16C is a view in transverse section of the second keyed port embodiment of FIG. 16A.
Figure 16D:
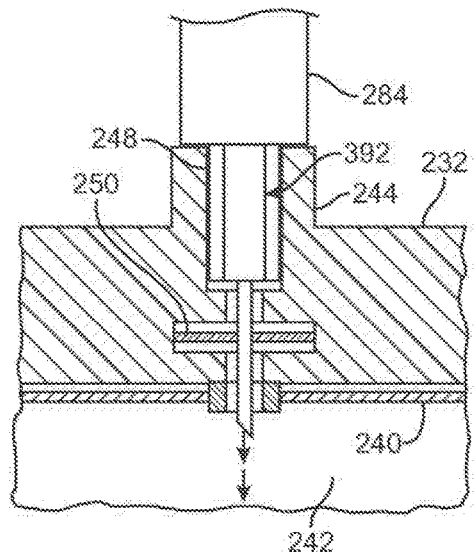
FIG. 16D shows a second fluid communication junction embodiment created by inserting the second hub assembly embodiment of FIG. 16A into the second keyed port embodiment of FIG. 16A.

FIG. 16A shows the second syringe hub assembly 392 and the second keyed port 244. FIG. 16B is a transverse cross sectional view of the second hub body 330, and FIG. 16C is a transverse cross sectional view of the second keyed port 244. As shown in FIG. 16D, the second syringe hub assembly 392 is mechanically compatible with the second keyed port 244 and may be inserted into the second keyed port 244. The axial alignment and matching circumferential spacing of the second circular array of bosses 378 and the second circular array of slots 362 allows for the insertion of the second hub assembly 326 into the second keyed port 244. Also, a second channel diameter 400 may be configured to allow for the insertion of the second hub body 330 having second hub body diameter 384. As shown in FIG. 16A, the second tubular needle 336 has penetrated the second reservoir septum 250 thus creating a second fluid communication junction between the second syringe reservoir 284 and the second reservoir interior volume 242 through the inner lumen of the second tubular needle 336. FIG. 1BD also shows the second fluid 274 being transferred from the second syringe reservoir 284 to the second reservoir interior volume 242.

A user of the fluid transfer system may attempt to transfer the first fluid 262 contained within the first syringe hub assembly 390 into the second pump reservoir 238 244. Similarly, the user may attempt transfer the second fluid 274 contained within the second syringe hub assembly 392 into the first pump reservoir 218. The user might also incorrectly attempt to couple the second vial adapter assembly 268 to the first vial reservoir 256, or incorrectly attempt to couple the first vial adapter assembly 258 to the second vial reservoir 270. With this in mind, the multiple fluid transfer interfaces used may be configured such that mechanical incompatibilities between interfaces which are not intended to be coupled prevent the creation of an incorrect fluid communication junction between two respective reservoirs.

In particular, a comparison of FIG. 17B and FIG. 17C shows that the first hub key feature embodiment 314 is mechanically incompatible with the second port key feature embodiment 358. More specifically, the first hub key feature 314 includes 6 oblong bosses and the second port key feature 358 includes 4 oblong slots. Thus, as illustrated in FIG. 17D, an attempt to insert the first syringe hub assembly 390 into the second keyed port 244 will result in the failure of the first hub body 306 to enter the second channel 248. This is because the first hub key feature diameter 374 is larger than the second channel diameter 400. As a result, as shown in FIG. 17D the first needle 312 does not penetrate the second reservoir septum 250 and therefore no fluid communication junction is created.

Figure 18A:
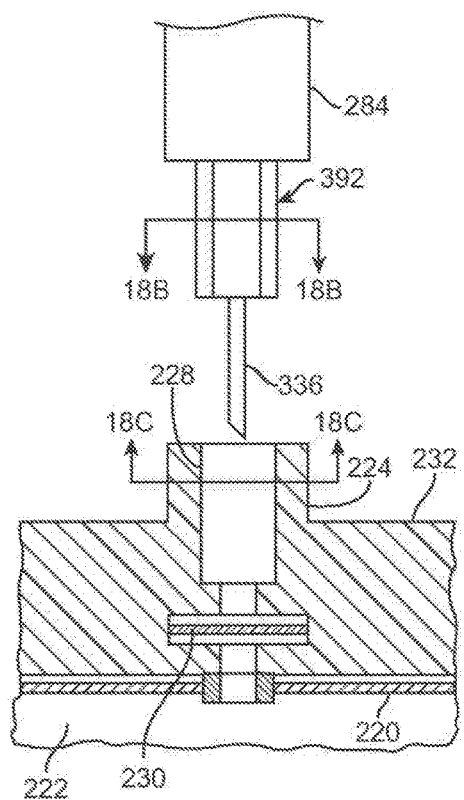
FIG. 18A shows the first keyed port embodiment of the dual reservoir cartridge of FIG. 14C and the coupled second syringe reservoir and second hub assembly embodiment of FIG. 13D.
Figure 18B:
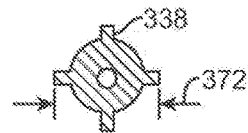
FIG. 18B is a view in transverse section of the second hub assembly embodiment of FIG. 18A.
Figure 18C:
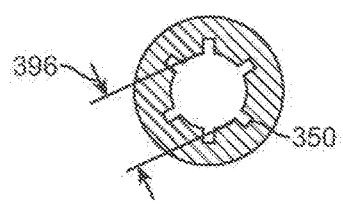
FIG. 18C is a view in transverse section of the first keyed port embodiment of FIG. 18A.
Figure 18D:
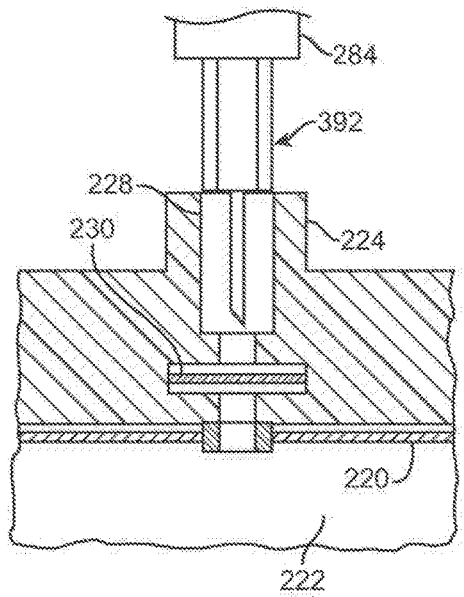
FIG. 18D illustrates an embodiment of the mechanical incompatibility between the second hub assembly embodiment of FIG. 18A and the first keyed port embodiment of FIG. 18A.

FIG. 18A shows the second syringe hub assembly 392 and the first keyed port 224. A comparison of FIGS. 18B and 18C shows that the second hub key feature embodiment 338 is mechanically incompatible with the first port key feature embodiment 350. The second hub key feature 338 comprises four oblong bosses and the second port key feature 350 includes six oblong slots. Thus, as illustrated in FIG. 18D, an attempt to insert the second syringe hub assembly 392 into the first keyed port 224 will result in the failure of the second hub body 330 to enter the first channel 228. This is because the second hub key feature diameter 372 is larger than the first channel diameter 396. As a result, as shown in FIG. 18D the second needle 336 does not penetrate the first reservoir septum 230 and therefore no fluid communication junction is created.

Figure 19A:
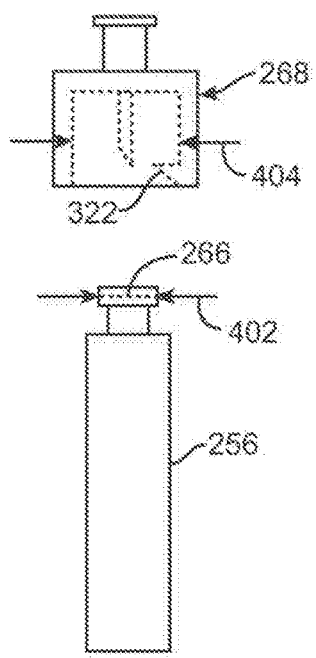
FIG. 19A illustrates an embodiment of the mechanical incompatibility between the first vial reservoir embodiment of FIG. 13A and the second vial adapter assembly embodiment of FIG. 13A.

FIG. 19A shows the second vial adapter assembly 268 of FIG. 10C and the first vial reservoir 256 of FIG. 10B. As shown in FIG. 19A, the two embodiments are mechanically incompatible because the exterior transverse diameter 402 of the first spigot port 264 of the first vial reservoir 256 does not match the interior transverse diameter 404 of the second distal cavity 342 of the second vial adapter assembly 268. Therefore, a mechanical coupling by the user between these two embodiments is impractical. The second hooked clip 346 would not engage the first spigot port 264, therefore the second hub assembly 326 could not be separated from the second vial adapter 328 after the first vial reservoir 256 and second vial adapter assembly 268 have been coupled. Therefore, a mechanical coupling by the user between these two embodiments is impractical.

Figure 19B:
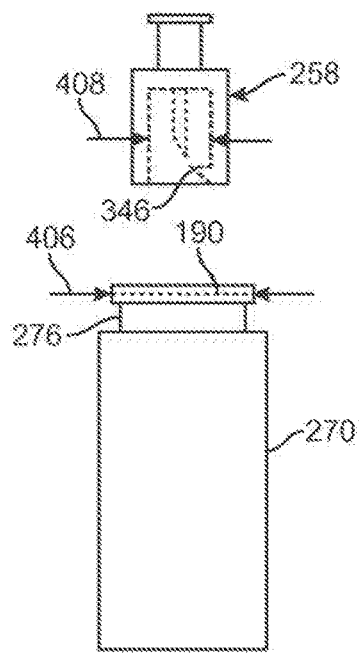
FIG. 19B illustrates an embodiment of the mechanical incompatibility between the second vial reservoir embodiment of FIG. 13A and the first vial adapter assembly embodiment of FIG. 13A.

The first vial adapter assembly 258 of FIG. 10B and the second vial reservoir 270 of FIG. 10C are mechanically incompatible because the exterior transverse diameter 406 of the second spigot port 276 of the second vial reservoir 270 is too large to insert into the interior transverse diameter 408 of the first distal cavity 318 as shown in FIG. 19B. The second spigot port 276 could not be inserted into the first distal cavity 318 so the first needle 312 cannot penetrate the second vial septum 190. Therefore, a mechanical coupling by the user between these two embodiments is prohibited.

Figure 20A:
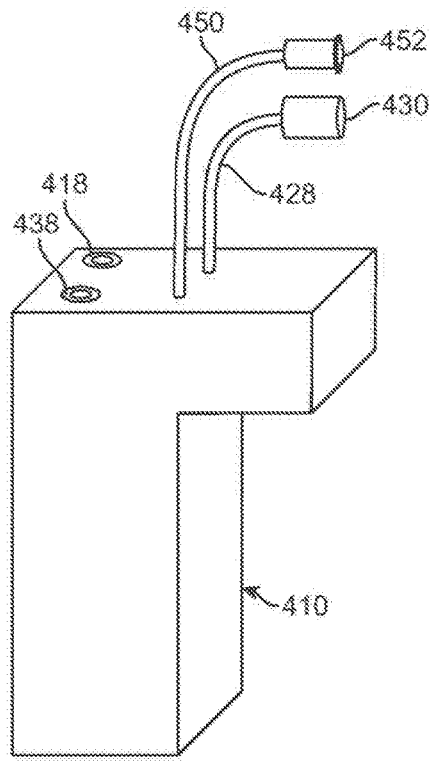
FIG. 20A is a perspective view of a multiple input and multiple output dual reservoir cartridge embodiment.

FIGS. 20A-20D show the components of a fluid transfer system embodiment. FIG. 20A shows a multiple reservoir cartridge embodiment 410 which may include a first pump reservoir 412 (as shown in FIG. 20M) which has a first pump reservoir body 414 having a first reservoir interior volume 416 which is disposed within the first reservoir body 414. The first pump reservoir body 414 may be fabricated from a thin flexible material. The first pump reservoir 412 may also include a first input port 418 which has a first channel 420 that is in fluid communication with the first reservoir interior volume 416. The first input port 418 may also include a first septum 422 that is disposed within a multiple reservoir cartridge body 424 and which seals the first channel 420. The first pump reservoir 412 may also include a first output port 426 which has a first fluid line 428 that is in fluid communication with the first reservoir interior volume 416, and a first output port adapter 430 which is secured to and in fluid communication with the first fluid line 428.

The multiple reservoir cartridge of FIG. 20A may also include second pump reservoir 432 (as shown in FIG. 20M) which may have a second pump reservoir body 434 having a second reservoir interior volume 436 which is disposed within the second pump reservoir body 434. The second pump reservoir body 434 may be comprised of a thin flexible material. The second pump reservoir 432 may also include a second input port 438 which has a second channel 440 which is in fluid communication with the second reservoir interior volume 436. A second septum 442 is disposed within the multiple reservoir cartridge body 424 and seals the second channel 440, and a port key feature 444 is disposed on a perimeter 446 of the second channel 440. The second pump reservoir 432 may also include a second output port 448 comprising a second fluid line 450 which is in fluid communication with the second reservoir interior volume 436, and a second output port adapter 452 which is secured to and in fluid communication with the second fluid line 450.

Figure 20B:
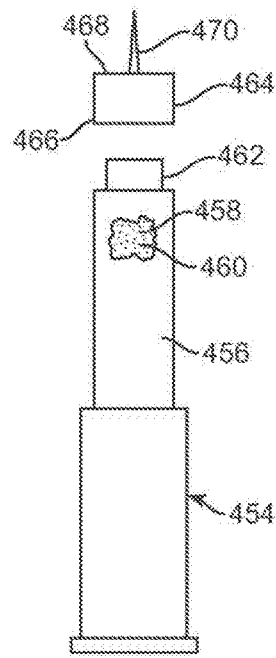
FIG. 20B shows embodiments of a diabetic pen reservoir and a bayonet needle.

FIG. 20B shows a diabetic pen reservoir 454 which may include a diabetic pen reservoir body 456 which has a pen interior volume disposed 458 within it. A first fluid 460 may be contained within the pen interior volume 458. The diabetic pen reservoir 454 may also include a pen port 462 which is in fluid communication with the pen interior volume 458. FIG. 20B also shows a bayonet needle adapter 464 which has a proximal section 466 that is capable of mating with the pen port 462 and a distal section 468 that is sealingly secured to a bayonet needle 470.

Figure 20C:
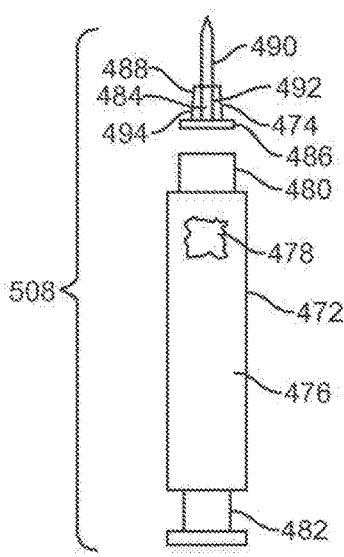
FIG. 20C shows embodiments of a syringe reservoir and a hub assembly.

A syringe reservoir 472 and a hub assembly 474 are shown in FIG. 20C. The syringe reservoir 472 may include a syringe body 476 which may have a syringe interior volume 478 disposed within the syringe body 476. The syringe reservoir 472 may also include a syringe port 480 and a plunger 482 which may be slidingly sealed to an inner bore of the syringe reservoir and when manipulated can vary the volume of the syringe interior volume 478 and thereby draw a fluid into or out of the syringe interior volume 478.

Figure 20D:
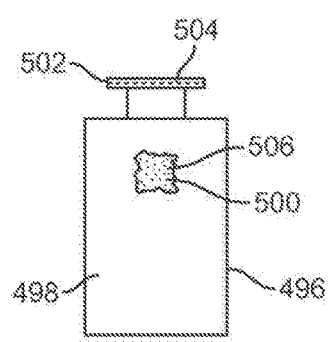
FIG. 20D shows a vial reservoir embodiment.
Figure 20E:
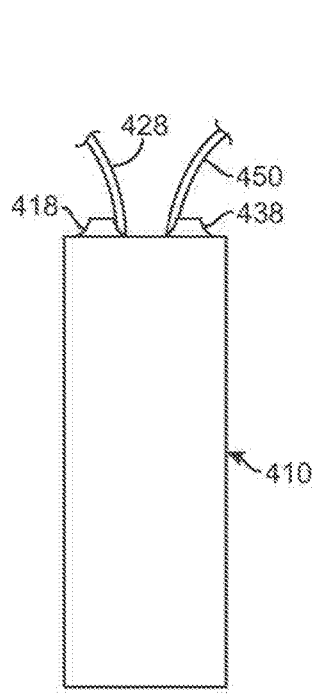
FIG. 20E is a front view of the dual reservoir cartridge embodiment of FIG. 20A.
Figure 20F:
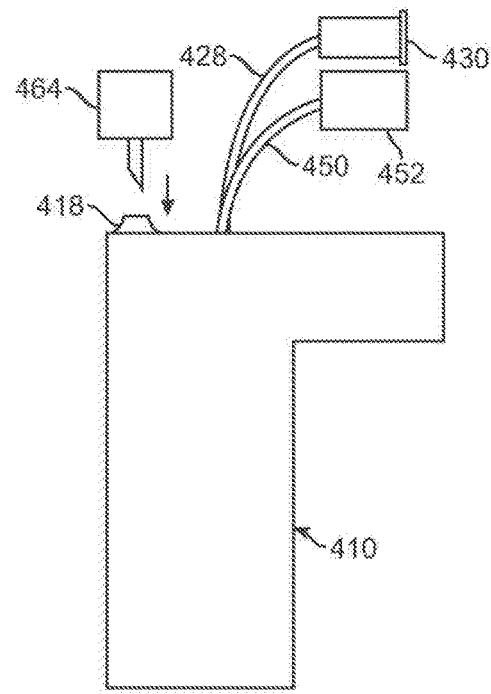
FIG. 20F is a side view of the dual reservoir cartridge embodiment of FIG. 20A.
Figure 20G:
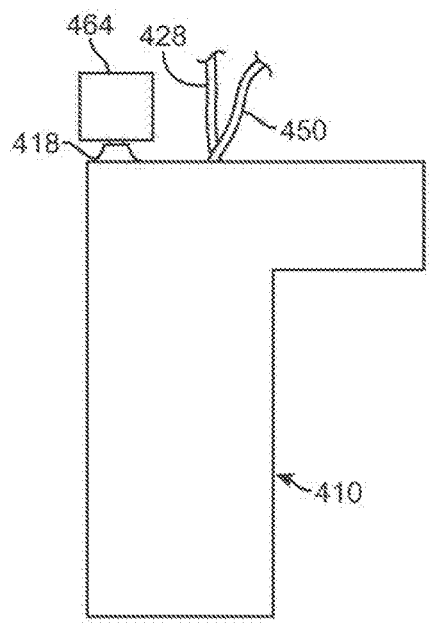
FIG. 20G depicts the bayonet needle embodiment of FIG. 20B inserted into a first port of the dual reservoir cartridge embodiment of FIG. 20A.
Figure 20H:
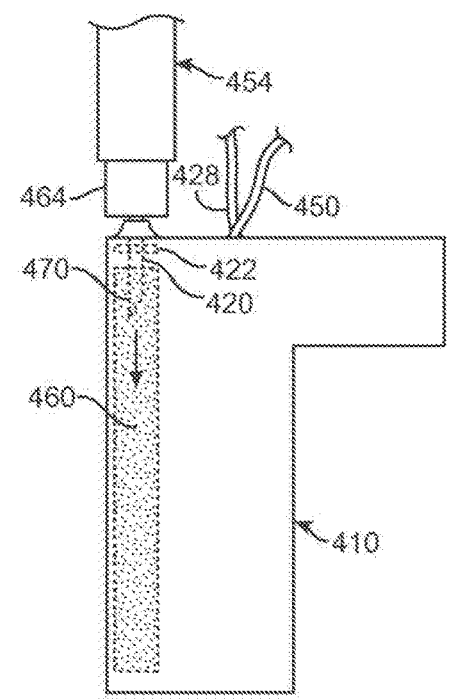
FIG. 20H depicts the diabetic pen reservoir embodiment of FIG. 20B coupled to the bayonet needle embodiment of FIG. 20G.

FIG. 20C also shows the hub assembly 474 which may include a hub body 484 having a proximal section 486 which is configured for coupling to the syringe port 480, and a distal section 488 of the hub body 484 which is sealingly secured to a tubular needle 490 having an inner lumen extending along a length thereof. The needle 490 may be configured to pierce the second septum 442 in order to create a second fluid communication junction between the syringe interior volume 478 and the second reservoir interior volume 436, but may also be configured to be mechanically incompatible with the second output port adapter 452 so as to prevent the creation of a fluid communication junction between the two components. The hub assembly 474 may also include a hub key feature 492 which is disposed on a perimeter 494 of the hub body 484, and which is mechanically compatible with the second input port 438, but is mechanically incompatible with the first input port 418. FIG. 20D shows a vial reservoir 496 which may have a vial reservoir body 498, and a vial interior volume 500 disposed within the vial reservoir body 498. The vial reservoir 496 may have a spigot port 502, and a vial septum 504 which may be disposed within the spigot port 502 and which seals the vial interior volume 500. The vial interior volume 500 may contain a second fluid 506.

FIGS. 20E-21B illustrate a fluid transfer method for a fluid transfer system embodiment. The method may include inserting the tubular bayonet needle 470 into the first channel 420 such that it penetrates the first septum 422 as shown in FIGS. 20E-20H. The method may also include creating a first fluid communication junction between the first pump reservoir 412 and the diabetic pen reservoir 454 by coupling the pen port 462 of the diabetic pen reservoir 454 to the bayonet needle adapter 464 as shown in FIG. 20H. The bayonet needle adapter 464 is releasably secured to the diabetic pen reservoir 454. The first fluid 460 may then be transferred from the diabetic pen reservoir 454 to the first pump reservoir 412 through the first fluid communication junction as is also shown in FIG. 20H.

Figure 20I:
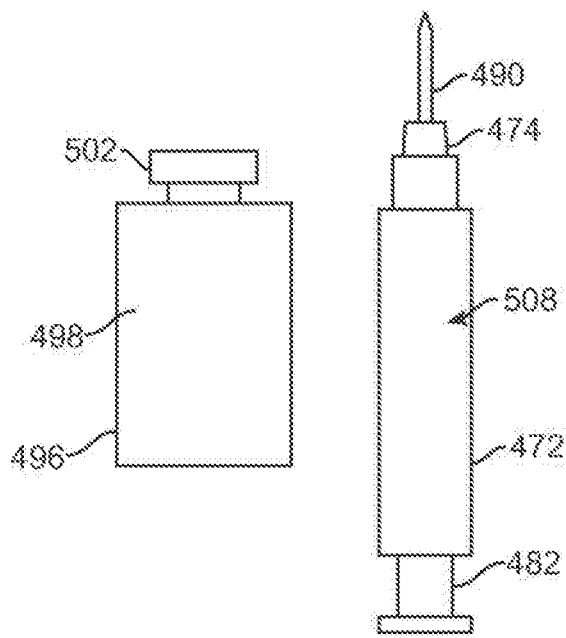
FIG. 20I shows the vial adapter embodiment of FIG. 20 D and the syringe reservoir and hub assembly embodiments of FIG. 20C coupled together.
Figure 20J:
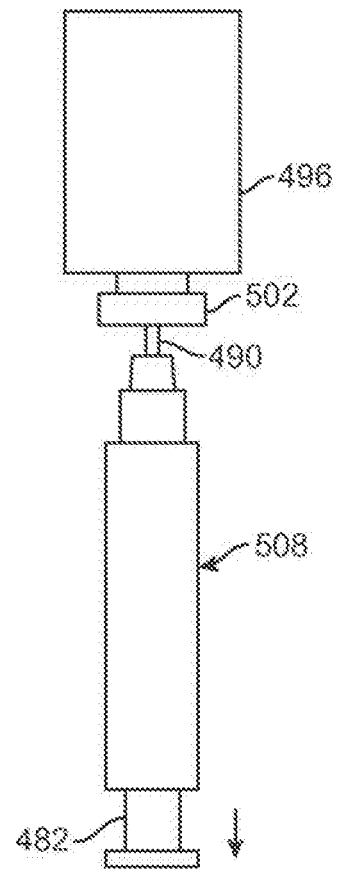
FIG. 20J shows the needle of the hub assembly embodiment of FIG. 20C inserted into a spigot port of the vial reservoir embodiment of FIG. 20D.

FIG. 20I shows the vial reservoir 496 of FIG. 20D. FIG. 20I also shows the hub assembly 474 and syringe reservoir 472, both of FIG. 20C, coupled together to form the syringe hub assembly 508. The hub assembly 474 is releasably secured to the syringe reservoir 472. FIG. 20J shows the tubular needle 490 of the syringe hub assembly 508 having penetrated the vial septum 504 (not shown) of the vial reservoir 496, thereby forming a fluid communication junction between the vial interior volume 400 (not shown) and the syringe interior volume 478 (not shown) through an inner lumen of the tubular needle 490. FIG. 20J also shows the plunger 482 of the syringe reservoir 472 being drawn back in order to transfer the second fluid 506 form the vial reservoir 496 to the syringe reservoir 472.

Figure 20K:
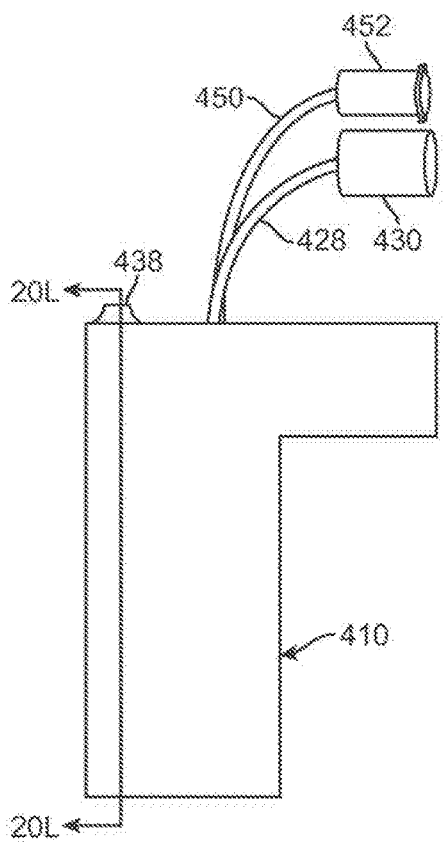
FIG. 20K shows the dual reservoir cartridge embodiment of FIG. 20A.
Figure 20L:
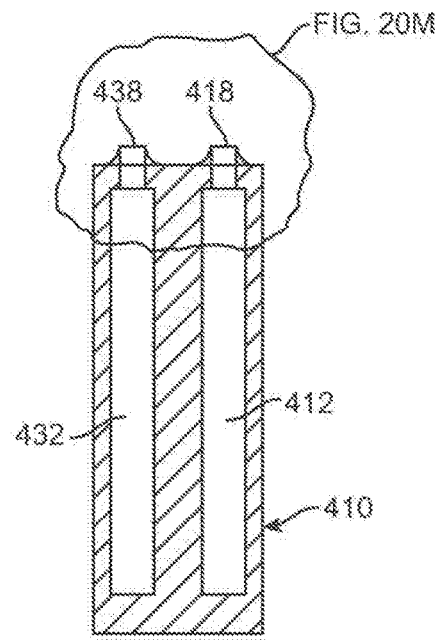
FIG. 20L is a view in transverse section of the dual reservoir cartridge embodiment of FIG. 20A.
Figure 20M:
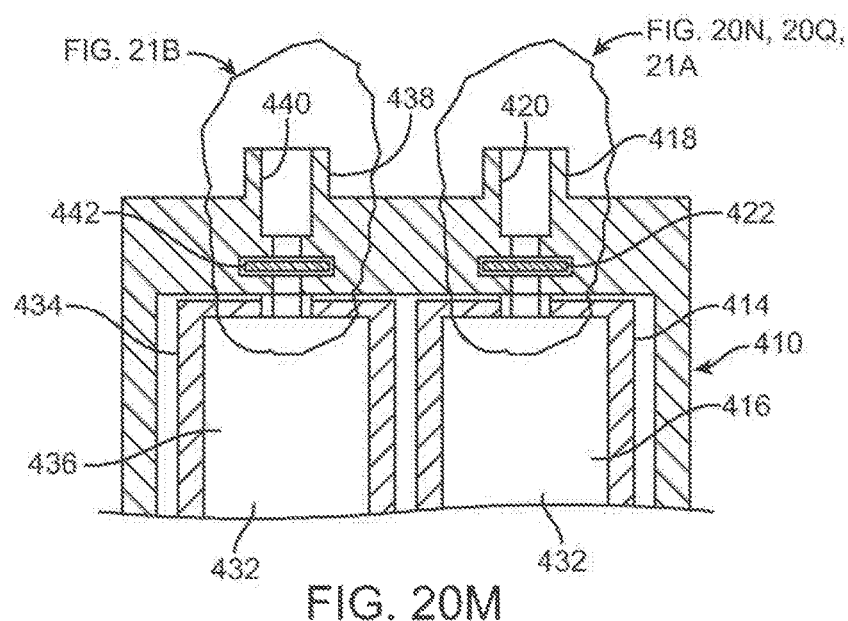
FIG. 20M is an enlarged view of the dual reservoir cartridge embodiment of FIG. 20L.

FIGS. 20K-20M show the multiple reservoir cartridge 410 of FIG. 20A. FIG. 20L is a sectional view of FIG. 20K. FIG. 20M is an enlarged view of FIG. 20L the purpose of which is to show detailed sectional views of the first input port 418 and the second input port 438. FIG. 20N shows the syringe hub assembly 508 and the second input port 438. FIG. 20O is a cross sectional view of the hub body 484, and FIG. 20P is a cross sectional view of the second input port 438. FIG. 20O shows the hub key feature 492 which consists of an array of oblong bosses 510 which run parallel to a hub central axis 512. FIG. 20O also shows a hub body diameter 518 and hub key feature diameter 520. FIG. 20P shows the port key feature 444 which consists of an array of oblong slots 514 which run parallel to a second channel central axis 516. FIG. 20P also shows a second channel diameter 522 and a port key feature diameter 524. FIG. 20O depicts the syringe hub assembly 508 inserted into the second input port 438. The axial alignment and circumferential spacing of the array of oblong bosses 510 which comprise the hub key feature 492 and the matching circular array of oblong slots 514 which comprise the port key feature 444 allows for the insertion of the hub assembly 474 into the second input port 438, with each boss 510 sliding within a respective slot 514. Also, the second channel diameter 522 is configured to allow for the insertion of the hub body 484 having a hub body diameter 518. As shown in FIG. 20Q, the tubular needle 490 has penetrated the second septum 442 thus creating a second fluid communication junction between the syringe reservoir 472 and the second reservoir interior volume 436 through an inner lumen of the tubular needle 490. FIG. 20Q also shows the second fluid 506 being transferred from the syringe reservoir 472 to the second reservoir interior volume 436.

As exemplified in the method described in connection with, e.g., FIGS. 20A-20Q, there may be mechanical compatibilities and mechanical incompatibilities designed into the various port interfaces which are used to transfer the fluids between the respective reservoirs. The purpose of the mechanical incompatibilities is to prevent the user from transferring the first fluid 460 from the diabetic pen reservoir 454 to the second pump reservoir 432, and/or from transferring the second fluid 506 from the syringe reservoir 472 to the first pump reservoir 412.

FIGS. 21A and 21B illustrate some mechanical incompatibility embodiments configured into the port interfaces for the embodiments described in FIGS. 20A-20Q. In some cases the second output port adapter 452 of the fluid transfer system may be a female luer adapter as shown in FIG. 20A, and the pen port 462 may be a male luer adapter as shown in FIG. 20B. If a user attempts to transfer the first fluid 460 from the diabetic pen reservoir 454 into the second pump reservoir 432, the exterior transverse diameter 526 of the pen port 462 is too large to insert into the second channel 440 which has a second channel diameter 552. The ability to create a fluid communication junction between the diabetic pen reservoir 454 and the second input port 438 may be further hindered by the fact that the second reservoir septum 442 is located at a lower section of the second channel 440. The second reservoir septum 442 must be penetrated in order to access the second reservoir interior volume 436, and because the pen port 462 is too large to insert into the second channel 440 the second reservoir septum 442 cannot come into contact with the pen port 462 and therefore the second reservoir septum 442 will remain intact. A fluid communication junction between the diabetic pen reservoir 454 and the second pump reservoir 432 is therefore prevented by the mechanical incompatibility between the pen port 462 and the second channel 440.

As shown in FIG. 21C, the hub body 484 incorporates the hub key feature 492 which has a hub key feature diameter 520. As shown in FIG. 21D, the first channel 420 of the first input port 418 does not have a corresponding key feature embodiment. Therefore, the hub body 484 cannot be inserted into the first channel 420 of the first input port 418 as is shown in FIG. 21B. This is because the hub key feature diameter 520 is larger than the first channel diameter 528. This being the case, the tubular needle 490 of the hub assembly 474 cannot puncture the first reservoir septum 422 of the first input port 418 and therefore no fluid communication junction can be established between an interior volume of the syringe reservoir 472 and the first pump reservoir 412.

With regard to the above detailed description, like reference numerals used therein may refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

The entirety of each patent, patent application, publication and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" may refer to one of or a plurality of the elements it modifies (e.g., "a reagent" can mean one or more reagents) unless it is contextually clear either one of the elements or more than one of the elements is described. Although the present technology has been specifically disclosed by representative embodiments and optional features, modification and variation of the concepts herein disclosed may be made, and such modifications and variations may be considered within the scope of this technology.

Certain embodiments of the technology are set forth in the claim(s) that follow(s).

The invention claimed is:

1. A system for providing medicament to a patient, comprising:
    an infusion pump including a medicament reservoir configured to contain a medicament, the infusion pump configured to deliver the medicament from the medicament reservoir to a patient;
    a vial reservoir defining an interior volume configured to contain the medicament and a spigot port in communication with the interior volume, the spigot port defining an exterior mechanical configuration configured to be provided only on vial reservoirs containing the medicament and not on vial reservoirs containing other types of medicament from the medicament; and
    a vial adapter having a cavity configured to couple to the exterior mechanical configuration of the spigot port, the vial adapter being configured to only couple to the exterior mechanical configuration of spigot ports of vial reservoirs containing the medicament and not to exterior mechanical configurations of spigot ports of vial reservoirs containing other types of medicament from the medicament.

2. The system of claim 1, wherein the exterior mechanical configuration of the spigot port has a different shape than spigot ports of vial reservoirs containing other types of medicament from the medicament.

3. The system of claim 1, wherein the exterior mechanical configuration of the spigot port is a different size than spigot ports of vial reservoirs containing other types of medicament from the medicament.

4. The system of claim 1, wherein the infusion pump is configured to deliver only the medicament to the patient and not other types of medicament from the medicament.

5. The system of claim 1, wherein the infusion pump further includes a second medicament reservoir configured to contain a second medicament, the second medicament being another type of medicament from the medicament.

6. A system for providing medicament to a patient, comprising:
   an infusion pump including a medicament reservoir configured to contain a medicament, the infusion pump configured to deliver the medicament from the medicament reservoir to a patient; and
   a vial adapter having a cavity configured to couple to an exterior mechanical configuration of a spigot port of a vial reservoir containing the medicament, the vial adapter being configured to only couple to the exterior mechanical configuration of spigot ports of vial reservoirs containing the medicament and not to exterior mechanical configurations of spigot ports of vial reservoirs containing other types of medicament from the medicament.

7. The system of claim 6, wherein the cavity of the vial adapter has a different shape than cavities of vial adapters configured to couple to spigot ports of vial reservoirs containing other types of medicament from the medicament.

8. The system of claim 6, wherein the cavity of the vial adapter has a different size than cavities of vial adapters configured to couple to spigot ports of vial reservoirs containing other types of medicament from the medicament.

9. The system of claim 6, wherein the infusion pump is configured to deliver only the medicament to the patient and not other types of medicament from the medicament.

10. The system of claim 6, wherein the infusion pump further includes a second medicament reservoir configured to contain a second medicament, the second medicament being another type of medicament from the medicament.

* * * * *